US012604824B2

(12) United States Patent
Pierce

(10) Patent No.: US 12,604,824 B2
(45) Date of Patent: Apr. 21, 2026

(54) CELERY CULTIVAR TBG 54

(71) Applicant: A. DUDA & SONS, INC., Oviedo, FL (US)

(72) Inventor: Lawrence K. Pierce, Quitman, AR (US)

(73) Assignee: A. Duda & Sons, Inc., Oviedo, FL (US)

( * ) Notice: Subject to any disclaimer, the term of this patent is extended or adjusted under 35 U.S.C. 154(b) by 312 days.

(21) Appl. No.: 18/122,881

(22) Filed: Mar. 17, 2023

(65) Prior Publication Data

US 2024/0306573 A1 Sep. 19, 2024

(51) Int. Cl.
*A01H 6/06* (2018.01)

(52) U.S. Cl.
CPC ..................................... *A01H 6/064* (2018.05)

(58) Field of Classification Search
None
See application file for complete search history.

(56) References Cited

U.S. PATENT DOCUMENTS

| | | | |
|---|---|---|---|
| 5,124,505 A | 6/1992 | Orton et al. | |
| 5,304,719 A | 4/1994 | Segebart | |
| 5,367,109 A | 11/1994 | Segebart | |
| 5,523,520 A | 6/1996 | Hunsperger et al. | |
| 5,763,755 A | 6/1998 | Carlone | |
| 5,850,009 A | 12/1998 | Kevern | |
| 6,812,385 B2 | 11/2004 | Pierce | |
| 6,822,143 B2 | 11/2004 | Pierce | |
| 7,193,142 B2 | 3/2007 | Trammell et al. | |
| 7,351,883 B2 | 4/2008 | Pierce et al. | |
| 7,365,248 B2 | 4/2008 | Pierce | |
| 8,524,993 B2 | 9/2013 | Pierce | |
| 8,598,424 B2 | 12/2013 | Pierce | |
| 8,598,425 B2 * | 12/2013 | Pierce | A01H 5/04 800/300 |
| 9,433,162 B2 | 9/2016 | Pierce | |
| 9,439,374 B2 | 9/2016 | Pierce | |
| 9,713,308 B2 | 7/2017 | Pierce | |
| 10,306,857 B1 | 6/2019 | Pierce | |
| 10,440,913 B2 | 10/2019 | Pierce | |

OTHER PUBLICATIONS

"Applying for a Plant Variety Certificate of Protection", US. Dept. Agriculture; https://www.ams.usda.gov/services/pvpo/application-help/apply; Accessed May 1, 2023. (Year: 2023).*

"Explanatory Notes On Essentially Derived Varieties Under The 1991 Act of the Upov Convention", Document adopted by the Council at its thirty-fourth extraordinary session on Apr. 6, 2017. (Year: 2017).*
Ex Parte C, 27 U.S.P.Q.2d 1492 (1992) (Year: 1992).*
Ex Parte McGowen- Board Decision in U.S. Appl. No. 14/996,093 (Year: 2020).*
Großkinsky, Dominik K., et al. "Plant phenomics and the need for physiological phenotyping across scales to narrow the genotype-to-phenotype knowledge gap." Journal of experimental botany 66.18 (2015): 5429-5440. (Year: 2015).*
Haun, William J., et al. "The composition and origins of genomic variation among individuals of the soybean reference cultivar Williams 82." Plant physiology 155.2 (2011): 645-655. (Year: 2011).*
Allard, R.W., "Breeding Self-Pollinated Plants", Principles of Plant Breeding, 2nd ed., John Wiley & Sons, Inc., 1999, pp. 175-197.
Altpeter, F., et al., "Advancing Crop Transformation in the Era of Genome Editing", *The Plant Cell*, 2016, 28:1510-1520.
Bennetzen, J.L. and Jones, J.D.G., edited by Setlow, J.K., "Approaches and progress in the molecular cloning of plant disease resistance genes", *Genetic Engineering*, 1992, 14:99-124.
Browers & Orton, "Biotechnology in Agriculture and Forestry", vol. 2: Crops 1, Ed. Y.P.S Bajaj, Springer-Verlag, Berlin, Heidelberg, 1986, pp. 405-420.
DeNolle, M.F.C., et al., "Antimicrobial peptides from *Mirabilis jalapa* and *Amaranthus caudatus:* expression, processing, localization and biological activity in transgenic tobacco", *Plant Molecular Biology*, 1996, 31:993-1008.
Eshed, Y. and Zamir, D., "Less-than-additive epistatic interactions of quantitative trait loci in tomato", *Genetics*, 1996, 143:1807-1817.
Hessayon, D.G., "The Vegetable & Herb Expert", 2003, pp. 47-49.

(Continued)

*Primary Examiner* — Weihua Fan

(74) *Attorney, Agent, or Firm* — Klarquist Sparkman, LLP

(57) ABSTRACT

A celery cultivar designated TBG 54 is disclosed. The invention relates to the seeds of celery cultivar TBG 54, to the plants of celery cultivar TBG 54, and to methods for producing a celery plant by crossing the cultivar TBG 54 with itself or another celery cultivar. The invention further relates to methods for producing a celery plant containing in its genetic material one or more transgenes and to the transgenic celery plants and plant parts produced by those methods. This invention also relates to celery cultivars or breeding cultivars and plant parts derived from celery cultivar TBG 54, to methods for producing other celery cultivars, lines or plant parts derived from celery cultivar TBG 54, and to the celery plants, varieties, and their parts derived from the use of those methods. The invention further relates to hybrid celery seeds, plants, and plant parts produced by crossing cultivar TBG 54 with another celery cultivar.

25 Claims, No Drawings

(56) References Cited

OTHER PUBLICATIONS

Jiang, G.L., "Molecular Markers and Marker-Assisted Breeding in Plants", Plant Breeding from Laboratories to Fields, InTech, 2013, pp. 45-83.

Kamburova, V.S., et al., "Genome Editing in Plants: An Overview of Tools and Applications", *Intl J. of Agronomy,* 2017, Article ID 7315351, 15 pages.

Kraft, T., Hansen, M., and Nilsson, N.O., "Linkage disequilibrium and fingerprinting in sugar beet", *Theor. Appl. Genet.,* 2000, 101:323-326.

Malzahn, A., et al., "Plant genome editing with TALEN and CRISPR", *Cell Biosci,* 2017, 7:21, 18 pages.

McCarthy, et al., 2001, Commercial celery production in eastern North Carolina, Horticulture Information Leaflet 27, NC State University.

Pang, S., et al., "Expression of a gene encoding a scorpion insectotoxin peptide in yeast, bacteria and plants", *Gene,* 1992, 116:165-172.

Quiros, et al., "Use of stem proteins and isozymes for the identification of celery varieties", *Plant Cell Reports,* 1987, 6:114-117.

U.S. Plant Variety Protection Cert. No. 200200021, issued Apr. 29, 2003, 36 pages.

U.S. Plant Variety Protection Cert. No. 200400326, issued Jun. 15, 2005, 16 pages.

U.S. Plant Variety Protection Certificate No. 9500019, issued Dec. 29, 1995, 25 pages.

U.S. Plant Variety Protection Certificate No. 9900063, issued Sep. 12, 2001, 19 pages.

Waycott, W. and Fort, S.B., "Differentiation of nearly identical germplasm accessions by a combination of molecular and morphologic analyses", *Genome,* 1994, 37(4):577-583.

* cited by examiner

CELERY CULTIVAR TBG 54

BACKGROUND OF THE INVENTION

The present invention relates to a new and distinctive celery (*Apium graveolens* var. *dulce*) variety designated TBG 54. All publications cited in this application are herein incorporated by reference.

There are numerous steps in the development of any novel, desirable plant germplasm. Plant breeding begins with the analysis, definition of problems and weaknesses of the current germplasm, the establishment of program goals, and the definition of specific breeding objectives. The next step is selection of germplasm that possesses the traits to meet the program goals. The goal is to combine in a single variety or hybrid an improved combination of desirable traits from the parental germplasm. These important traits may include improved flavor, increased stalk size and weight, higher seed yield, improved color, resistance to diseases and insects, tolerance to drought and heat, and better agronomic quality.

All cultivated forms of celery belong to the species *Apium graveolens* var. *dulce* that is grown for its edible stalk. As a crop, celery is grown commercially wherever environmental conditions permit the production of an economically viable yield. In the United States, the principal growing regions are California, Florida, Arizona, and Michigan. Fresh celery is available in the United States year-round, although the greatest supply is from November through January. For planting purposes, the celery season is typically divided into two seasons: summer and winter, with Florida and the southern California areas harvesting from November to July, and Michigan and northern California harvesting from July to October. Celery is consumed as fresh, raw product and as a cooked vegetable.

Celery is a cool-season biennial that grows best from 60° F. to 65° F. (16° C. to 18° C.) but will tolerate temperatures from 45° F. to 75° F. (7° C. to 24° C.). Freezing damages mature celery by splitting the petioles or causing the skin to peel, making the stalks unmarketable. This can be a problem for crops planted in the winter regions; however, celery can tolerate minor freezes early in the production cycle.

The two main growing regions for celery in California are located along the Pacific Ocean: the central coast or summer production area (Monterey, San Benito, Santa Cruz, and San Luis Obispo Counties) and the south coast or winter production area (Ventura and Santa Barbara Counties). A minor region (winter) is located in the southern deserts (Riverside and Imperial Counties).

In the south coast, celery is transplanted from early August to April for harvest from November to mid-July; in the Santa Maria area, celery is transplanted from January to August for harvest from April through December. In the central coast, fields are transplanted from March to September for harvest from late June to late December. In the southern deserts, fields are transplanted in late August for harvest in January.

Commonly used celery varieties for coastal production include Command, Mission, Conquistador and Sonora. Some shippers use their own proprietary varieties. Celery seed is very small and difficult to germinate. All commercial celery is planted as greenhouse-grown transplants. Celery grown from transplants is more uniform than from seed and takes less time to grow the crop in the field. Transplanted celery is traditionally placed in double rows on 40-inch (100-cm) beds with plants spaced between 6.0 and 7.0 inches apart.

Celery requires a relatively long and cool growing season (The physiology of vegetable crops by Pressman, CAB Intl., New York, 1997). Earlier transplanting results in a longer growing season, increased yields, and better prices. However, celery scheduled for spring harvest often involves production in the coolest weather conditions of winter, a period during which vernalization can occur. If adequate vernalization occurs for the variety, bolting may be initiated. Bolting is the premature rapid elongation of the main celery stem into a floral axis (i.e., during the first year for this normally biennial species). Bolting slows growth as the plant approaches marketable size and leaves a stalk with no commercial value. Different varieties have different vernalization requirements, but in the presence of bolting, the length of the seed stem can be used as a means of measuring bolting tolerance that exists in each different variety. The most susceptible varieties reach their vernalization requirement earlier and have time to develop the longest seed stems, while the moderately tolerant varieties take longer to reach their vernalization requirement and have less time to develop a seed stem which would therefore be shorter. Under normal production conditions, the most tolerant varieties may not achieve their vernalization requirement and therefore not produce a measurable seed stem.

The coldest months when celery is grown in the United States are December, January, and February. If celery is going to reach its vernalization requirements to cause bolting, it is generally younger celery that is exposed to this cold weather window. This celery generally matures in the months of April and May which constitute what the celery industry calls the bolting or seeder window. The bolting or seeder window is a period where seed stems are generally going to impact the quality of the marketable celery, and this is most consistently experienced in celery grown in the Southern California region. The presence of seed stems in celery can be considered a major marketable defect as set forth in the USDA grade standards. If the seed stem is longer than twice the diameter of the celery stalk or eight inches, the celery no longer meets the standards of US Grade #1. If the seed stem is longer than three times the diameter of the celery stalk, the celery is no longer marketable as US Grade #2 (*United States Standards for Grades of Celery*, United States Department of Agriculture, reprinted January 1997).

Celery is an allogamous biennial crop. The celery genome consists of 11 chromosomes. Its high degree of out-crossing is accomplished by insects and wind pollination. Pollinators of celery flowers include a large number of wasp, bee, and fly species. Celery is subject to inbreeding depression, which appears to be dependent upon the genetic background as some lines are able to withstand selfing for three or four generations.

Celery flowers are protandrous, with pollen being released 3-6 days before stigma receptivity. At the time of stigma receptivity, the stamens will have fallen, and the two *stigmata* will have unfolded in an upright position. The degree of protandry varies, which makes it difficult to perform reliable hybridization, due to the possibility of accidental selfing.

Celery flowers are very small, which significantly hinders easy removal of individual anthers. Furthermore, different developmental stages of the flowers in umbels make it difficult to avoid uncontrolled pollinations. The standard hybridization technique in celery consists of selecting flower buds of the same size and eliminating the older and younger flowers. Then, the umbellets are covered with glycine paper bags for a 5 to 10-day period, during which the stigmas become receptive. At the time the flowers are receptive, available pollen or umbellets shedding pollen from selected male parents are rubbed on to the stigmas of the female parent.

Celery plants require a period of vernalization while in the vegetative phase in order to induce seed stalk development. A period of 6-10 weeks at 5° C. to 8° C. when the plants are greater than 4 weeks old is usually adequate for most non-bolting tolerant varieties. Due to a wide range of responses to the cold treatment, it is often difficult to synchronize crossing, since plants will flower at different times. However, pollen can be stored for 6-8 months at −10° C. in the presence of silica gel or calcium chloride with a viability decline of only 20-40%, thus providing flexibility to perform crosses over a longer time.

For selfing, the plant or selected umbels are caged in cloth bags. These are shaken several times during the day to promote pollen release. Houseflies (*Musca domestica*) can also be introduced weekly into the bags to perform pollinations.

Celery in general is an important and valuable vegetable crop. Thus, a continuing goal of celery plant breeders is to develop stable, high yielding celery cultivars that are resistant to diseases and agronomically sound to maximize the amount of yield produced on the land. To accomplish this goal, the celery breeder must select and develop celery plants that have the traits that result in superior cultivars.

The foregoing examples of the related art and limitations related therewith are intended to be illustrative and not exclusive. Other limitations of the related art will become apparent to those of skill in the art upon a reading of the specification.

SUMMARY OF THE INVENTION

The following embodiments and aspects thereof are described in conjunction with systems, tools, and methods which are meant to be exemplary and illustrative, not limiting in scope. In various embodiments, one or more of the above-described problems have been reduced or eliminated, while other embodiments are directed to other improvements.

According to the invention, there is provided a novel celery cultivar designated TBG 54. Also provided are celery plants having the physiological and morphological characteristics of celery cultivar TBG 54. This invention thus relates to the seeds of celery cultivar TBG 54, to the plants of celery cultivar TBG 54, and to methods for producing a celery plant by crossing celery TBG 54 with itself or another celery plant, to methods for producing a celery plant containing in its genetic material one or more transgenes and to the transgenic celery plants produced by that method. This invention also relates to methods for producing other celery cultivars derived from celery cultivar TBG 54 and to the celery cultivar derived by the use of those methods. This invention further relates to hybrid celery seeds and plants produced by crossing celery cultivar TBG 54 with another celery line.

This invention further relates to the $F_1$ hybrid celery plants and plant parts grown from the hybrid seed produced by crossing celery cultivar TBG 54 to a second celery plant. Still further included in the invention are the seeds of an $F_1$ hybrid plant produced with the celery cultivar TBG 54 as one parent, the second generation ($F_2$) hybrid celery plant grown from the seed of the $F_1$ hybrid plant, and the seeds of the $F_2$ hybrid plant. Thus, any such methods using the celery cultivar TBG 54 are part of this invention: selfing, backcrosses, hybrid production, crosses to populations, and the like. All plants produced using celery cultivar TBG 54 as at least one parent are within the scope of this invention. Advantageously, the celery cultivar could be used in crosses with other, different, celery plants to produce first generation ($F_1$) celery hybrid seeds and plants with superior characteristics.

The invention further provides methods for developing celery plants derived from celery cultivar TBG 54 in a celery plant breeding program using plant breeding techniques including recurrent selection, backcrossing, pedigree breeding, restriction fragment length polymorphism enhanced selection, genetic marker enhanced selection and transformation. Seeds, celery plants, and parts thereof, produced by such breeding methods are also part of the invention.

In another aspect, the present invention provides protoplasts and regenerable cells for use in tissue culture of celery cultivar TBG 54. The tissue culture will preferably be capable of regenerating plants having essentially all of the physiological and morphological characteristics of the foregoing celery plant, and of regenerating plants having substantially the same genotype as the foregoing celery plant. Preferably, the regenerable cells in such tissue cultures will be callus, protoplasts, meristematic cells, leaves, pollen, embryos, roots, root tips, anthers, pistils, flowers, seeds, petioles, and suckers. Still further, the present invention provides celery plants regenerated from the tissue cultures of the invention.

In another aspect, the present invention provides for single or multiple gene converted plants of TBG 54. The single or multiple transferred gene(s) may preferably be a dominant or recessive allele. Preferably, the single or multiple transferred gene(s) will confer such traits as male sterility, herbicide resistance, insect resistance, modified fatty acid metabolism, modified carbohydrate metabolism, resistance for bacterial, fungal, or viral disease, male fertility, enhanced nutritional quality and industrial usage or the transferred gene will have no apparent value except for the purpose of being a marker for variety identification. The single or multiple gene(s) may be a naturally occurring celery gene or a transgene introduced through genetic engineering techniques.

The invention also relates to methods for producing a celery plant containing in its genetic material one or more transgenes and to the transgenic celery plant produced by those methods.

In another aspect, the present invention provides for methods of introducing one or more desired trait(s) into celery cultivar TBG 54 and plants or seeds obtained from such methods. The desired trait(s) may be, but not exclusively, a single gene, preferably a dominant but also a recessive allele. Preferably, the transferred gene or genes will confer such traits as male sterility, herbicide resistance, insect resistance, disease resistance, resistance for bacterial, fungal, or viral disease, male fertility, water stress tolerance, enhanced nutritional quality, modified fatty acid metabolism, modified carbohydrate metabolism, enhanced plant quality, and industrial usage. The gene or genes may be naturally occurring rice gene(s). The method for introducing the desired trait(s) may be a backcrossing process making use of a series of backcrosses to the celery cultivar TBG 54 during which the desired trait(s) is maintained by selection. The desired trait may also be introduced via transformation.

The invention further relates to methods for genetically modifying a celery plant of the celery cultivar TBG 54 and to the modified celery plant produced by those methods. The genetic modification methods may include, but are not limited to mutation, genome editing, gene silencing, RNA interference, backcross conversion, genetic transformation, single and multiple gene conversion, and/or direct gene transfer. The invention further relates to a genetically modified celery plant produced by the above methods, wherein the genetically modified celery plant comprises the genetic modification and otherwise comprises all of the physiological and morphological characteristics of celery cultivar TBG 54.

In addition to the exemplary aspects and embodiments described above, further aspects and embodiments will become apparent by reference by the study of the following descriptions.

DETAILED DESCRIPTION OF THE INVENTION

In the description and tables which follow, a number of terms are used. In order to provide a clear and consistent understanding of the specification and claims, including the scope to be given such terms, the following definitions are provided:

Allele. An allele is any of one or more alternative form of a gene, all of which relate to one trait or characteristic. In a diploid cell or organism, the two alleles of a given gene occupy corresponding loci on a pair of homologous chromosomes.

Backcrossing. Backcrossing is a process in which a breeder repeatedly crosses hybrid progeny back to one of the parents, for example, a first-generation hybrid $F_1$ with one of the parental genotype of the $F_1$ hybrid.

Bacterial blight. A bacterial disease of celery caused by *Pseudomonas syringae* pv. *apii*. The initial symptoms appear on the leaves as small, bright yellow, circular spots. As these enlarge with a yellow halo, they turn to a rust color. As the spots increase in number, they merge to eventually kill the leaf tissue. Bacterial blight is favored by cool, wet conditions and at least 10 hours of leaf wetness is required for infection. The disease is spread by water splashes, farm machinery and field workers especially when the foliage is wet.

Black streak. A physiological disorder in celery plants causing some petioles, when cut, to show "black streaks" in the lower half or throughout the entire length of the petiole, making the entire crop unmarketable. Symptoms can be triggered under field conditions by high temperatures.

Blackheart. Blackheart is due to a lack of movement of sufficient calcium that causes the plant to turn brown and begin to decay at the growing point of the plant. Celery in certain conditions, such as warm weather, grows very rapidly and is incapable of moving sufficient amounts of calcium to the growing point.

Bolting. The premature development of a flowering or seed stalk, and subsequent seed, before a plant produces a food crop. Bolting is typically caused by late planting when temperatures are low enough to cause vernalization of the plants.

Bolting period. Also known as the bolting or seeder window, and generally occurs in celery that is transplanted from the middle of December through January and matures in April to May. The intensity and actual weeks that bolting may be observed vary from year to year, but it is generally observed in this window.

Bolting tolerance. The amount of vernalization that is required for different celery varieties to bolt is genetically controlled. Varieties with increased tolerance to bolting require greater periods of vernalization in order to initiate bolting. A comparison of bolting tolerance between varieties can be measured by the length of the flowering or seed stem under similar vernalization conditions.

Brown stem. A disease caused by the bacterium *Pseudomonas cichorii* that causes petiole necrosis. Brown Stem is characterized by a firm, brown discoloration throughout the petiole.

Celeriac or Root celery (*Apium graveolens* L. var. *rapaceum*). A plant that is related to celery but instead of having a thickened and succulent leaf petiole as in celery, celeriac has an enlarged hypocotyl and upper root that is the edible product.

Celery heart. The center-most interior petioles and leaves of the celery stalk. They are not only the smallest petioles in the stalk, but the youngest as well. Some varieties are considered heartless because they go right from very large petioles to only a couple of very small petioles. The heart is comprised of the petioles that are closest to the meristem of the celery stalk.

*Colletotrichum*. One of the most common and important genera of plant-pathogenic fungi. Causes post-harvest rots, and anthracnose spots and blights of aerial plant parts. In celery it is also frequently accompanied by curling of the foliage and black heart. *Colletotrichum acutatum* sensu lato has been reclassified to be Colletotrichum fioriniae (Pavel, J. A., The Etiology, Virulence, and Phylogenetics of the Celery Anthracnose Pathogen, *Colletotrichum* fioriniae (=*C. acutatum* sensu lato), *Graduate Theses and Dissertations* (2016)).

Consumable. Means material that is edible by humans.

Crackstem. The petiole can crack or split horizontally or longitudinally. Numerous cracks in several locations along the petiole are often an indication that the variety has insufficient boron nutrition. A variety's ability to utilize boron is a physiological characteristic which is genetically controlled.

Essentially all of the physiological and morphological characteristics. A plant having essentially all of the physiological and morphological characteristics of a designated plant has all of the characteristics of the plant that are otherwise present when compared in the same environment, other than an occasional variant trait that might arise during backcrossing or direct introduction of a transgene.

$F_{\#}$. The "F" symbol denotes the filial generation, and the # is the generation number, such as $F_1$, $F_2$, $F_3$, etc.

$F_1$ hybrid. The first-generation progeny of the cross of two nonisogenic plants.

Feather leaf. Feather Leaf is a yellowing of the lower leaflets and generally occurs in the outer petioles but can also be found on inner petioles of the stalk. These yellowing leaves which would normally remain in the harvested stalk are considered unacceptable. These petioles then have to be stripped off in order to meet USDA standards which effectively decreases the stalk size and yield.

Flare. The lower, generally wider portion of the petiole which is usually a paler green or white. Some also refer to this as the spoon, scoop, or shovel.

*Fusarium* yellows. A fungal soilborne disease caused by *Fusarium oxysporum* f. sp. *apii* Race 2 and/or Race 4. Infected plants turn yellow and are stunted. Some of the large roots may have a dark brown and a water-soaked appearance. The water-conducting tissue (xylem) in the stem, crown, and root show a characteristic orange-brown discoloration. In the later stages of infection, plants remain severely stunted and yellowed and may collapse. The disease appears most severe during warm seasons, and in heavy, wet soils. Race 4 may also produce symptoms of black heart.

Gene. As used herein, "gene" refers to a segment of nucleic acid. A gene can be introduced into a genome of a species, whether from a different species or from the same species, using transformation or various breeding techniques.

Gene silencing. The interruption or suppression of the expression of a gene at the level of transcription or translation.

Genetically modified. Describes an organism that has received genetic material from another organism, or had its genetic material modified, resulting in a change in one or more of its phenotypic characteristics. Methods used to modify, introduce or delete the genetic material may include mutation breeding, genome editing, RNA interference, back-cross conversion, genetic transformation, single and multiple gene conversion, and/or direct gene transfer.

Genome editing. A type of genetic engineering in which DNA is inserted, replaced, modified, or removed from a genome using artificially engineered nucleases or other targeted changes using homologous recombination. Examples include but are not limited to use of zinc finger nucleases (ZFNs), TAL effector nucleases (TALENs), endonucleases, meganucleases, CRISPR/Cas9, and other CRISPR related technologies. (Ma et. al., *Molecular Plant,* 9:961-974 (2016); Belhaj et. al., *Current Opinion in Biotechnology,* 32:76-84 (2015)).

Gross yield (Pounds/Acre). The total yield in pounds/acre of trimmed celery plants (stalks).

Leaf celery (*Apium graveolens* L. var. *secalinum*). A plant that has been developed primarily for leaf and seed production. Often grown in Mediterranean climates, leaf celery more closely resembles celery's wild ancestors. The stems are small and fragile and vary from solid to hollow and the leaves are fairly small and are generally bitter. This type is often used for its medicinal properties and spice.

Leaf margin chlorosis. A magnesium deficiency producing an interveinal chlorosis which starts at the margin of leaves.

Maturity date. Maturity in celery can be dictated by two conditions. The first, or true maturity, is the point in time when the celery reaches maximum size distribution, but before defects such as pith, yellowing, Feather Leaf or Brown Stem appear. The second, or market maturity is an artificial maturity dictated by market conditions, i.e., the market requirement may be for 3 dozen sizes, so the field is harvested at slightly below maximum yield potential because the smaller sizes are what the customers prefer at that moment.

Muck. Muck is a soil made up primarily of humus drained from swampland. It is used for growing specialty crops, such as onions, carrots, celery, and potatoes.

MUN. MUN refers to the MUNSELL Color Chart which publishes an official color chart for plant tissues according to a defined numbering system. The chart may be purchased from the Macbeth Division of Kollmorgen Instruments Corporation, 617 Little Britain Road, New Windsor, New York 12553-6148.

Petiole. A petiole is the stem or limb of a leaf, the primary portion of the celery consumed.

Petiole depth. The average measurement in millimeters of the depth of the celery petiole at its narrowest point. The petiole depth measurement is taken from the outside of the petiole (which is the part of the petiole that faces the outside of the stalk) and is measured to the inside of the petiole or cup or the inner most point of the petiole that faces the center of the stalk or heart.

Petiole width. The average measurement of the width of the celery petiole in millimeters at its widest point. The measurement is taken from the side or edge of petiole to the opposite side or edge of the petiole. The measurement is taken 90 degrees from petiole depth.

Phthalides. One of the chemical compounds that are responsible for the characteristic flavor and aroma of celery.

Pith. Pith is a sponginess/hollowness/white discoloration that occurs in the petioles of celery varieties naturally as they become over-mature. In some varieties it occurs at an earlier stage causing harvest to occur prior to ideal maturity. Pith generally occurs in the outer, older petioles first. If it occurs, these petioles are stripped off to make grade, which effectively decreases the stalk size and overall yield potential.

Plant height. The height of the plant from the bottom of the base or butt of the celery plant to the top of the tallest leaf.

Polyphenol oxidase (PPO). An enzyme that catalyzes the conversion of phenolic compounds to quinones and assists their products' polymerization. The catalysis of PPO, in the presence of oxygen, leads to the formation of undesirable brown pigments and off-flavored products.

Quantitative Trait Loci. Quantitative Trait Loci (QTL) refers to genetic loci that control to some degree, numerically representable traits that are usually continuously distributed.

Regeneration. Regeneration refers to the development of a plant from tissue culture.

Ribbing. The texture of the exterior surface of the celery petiole can vary from smooth to ribby depending on the variety. Ribbing is the presence of numerous ridges that run vertically along the petioles of the celery plant.

Seed stem. A seed stem is the result of the elongation of the main stem of the celery, which is usually very compressed to almost non-existent, to form the flowering axis. The seed stem or flowering axis can reach several feet in height during full flower. The length of the seed stem is measured as the distance from the top of the basal plate (the base of the seed stem) to its terminus (the terminal growing point). *Septoria apiicola.* A fungus that is the cause of late blight in celery. Symptoms include chlorotic spots that turn brown and necrotic.

Single gene converted. Single gene converted or conversion plant refers to plants which are developed by backcrossing, or via genetic engineering, wherein essentially all of the desired morphological and physiological characteristics of a line are recovered in addition to the single gene transferred into the line via the backcrossing technique or via genetic engineering.

Stalk. A stalk is a single celery plant that is trimmed with the top or foliage and the roots removed.

Standard stem celery. A more traditional stem celery with moderate joint length, to be utilized and marketed as a whole stalk with 12 to 14 inch cut or for hearts in retail environment.

Stringiness. Stringiness is a physiological characteristic that is generally associated with strings that get stuck between the consumer's teeth. There are generally two sources of strings in celery. One is the vascular bundle which can be fairly elastic and behave as a string. The second is a strip of particularly strong epidermis cells called schlerenchyma which are located on the surface of the ridges of the celery varieties that have ribs.

Suckers. Suckers are auxiliary shoots that form at the base of the stalk or within the auxiliary buds between each petiole. If these shoots form between the petioles of the stalk, several petioles have to be stripped off causing the celery to become smaller and the functional yields to be decreased.

Tall stem celery. A stem celery with especially long petioles with primary purpose of being utilized for production of sticks or limbs.

Transgene. A nucleic acid of interest that can be introduced into the genome of a plant by genetic engineering techniques (e.g., transformation) or breeding.

Celery cultivar TBG 54 is a new celery cultivar that has shown excellent potential for production in Belle Glade, Florida on the Glades sedge-based mucks. Celery cultivar TBG 54 has characteristics that allow it to have production advantages through all Florida production seasons. Tolerance to diseases, particularly *Cercospora apii*, and tolerance to stress allow TBG 54 to be produced in the fall hurricane season when moisture and nutrition issues can be challenging (excess rain from hurricanes causes flooding, enhances disease issues and leaches fertility) and in the spring when *Cercospora apii* can be more problematic due to increased rain conditions and bolting can be more challenging due to occasional colder Florida winters.

Celery cultivar TBG 54 is more similar to its sister TBG 31 for its ability for production in Florida fall season (hurricane season) with early winter harvest. However, TBG 54 differentiates itself by having improved tolerances for bolting and generally improved yield.

Celery cultivar TBG 54 has the following morphologic and other characteristics (based primarily on data collected in Florida):

Table 1

Variety Description Information

Celery cultivar TBG 54 is the result of 7 generations of single seed descent from a selection of a cross made between Tall Utah 52-75 (which is commercially available, for example from Pybas Seed Co.) and an unnamed proprietary breeding parent internally designated as 11-7. Main traits that were originally selected for include field holding and yield. A detailed description of the variety follows.

Maturity: 86-96 days in Belle Glade, Florida
Plant height: 73.8 cm
Number of outer petioles (>35.6 cm): 13.0
Number of inner petioles (<35.6 cm): 5.8
Stalk shape: Cylindrical
Stalk conformation: Fairly compact
Heart formation: Moderate to full heart
Petiole length (from butt to first joint): 30.4 cm
Petiole width (at petiole midpoint): 21.6 mm
Petiole thickness (at petiole midpoint): 10.4 mm
Petiole cross section shape: Cup to deep cup
Petiole color (un-blanched at harvest): MUN 5gy 7/8
Anthocyanin: Absent
Stringiness: Very slight
Ribbing: Smooth to slight rib
Glossiness: Glossy
Leaf blade color: MUN 5gy 4/6
Bolting tolerance: Fairly tolerant for Florida conditions
Stress Tolerance:
Adaxial crackstem (boron deficiency): Tolerant
Abaxial crackstem (boron deficiency): Tolerant
Leaf margin chlorosis (magnesium deficiency): Tolerant
Blackheart (calcium deficiency): Tolerant
Pithiness (nutritional deficiency): Moderately tolerant
Feather leaf: Moderately tolerant Sucker development: Tolerant
Disease Resistance:
Brown stem (*Pseudomonas cichorii*): Tolerant
Bacterial blight (*Pseudomonas syringae* PV. *apii*): Unknown
Early blight (*Cercospora apii*): Moderately tolerant
Late blight (*Septoria apiicola*): Susceptible
*Colletotrichum fioriniae*: Moderately susceptible
*Fusarium oxysporum* f. sp. *apii* race 2: Susceptible
*Fusarium oxysporum* f. sp. *apii* race 4: Susceptible This invention is also directed to methods for producing a celery plant by crossing a first parent celery plant with a second parent celery plant, wherein the first parent celery plant or second parent celery plant is celery cultivar TBG 54. Further, both the first parent celery plant and second parent celery plant may be from celery cultivar TBG 54. Still further, this invention also is directed to methods for producing a cultivar TBG 54-derived celery plant by crossing cultivar TBG 54 with a second celery plant and growing the progeny seed and repeating the crossing and growing steps with the cultivar TBG 54-derived plant from 0 to 7 times. Thus, any such methods using the cultivar TBG 54 are part of this invention: selfing, backcrosses, hybrid production, crosses to populations, and the like. All plants produced using cultivar TBG 54 as a parent are within the scope of this invention, including plants derived from cultivar TBG 54. Advantageously, cultivar TBG 54 can be used in crosses with other, different cultivars to produce first generation (F1) celery seeds and plants with superior characteristics.

Additional methods include, but are not limited to, expression vectors introduced into plant tissues using a direct gene transfer method such as microprojectile-mediated delivery, DNA injection, electroporation and the like. More preferably, expression vectors are introduced into plant tissues by using either microprojectile-mediated delivery with a biolistic device or by using *Agrobacterium*-mediated transformation. Transformant plants obtained with the protoplasm of the invention are intended to be within the scope of this invention.

As used herein, the term "plant" includes plant cells, plant protoplasts, plant cell tissue cultures from which celery plants can be regenerated, plant calli, plant clumps and plant cells that are intact in plants or parts of plants, such as leaves, pollen, embryos, meristematic cells, hypocotyls, roots, root tips, anthers, pistils, flowers, seeds, stems, and the like.

Further Embodiments of the Invention

Celery in general is an important and valuable vegetable crop. Thus, a continuing goal of celery plant breeders is to develop stable, high yielding celery cultivars that are agronomically sound. To accomplish this goal, the celery breeder must select and develop celery plants with traits that result in superior cultivars.

Plant breeding techniques known in the art and used in a celery plant breeding program include, but are not limited to, pedigree breeding, recurrent selection, mass selection, single or multiple-seed descent, bulk selection, backcrossing, open pollination breeding, restriction fragment length polymorphism enhanced selection, genetic marker enhanced selection, making double haploids, and transformation. Often combinations of these techniques are used. The development of celery varieties in a plant breeding program requires, in general, the development and evaluation of homozygous varieties. There are many analytical methods available to evaluate a new variety. The oldest and most traditional method of analysis is the observation of phenotypic traits, but genotypic analysis may also be used.

Using Celery Cultivar TBG 54 to Develop Other Celery Varieties

This invention also is directed to methods for producing a celery plant by crossing a first parent celery plant with a second parent celery plant wherein the first or second parent celery plant is a celery plant of cultivar TBG 54. Further, both first and second parent celery plants can come from celery cultivar TBG 54. Also provided are methods for producing a celery plant having substantially all of the morphological and physiological characteristics of cultivar TBG 54, by crossing a first parent celery plant with a second parent celery plant wherein the first and/or the second parent celery plant is a plant having substantially all of the morphological and physiological characteristics of cultivar TBG 54 as determined at the 5% significance level when grown in the same environmental conditions. The other parent may be any celery plant, such as a celery plant that is part of a synthetic or natural population. Thus, any such methods using celery cultivar TBG 54 are part of this invention: selfing, backcrosses, hybrid production, crosses to populations, and the like. All plants produced using celery cultivar TBG 54 as at least one parent are within the scope of this invention, including those developed from cultivars derived from celery cultivar TBG 54.

The cultivar of the invention can also be used for transformation where exogenous genes are introduced and expressed by the cultivar of the invention. Genetic variants created either through traditional breeding methods using celery cultivar TBG 54 or through transformation of cultivar TBG 54 by any of a number of protocols known to those of skill in the art are intended to be within the scope of this invention.

The following describes breeding methods that may be used with celery cultivar TBG 54 in the development of further celery plants. One such embodiment is a method for developing a progeny celery plant in a celery plant breeding program comprising: obtaining the celery plant, or a part thereof, of cultivar TBG 54, utilizing said plant or plant part as a source of breeding material, and selecting a celery cultivar TBG 54 progeny plant with molecular markers in common with cultivar TBG 54 and/or with morphological and/or physiological characteristics of celery cultivar TBG 54. Breeding steps that may be used in the celery plant breeding program include, but are not limited to, pedigree breeding, backcrossing, mutation breeding, and recurrent selection. In conjunction with these steps, techniques such as RFLP-enhanced selection, genetic marker enhanced selection (for example SSR markers) and the making of double haploids may be utilized.

Another method involves producing a population of celery cultivar TBG 54 progeny celery plants, comprising crossing cultivar TBG 54 with another celery plant, thereby producing a population of celery plants, which, on average, derive 50% of their alleles from celery cultivar TBG 54. A plant of this population may be selected and repeatedly selfed or sibbed with a celery cultivar resulting from these successive filial generations. One embodiment of this invention is the celery cultivar produced by this method and that has obtained at least 50% of its alleles from celery cultivar TBG 54.

Still yet another aspect of the invention is a method of producing a celery plant derived from the celery cultivar TBG 54, the method comprising the steps of: (a) preparing a progeny plant derived from celery cultivar TBG 54 by crossing a plant of the celery cultivar TBG 54 with a second celery plant; and (b) crossing the progeny plant with itself or a second plant to produce a seed of a progeny plant of a subsequent generation which is derived from a plant of the celery cultivar TBG 54. In further embodiments of the invention, the method may additionally comprise: (c) growing a progeny plant of a subsequent generation from said seed of a progeny plant of a subsequent generation and crossing the progeny plant of a subsequent generation with itself or a second plant; and repeating the steps for an additional 2-10 generations to produce a celery plant derived from the celery cultivar TBG 54. The plant derived from celery cultivar TBG 54 may be an inbred line, and the aforementioned repeated crossing steps may be defined as comprising sufficient inbreeding to produce the inbred line. In the method, it may be desirable to select particular plants resulting from step (c) for continued crossing according to steps (b) and (c). By selecting plants having one or more desirable traits, a plant derived from celery cultivar TBG 54 is obtained which possesses some of the desirable traits of the line as well as potentially other selected traits. Also provided by the invention is a plant produced by this and the other methods of the invention.

In another embodiment of the invention, the method of producing a celery plant derived from the celery cultivar TBG 54 further comprises: (a) crossing the celery cultivar TBG 54-derived celery plant with itself or another celery plant to yield additional celery cultivar TBG 54-derived progeny celery seed; (b) growing the progeny celery seed of step (a) under plant growth conditions to yield additional celery cultivar TBG 54-derived celery plants; and (c) repeating the crossing and growing steps of (a) and (b) to generate further celery cultivar TBG 54-derived celery plants. In specific embodiments, steps (a) and (b) may be repeated at least 1, 2, 3, 4, or 5 or more times as desired. The invention still further provides a celery plant produced by this and the foregoing methods.

Progeny of celery cultivar TBG 54 may also be characterized through their filial relationship with celery cultivar TBG 54, as for example, being within a certain number of breeding crosses of celery cultivar TBG 54. A breeding cross is a cross made to introduce new genetics into the progeny, and is distinguished from a cross, such as a self or a sib cross, made to select among existing genetic alleles. The lower the number of breeding crosses in the pedigree, the closer the relationship between celery cultivar TBG 54 and its progeny. For example, progeny produced by the methods described herein may be within 1, 2, 3, 4 or 5 breeding crosses of celery cultivar TBG 54.

One of ordinary skill in the art of plant breeding would know how to evaluate the traits of two plant varieties to determine if there is no significant difference between the two traits expressed by those varieties. For example, see, Fehr and Walt, *Principles of Cultivar Development*, pp. 261-286 (1987). Thus the invention includes celery cultivar TBG 54 progeny celery plants comprising a combination of at least two cultivar TBG 54 traits selected from the group consisting of those listed in Table 1 or the cultivar TBG 54 combination of traits listed in the Detailed Description of the Invention, so that said progeny celery plant is not significantly different for said traits than celery cultivar TBG 54 as determined at the 5% significance level when grown in the same environmental conditions. Using techniques described herein, molecular markers may be used to identify said progeny plant as a celery cultivar TBG 54 progeny plant. Mean trait values may be used to determine whether trait differences are significant, and preferably the traits are measured on plants grown under the same environmental conditions. Once such a variety is developed its value is substantial since it is important to advance the germplasm base as a whole in order to maintain or improve traits such as yield, disease resistance, pest resistance, and plant performance in extreme environmental conditions.

The goal of celery plant breeding is to develop new, unique, and superior celery cultivars. The breeder initially selects and crosses two or more parental lines, followed by repeated selfing and selection, producing many new genetic combinations. The breeder can theoretically generate billions of different genetic combinations via crossing, selfing, and mutations. The breeder has no direct control at the cellular level and the cultivars that are developed are unpredictable. This unpredictability is because the breeder's selection occurs in unique environments, with no control at the DNA level (using conventional breeding procedures), and with millions of different possible genetic combinations being generated. A breeder of ordinary skill in the art cannot predict the final resulting lines he develops, except possibly in a very gross and general fashion. The same breeder cannot produce the same line twice by using the exact same original parents and the same selection techniques. Therefore, two breeders will never develop the same line, or even very similar lines, having the same celery traits.

Pedigree breeding is used commonly for the improvement of self-pollinating crops or inbred lines of cross-pollinating crops. Pedigree breeding starts with the crossing of two genotypes, such as celery cultivar TBG 54 or a celery variety having all of the morphological and physiological characteristics of TBG 54, and another celery variety having one or more desirable characteristics that is lacking or which complements celery cultivar TBG 54. If the two original parents do not provide all the desired characteristics, other sources can be included in the breeding population. In the pedigree method, superior plants are selfed and selected in successive filial generations. In the succeeding filial generations, the heterozygous condition gives way to the homozygous allele condition as a result of inbreeding. Typically, in the pedigree method of breeding, five or more successive filial generations of selfing and selection is practiced: $F_1$ to $F_2$; $F_2$ to $F_3$; $F_3$ to $F_4$; $F_4$ to $F_5$; etc. In some examples, 1, 2, 3, 4, 5, 6, 7, 8, 9, 10, or more generations of selfing and selection are practiced. After a sufficient amount of inbreeding, successive filial generations will serve to increase seed of the developed variety. Preferably, the developed variety comprises homozygous alleles at about 95% or more of its loci.

In addition to being used to create backcross conversion populations, backcrossing can also be used in combination with pedigree breeding. As discussed previously, backcrossing can be used to transfer one or more specifically desirable traits from one variety (the donor parent) to a developed variety (the recurrent parent), which has good overall agronomic characteristics yet may lack one or more other desirable traits. However, the same procedure can be used to move the progeny toward the genotype of the recurrent parent but at the same time retain many components of the non-recurrent parent by stopping the backcrossing at an early stage and proceeding with selfing and selection. For example, a celery variety may be crossed with another variety to produce a first-generation progeny plant. The first-generation progeny plant may then be backcrossed to one of its parent varieties to create a $F_1BC_1$. Progeny are selfed and selected so that the newly developed variety has many of the attributes of the recurrent parent and yet several of the desired attributes of the donor parent. This approach leverages the value and strengths of both parents for use in new celery varieties.

Therefore, in some examples a method of making a backcross conversion of celery cultivar TBG 54, comprising the steps of crossing a plant of celery cultivar TBG 54 or a celery variety having all of the morphological and physiological characteristics of TBG 54 with a donor plant possessing a desired trait to introduce the desired trait, selecting an $F_1$ progeny plant containing the desired trait, and backcrossing the selected $F_1$ progeny plant to a plant of celery cultivar TBG 54 are provided. This method may further comprise the step of obtaining a molecular marker profile of celery cultivar TBG 54 and using the molecular marker profile to select for a progeny plant with the desired trait and the molecular marker profile of TBG 54. The molecular marker profile can comprise information from one or more markers. In one example the desired trait is a mutant gene or transgene present in the donor parent. In another example, the desired trait is a native trait in the donor parent.

Mass and recurrent selections can be used to improve populations of either self- or cross-pollinating crops. A genetically variable population of heterozygous individuals is either identified or created by intercrossing several different parents. The best plants are selected based on individual superiority, outstanding progeny, or excellent combining ability. The selected plants are intercrossed to produce a new population in which further cycles of selection are continued.

The single-seed descent procedure in the strict sense refers to planting a segregating population, harvesting a sample of one seed per plant, and using the one-seed sample to plant the next generation. When the population has been advanced from the $F_2$ to the desired level of inbreeding, the plants from which lines are derived will each trace to different $F_2$ individuals. The number of plants in a population declines each generation due to failure of some seeds to germinate or some plants to produce at least one seed. As a result, not all of the $F_2$ plants originally sampled in the population, will be represented by a progeny when generation advance is completed.

Mutation breeding is another method of introducing new traits into celery varieties. Mutations that occur spontaneously or are artificially induced can be useful sources of variability for a plant breeder. The goal of artificial mutagenesis is to increase the rate of mutation for a desired characteristic. Mutation rates can be increased by many different means including temperature, long-term seed storage, tissue culture conditions, radiation (such as X-rays, Gamma rays, neutrons, Beta radiation, or ultraviolet radiation), chemical mutagens (such as base analogs like 5-bromo-uracil), antibiotics, alkylating agents (such as sulfur mustards, nitrogen mustards, epoxides, ethyleneamines, sulfates, sulfonates, sulfones, or lactones), azide, hydroxylamine, nitrous acid or acridines. Once a desired trait is observed through mutagenesis the trait may then be incorporated into existing germplasm by traditional breeding techniques. Details of mutation breeding can be found in "Principles of Cultivar Development" by Fehr, Macmillan Publishing Company, 1993. In addition, mutations created in other celery plants may be used to produce a backcross conversion of celery cultivar TBG 54 that comprises such mutation.

Selection of celery plants for breeding is not necessarily dependent on the phenotype of a plant and instead can be based on genetic investigations. For example, one may utilize a suitable genetic marker which is closely associated with a trait of interest. One of these markers may therefore be used to identify the presence or absence of a trait in the offspring of a particular cross, and hence may be used in selection of progeny for continued breeding. This technique may commonly be referred to as marker-assisted selection. Any other type of genetic marker or other assay which is able to identify the relative presence or absence of a trait of interest in a plant may also be useful for breeding purposes. Procedures for marker assisted selection applicable to the breeding of celeries are well known in the art. Such methods will be of particular utility in the case of recessive traits and variable phenotypes, or where conventional assays may be more expensive, time consuming or otherwise disadvantageous. Types of genetic markers which could be used in accordance with the invention include, but are not necessarily limited to, Isozyme Electrophoresis, Restriction Fragment Length Polymorphisms (RFLPs), Simple Sequence Length Polymorphisms (SSLPs) (Williams et al., Nucleic Acids Res., 18:6531-6535, 1990), Randomly Amplified Polymorphic DNAs (RAPDs), DNA Amplification Fingerprinting (DAF), Sequence Characterized Amplified Regions (SCARs), Arbitrary Primed Polymerase Chain Reaction (AP-PCR), Amplified Fragment Length Polymorphisms (AFLPs) (EP 534 858, specifically incorporated herein by reference in its entirety), Simple Sequence Repeats (SSRs), and Single Nucleotide Polymorphisms (SNPs) (Wang et al., Science, 280:1077-1082, 1998).

The production of double haploids can also be used for the development of homozygous varieties in a breeding program. Double haploids are produced by the doubling of a set of chromosomes from a heterozygous plant to produce a completely homozygous individual. For example, see, Wan, et al., "Efficient Production of Doubled Haploid Plants Through Colchicine Treatment of Anther-Derived Maize Callus," *Theoretical and Applied Genetics*, 77:889-892 (1989) and U.S. Pat. No. 7,135,615. This can be advantageous because the process omits the generations of selfing needed to obtain a homozygous plant from a heterozygous source.

Descriptions of other breeding methods that are commonly used for different traits and crops can be found in one of several reference books (e.g., Allard, "Principles of plant breeding," John Wiley & Sons, NY, University of California, Davis, Calif, 50-98, 1960; Simmonds, "Principles of crop improvement," Longman, Inc., NY, 369-399, 1979; Sneep and Hendriksen, "Plant breeding perspectives," Wageningen (ed), Center for Agricultural Publishing and Documentation, 1979; Fehr, In: Soybeans: Improvement, Production and Uses," 2d Ed., Manograph 16:249, 1987; Fehr, "Principles of cultivar development," Theory and Technique (Vol 1) and Crop Species Soybean (Vol 2), Iowa State Univ., Macmillian Pub. Co., NY, 360-376, 1987; Poehlman and Sleper, "Breeding Field Crops" Iowa State University Press, Ames, 1995; Sprague and Dudley, eds., Corn and Improvement, 5th ed., 2006).

Genotypic Profile of TBG 54 and Progeny

In addition to phenotypic observations, a plant can also be identified by its genotype. The genotype of a plant can be characterized through a genetic marker profile which can identify plants of the same variety or a related variety, or which can be used to determine or validate a pedigree. Genetic marker profiles can be obtained by techniques such as restriction fragment length polymorphisms (RFLPs), randomly amplified polymorphic DNAs (RAPDs), arbitrarily primed polymerase chain reaction (AP-PCR), DNA amplification fingerprinting (DAF), sequence characterized amplified regions (SCARs), amplified fragment length polymorphisms (AFLPs), simple sequence repeats (SSRs) also referred to as microsatellites, single nucleotide polymorphisms (SNPs), or genome-wide evaluations such as genotyping-by-sequencing (GBS). For example, see Cregan et al. (1999) "An Integrated Genetic Linkage Map of the Soybean Genome" Crop Science 39:1464-1490, and Berry et al. (2003) "Assessing Probability of Ancestry Using Simple Sequence Repeat Profiles: Applications to Maize Inbred Lines and Soybean Varieties" Genetics 165:331-342, each of which are incorporated by reference herein in their entirety. Favorable genotypes and or marker profiles, optionally associated with a trait of interest, may be identified by one or more methodologies.

In some examples one or more markers are used, including but not limited to AFLPs, RFLPs, ASH, SSRs, SNPs, indels, padlock probes, molecular inversion probes, microarrays, sequencing, and the like. In some methods, a target nucleic acid is amplified prior to hybridization with a probe. In other cases, the target nucleic acid is not amplified prior to hybridization, such as methods using molecular inversion probes (see, for example Hardenbol et al. (2003) *Nat Biotech* 21:673-678). In some examples, the genotype related to a specific trait is monitored, while in other examples, a genome-wide evaluation including but not limited to one or more of marker panels, library screens, association studies, microarrays, gene chips, expression studies, or sequencing such as whole-genome resequencing and genotyping-by-sequencing (GBS) may be used. In some examples, no target-specific probe is needed, for example by using sequencing technologies, including but not limited to next-generation sequencing methods (see, for example, Metzker (2010) *Nat Rev Genet* 11:31-46; and, Egan et al. (2012) *Am J Bot* 99:175-185) such as sequencing by synthesis (e.g., Roche 454 pyrosequencing, Illumina Genome Analyzer, and Ion Torrent PGM or Proton systems), sequencing by ligation (e.g., SOLiD from Applied Biosystems, and Polnator system from Azco Biotech), and single molecule sequencing (SMS or third-generation sequencing) which eliminate template amplification (e.g., Helicos system, and PacBio RS system from Pacific BioSciences). Further technologies include optical sequencing systems (e.g., Starlight from Life Technologies), and nanopore sequencing (e.g., GridION from Oxford Nanopore Technologies). Each of these may be coupled with one or more enrichment strategies for organellar or nuclear genomes in order to reduce the complexity of the genome under investigation via PCR, hybridization, restriction enzyme (see, e.g., Elshire et al. (2011) *PLoS ONE* 6:e19379), and expression methods. In some examples, no reference genome sequence is needed in order to complete the analysis.

With any of the genotyping techniques mentioned herein, polymorphisms may be detected when the genotype and/or sequence of the plant of interest is compared to the genotype and/or sequence of one or more reference plants. The polymorphism revealed by these techniques may be used to establish links between genotype and phenotype. The polymorphisms may thus be used to predict or identify certain phenotypic characteristics, individuals, or even species. The polymorphisms are generally called markers. It is common practice for the skilled artisan to apply molecular DNA techniques for generating polymorphisms and creating markers. The polymorphisms of this invention may be provided in a variety of mediums to facilitate use, e.g. a database or computer readable medium, which may also contain descriptive annotations in a form that allows a skilled artisan to examine or query the polymorphisms and obtain useful information.

The invention further provides a method of determining the genotype of a plant of celery cultivar TBG 54, or a first-generation progeny thereof, comprising detecting in the genome of the plant at least a first polymorphism. The method may, in certain embodiments, comprise detecting a plurality of polymorphisms in the genome of the plant. The method may further comprise storing the results of the step of detecting the plurality of polymorphisms on a computer readable medium. The plurality of polymorphisms are indicative of and/or give rise to the expression of the morphological and physiological characteristics of celery cultivar TBG 54. The invention further provides a computer readable medium produced by such a method.

In some examples, a plant, a plant part, or a seed of celery cultivar TBG 54 may be characterized by producing a molecular profile. A molecular profile may include, but is not limited to, one or more genotypic and/or phenotypic profile(s). A genotypic profile may include, but is not limited to, a marker profile, such as a genetic map, a linkage map, a trait maker profile, a SNP profile, an SSR profile, a genome-wide marker profile, a haplotype, and the like. A molecular profile may also be a nucleic acid sequence profile, and/or a physical map. A phenotypic profile may include, but is not limited to, a protein expression profile, a metabolic profile, an mRNA expression profile, and the like.

SSR technology is currently the most efficient and practical marker technology; more marker loci can be routinely used and more alleles per marker locus can be found using SSRs in comparison to RFLPs. For example, Diwan and Cregan described a highly polymorphic microsatellite locus in soybean with as many as 26 alleles. Diwan, N. and Cregan, P. B., *Theor. Appl. Genet.,* 95:22-225 (1997). SNPs may also be used to identify the unique genetic composition of the invention and progeny varieties retaining that unique genetic composition. Various molecular marker techniques may be used in combination to enhance overall resolution.

Molecular markers, which include markers identified through the use of techniques such as Isozyme Electrophoresis, RFLPs, RAPDs, AP-PCR, DAF, SCARs, AFLPs, SSRs, and SNPs, may be used in plant breeding. One use of molecular markers is Quantitative Trait Loci (QTL) mapping. QTL mapping is the use of markers which are known to be closely linked to alleles that have measurable effects on a quantitative trait. Selection in the breeding process is based upon the accumulation of markers linked to the positive effecting alleles and/or the elimination of the markers linked to the negative effecting alleles from the plant's genome.

Molecular markers can also be used during the breeding process for the selection of qualitative traits. For example, markers closely linked to alleles or markers containing sequences within the actual alleles of interest can be used to select plants that contain the alleles of interest during a backcrossing breeding program. The markers can also be used to select toward the genome of the recurrent parent and against the markers of the donor parent. This procedure attempts to minimize the amount of genome from the donor parent that remains in the selected plants. It can also be used to reduce the number of crosses back to the recurrent parent needed in a backcrossing program. The use of molecular markers in the selection process is often called genetic marker enhanced selection or marker-assisted selection. Molecular markers may also be used to identify and exclude certain sources of germplasm as parental varieties or ancestors of a plant by providing a means of tracking genetic profiles through crosses.

Particular markers used for these purposes are not limited to the set of markers disclosed herein but may include any type of marker and marker profile which provides a means of distinguishing varieties. In addition to being used for identification of celery cultivar TBG 54, a hybrid produced through the use of TBG 54, and the identification or verification of pedigree for progeny plants produced through the use of TBG 54, a genetic marker profile is also useful in developing a gene conversion of TBG 54.

Means of performing genetic marker profiles using SNP and SSR polymorphisms are well known in the art. SNPs are genetic markers based on a polymorphism in a single nucleotide. A marker system based on SNPs can be highly informative in linkage analysis relative to other marker systems in that multiple alleles may be present.

The SSR profile of celery cultivar TBG 54 can be used to identify plants comprising celery cultivar TBG 54 as a parent, since such plants will comprise the same homozygous alleles as celery cultivar TBG 54. Because the celery variety is essentially homozygous at all relevant loci, most loci should have only one type of allele present. In contrast, a genetic marker profile of an $F_1$ progeny should be the sum of those parents, e.g., if one parent was homozygous for allele x at a particular locus, and the other parent homozygous for allele y at that locus, then the $F_1$ progeny will be xy (heterozygous) at that locus. Subsequent generations of progeny produced by selection and breeding are expected to be of genotype x (homozygous), y (homozygous), or xy (heterozygous) for that locus position. When the $F_1$ plant is selfed or sibbed for successive filial generations, the locus should be either x or y for that position.

In addition, plants and plant parts substantially benefiting from the use of celery cultivar TBG 54 in their development, such as celery cultivar TBG 54 comprising a gene conversion, backcross conversion, transgene, or genetic sterility factor, may be identified by having a molecular marker profile with a high percent identity to celery cultivar TBG 54. Such a percent identity might be 95%, 96%, 97%, 98%, 99%, 99.5%, or 99.9% identical to celery cultivar TBG 54.

The SSR profile of celery cultivar TBG 54 can also be used to identify essentially derived varieties and other progeny varieties developed from the use of celery cultivar TBG 54, as well as cells and other plant parts thereof. Such plants may be developed using the markers identified in WO 00/31964, U.S. Pat. Nos. 6,162,967, and 7,288,386. Progeny plants and plant parts produced using celery cultivar TBG 54 may be identified by having a molecular marker profile of at least 25%, 30%, 35%, 40%, 45%, 50%, 55%, 60%, 65%, 70%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 99.5% genetic contribution from celery cultivar TBG 54, as measured by either percent identity or percent similarity. Such progeny may be further characterized as being within a pedigree distance of celery cultivar TBG 54, such as within 1, 2, 3, 4, or 5 or less cross-pollinations to a celery plant other than celery cultivar TBG 54 or a plant that has celery cultivar TBG 54 as a progenitor. Unique molecular profiles may be identified with other molecular tools such as SNPs and RFLPs.

While determining the genotypic profile of the plants described supra, several unique SSR profiles may also be identified which did not appear in either parent of such plant. Such unique SSR profiles may arise during the breeding process from recombination or mutation. A combination of several unique alleles provides a means of identifying a plant variety, an $F_1$ progeny produced from such variety, and progeny produced from such variety.

Molecular data from TBG 54 may be used in a plant breeding process. Nucleic acids may be isolated from a seed of TBG 54 or from a plant, plant part, or cell produced by growing a seed of TBG 54, or from a seed of TBG 54 with a gene conversion, or from a plant, plant part, or cell of TBG 54 with a gene conversion. One or more polymorphisms may be isolated from the nucleic acids. A plant having one or more of the identified polymorphisms may be selected and used in a plant breeding method to produce another plant.

In another embodiment of the invention, the genetic complement of the celery cultivar TBG 54 is provided. The phrase "genetic complement" is used to refer to the aggregate of nucleotide sequences, the expression of which sequences defines the phenotype of, in the present case, a celery plant, or a cell or tissue of that plant. A genetic complement thus represents the genetic makeup of a cell, tissue or plant, and a hybrid genetic complement represents the genetic makeup of a hybrid cell, tissue or plant. The invention thus provides celery plant cells that have a genetic complement in accordance with the celery plant cells disclosed herein, and plants, seeds and plants containing such cells. Plant genetic complements may be assessed by genetic marker profiles, and by the expression of phenotypic traits that are characteristic of the expression of the genetic complement, e.g., isozyme typing profiles.

Introduction of a New Trait or Locus into Celery Cultivar TBG 54

Cultivar TBG 54 represents a new base genetic variety into which a new gene, locus or trait may be introgressed. Backcrossing and direct transformation represent two important methods that can be used to accomplish such an introgression.

Single Gene (Locus) Conversions

When the term "celery plant" is used in the context of the present invention, this also includes any single gene or locus conversions of that variety. The term "single locus converted plant" or "single gene converted plant" refers to those celery plants which are developed by backcrossing or genetic engineering, wherein essentially all of the desired morphological and physiological characteristics of a variety are recovered in addition to the one or more genes transferred into the variety via the backcrossing technique or genetic engineering. Backcrossing methods can be used with the present invention to improve or introduce a characteristic into the variety.

A backcross conversion of celery cultivar TBG 54 occurs when DNA sequences are introduced through backcrossing (Hallauer, et al., "Corn Breeding," Corn and Corn Improvements, No. 18, pp. 463-481 (1988)), with celery cultivar TBG 54 utilized as the recurrent parent. Both naturally occurring and transgenic DNA sequences may be introduced through backcrossing techniques. A backcross conversion may produce a plant with a trait or locus conversion in at least two or more backcrosses, including at least 2 crosses, at least 3 crosses, at least 4 crosses, at least 5 crosses, and the like. Molecular marker assisted breeding or selection may be utilized to reduce the number of backcrosses necessary to achieve the backcross conversion. For example, see, Openshaw, S. J., et al., Marker-assisted Selection in Backcross Breeding, Proceedings Symposium of the Analysis of Molecular Data, Crop Science Society of America, Corvallis, Oregon (August 1994), where it is demonstrated that a backcross conversion can be made in as few as two backcrosses.

The complexity of the backcross conversion method depends on the type of trait being transferred (single genes or closely linked genes as compared to unlinked genes), the level of expression of the trait, the type of inheritance (cytoplasmic or nuclear), and the types of parents included in the cross. It is understood by those of ordinary skill in the art that for single gene traits that are relatively easy to classify, the backcross method is effective and relatively easy to manage. (See, Hallauer, et al., Corn and Corn Improvement, Sprague and Dudley, Third Ed. (1998)). Desired traits that may be transferred through backcross conversion include, but are not limited to, sterility (nuclear and cytoplasmic), fertility restoration, nutritional enhancements, drought tolerance, nitrogen utilization, altered fatty acid profile, modified fatty acid metabolism, modified carbohydrate metabolism, industrial enhancements, yield stability, yield enhancement, disease resistance (bacterial, fungal, or viral), insect resistance, and herbicide resistance. In addition, an introgression site itself, such as an FRT site, Lox site, or other site-specific integration site, may be inserted by backcrossing and utilized for direct insertion of one or more genes of interest into a specific plant variety.

A single locus may contain several transgenes, such as a transgene for disease resistance that, in the same expression vector, also contains a transgene for herbicide resistance. The gene for herbicide resistance may be used as a selectable marker and/or as a phenotypic trait. A single locus conversion of site-specific integration system allows for the integration of multiple genes at a known recombination site in the genome. At least one, at least two or at least three and less than ten, less than nine, less than eight, less than seven, less than six, less than five or less than four locus conversions may be introduced into the plant by backcrossing, introgression or transformation to express the desired trait, while the plant, or a plant grown from the seed, plant part or plant cell, otherwise retains the phenotypic characteristics of the deposited seed when grown under the same environmental conditions.

The backcross conversion may result from either the transfer of a dominant allele or a recessive allele. Selection of progeny containing the trait of interest is accomplished by direct selection for a trait associated with a dominant allele. Transgenes transferred via backcrossing typically function as a dominant single gene trait and are relatively easy to classify. Selection of progeny for a trait that is transferred via a recessive allele requires growing and selfing the first backcross generation to determine which plants carry the recessive alleles. Recessive traits may require additional progeny testing in successive backcross generations to determine the presence of the locus of interest. The last backcross generation is usually selfed to give pure breeding progeny for the gene(s) being transferred, although a backcross conversion with a stably introgressed trait may also be maintained by further backcrossing to the recurrent parent with selection for the converted trait.

Along with selection for the trait of interest, progeny are selected for the phenotype of the recurrent parent. The backcross is a form of inbreeding, and the features of the recurrent parent are automatically recovered after successive backcrosses. Poehlman, Breeding Field Crops, p. 204 (1987). Poehlman suggests from one to four or more backcrosses, but as noted above, the number of backcrosses necessary can be reduced with the use of molecular markers. Other factors, such as a genetically similar donor parent, may also reduce the number of backcrosses necessary. As noted by Poehlman, backcrossing is easiest for simply inherited, dominant, and easily recognized traits.

One process for adding or modifying a trait or locus in celery cultivar TBG 54 comprises crossing celery cultivar TBG 54 plants grown from celery cultivar TBG 54 seed with plants of another celery variety that comprise the desired trait, gene or locus, selecting F$_1$ progeny plants that comprise the desired trait, gene or locus to produce selected F$_1$ progeny plants, crossing the selected progeny plants with the celery cultivar TBG 54 plants to produce backcross progeny plants, selecting for backcross progeny plants that have the desired trait, gene or locus and the morphological characteristics of celery cultivar TBG 54 to produce selected backcross progeny plants, and backcrossing to celery cultivar TBG 54 three or more times in succession to produce selected fourth or higher backcross progeny plants that comprise said trait, gene or locus. The modified celery cultivar TBG 54 may be further characterized as having the physiological and morphological characteristics of celery cultivar TBG 54 as determined at the 5% significance level when grown in the same environmental conditions and/or may be characterized by percent similarity or identity to celery cultivar TBG 54 as determined by SSR markers. The above method may be utilized with fewer backcrosses in appropriate situations, such as when the donor parent is highly related or markers are used in the selection step. Desired traits that may be used include those nucleic acids known in the art, some of which are listed herein, that will affect traits through nucleic acid expression or inhibition. Desired loci include the introgression of FRT, Lox, and other sites for site specific integration, which may also affect a desired trait if a functional nucleic acid is inserted at the integration site.

In addition, the above process and other similar processes described herein may be used to produce first generation progeny celery seed by adding a step at the end of the process that comprises crossing celery cultivar TBG 54 with the introgressed trait or locus with a different celery plant and harvesting the resultant first generation progeny celery seed.

Methods for Genetic Engineering of Celery

With the advent of molecular biological techniques that have allowed the isolation and characterization of genes that encode specific protein products, scientists in the field of plant biology developed a strong interest in engineering the genome of plants (genetic engineering) to contain and express foreign genes, or additional, or modified versions of native, or endogenous genes (perhaps driven by different promoters) in order to alter the traits of a plant in a specific manner. Plants altered by genetic engineering are often referred to as 'genetically modified'. Any DNA sequences, whether from a different species or from the same species, which are introduced into the genome using transformation and/or various breeding methods, are referred to herein collectively as "transgenes." Over the last fifteen to twenty years several methods for producing transgenic plants have been developed, and the present invention, in particular embodiments, also relates to transformed versions of the claimed cultivar.

Vectors used for the transformation of celery cells are not limited so long as the vector can express an inserted DNA in the cells. For example, vectors comprising promoters for constitutive gene expression in celery cells (e.g., cauliflower mosaic virus 35S promoter) and promoters inducible by exogenous stimuli can be used. Examples of suitable vectors include pBI binary vector. The "celery cell" into which the vector is to be introduced includes various forms of celery cells, such as cultured cell suspensions, protoplasts, leaf sections, and callus. A vector can be introduced into celery cells by known methods, such as the polyethylene glycol method, polycation method, electroporation, *Agrobacte-*

*rium*-mediated transfer, particle bombardment and direct DNA uptake by protoplasts. See, e.g., Pang et al. (The Plant J., 9, 899-909, 1996).

Numerous methods for plant transformation have been developed, including biological and physical, plant transformation protocols. See, for example, Miki, et al., "Procedures for Introducing Foreign DNA into Plants" in Methods in Plant Molecular Biology and Biotechnology, Glick and Thompson (Eds.), CRC Press, Inc., Boca Raton, pp. 67-88 (1993). In addition, expression vectors and in vitro culture methods for plant cell or tissue transformation and regeneration of plants are available. See, for example, Gruber, et al., "Vectors for Plant Transformation" in Methods in Plant Molecular Biology and Biotechnology, Glick and Thompson (Eds.), CRC Press, Inc., Boca Raton, pp. 89-119 (1993).

A. *Agrobacterium*-Mediated Transformation:

One method for introducing an expression vector into plants is based on the natural transformation system of *Agrobacterium*. See, for example, Horsch, et al., *Science,* 227:1229 (1985). *A. tumefaciens* and *A. rhizogenes* are plant pathogenic soil bacteria which genetically transform plant cells. The Ti and Ri plasmids of *A. tumefaciens* and *A. rhizogenes*, respectively, carry genes responsible for genetic transformation of the plant. See, for example, Kado, C. I., *Crit. Rev. Plant Sci.,* 10:1 (1991). Descriptions of *Agrobacterium* vector systems and methods for *Agrobacterium*-mediated gene transfer are provided by Gruber, et al., supra, Miki, et al., supra, and Moloney, et al., *Plant Cell Rep.,* 8:238 (1989). See also, U.S. Pat. No. 5,563,055 (Townsend and Thomas), issued Oct. 8, 1996.

*Agrobacterium*-mediated transfer is a widely applicable system for introducing gene loci into plant cells, including celery. An advantage of the technique is that DNA can be introduced into whole plant tissues, thereby bypassing the need for regeneration of an intact plant from a protoplast. Modern *Agrobacterium* transformation vectors are capable of replication in *E. coli* as well as *Agrobacterium*, allowing for convenient manipulations (Klee et al., Bio. Tech., 3(7): 637-642, 1985). Moreover, recent technological advances in vectors for *Agrobacterium*-mediated gene transfer have improved the arrangement of genes and restriction sites in the vectors to facilitate the construction of vectors capable of expressing various polypeptide coding genes. The vectors described have convenient multi-linker regions flanked by a promoter and a polyadenylation site for direct expression of inserted polypeptide coding genes. Additionally, *Agrobacterium* containing both armed and disarmed Ti genes can be used for transformation.

In those plant strains where *Agrobacterium*-mediated transformation is efficient, it is the method of choice because of the facile and defined nature of the gene locus transfer. The use of *Agrobacterium*-mediated plant integrating vectors to introduce DNA into plant cells is well known in the art (Fraley et al., Bio. Tech., 3(7):629-635, 1985; U.S. Pat. No. 5,563,055). For example, U.S. Pat. No. 5,349,124 describes a method of transforming celery plant cells using *Agrobacterium*-mediated transformation. By inserting a chimeric gene having a DNA coding sequence encoding for the full-length B.t. toxin protein that expresses a protein toxic toward Lepidopteran larvae, this methodology resulted in celery having resistance to such insects.

B. Direct Gene Transfer:

Several methods of plant transformation, collectively referred to as direct gene transfer, have been developed as an alternative to *Agrobacterium*-mediated transformation. A generally applicable method for delivering transforming DNA segments to plant cells is microprojectile-mediated transformation, or microprojectile bombardment. In this method, particles are coated with nucleic acids and delivered into cells by a propelling force. Sanford, et al., *Part. Sci. Technol.*, 5:27 (1987); Sanford, J. C., *Trends Biotech.*, 6:299 (1988); Klein, et al., *Bio/technology*, 6:559-563 (1988); Sanford, J. C., *Physiol Plant*, 7:206 (1990); Klein, et al., *Bio/technology*, 10:268 (1992). See also, U.S. Pat. No. 5,015,580 (Christou, et al.), issued May 14, 1991; U.S. Pat. No. 5,322,783 (Tomes, et al.), issued Jun. 21, 1994.

Another method for physical delivery of DNA to plants is sonication of target cells. Zhang, et al., *Bio/technology*, 9:996 (1991). Alternatively, liposome and spheroplast fusion have been used to introduce expression vectors into plants. Deshayes, et al., *EMBO J.*, 4:2731 (1985); Christou, et al., *PNAS*, 84:3962 (1987). Direct uptake of DNA into protoplasts using $CaCl_2$) precipitation, calcium phosphate precipitation, polyethylene glycol treatment, polyvinyl alcohol, or poly-L-ornithine has also been reported. See, e.g., Potrykus et al., *Mol. Gen. Genet.*, 199:183-188, 1985; Omirulleh et al., *Plant Mol. Biol.*, 21(3):415-428, 1993; Fromm et al., *Nature*, 312:791-793, 1986; Uchimiya et al., *Mol. Gen. Genet.*, 204:204, 1986; Marcotte et al., *Nature*, 335:454, 1988; Hain, et al., *Mol. Gen. Genet.*, 199:161,1985 and Draper, et al., *Plant Cell Physiol.* 23:451,1982.

Electroporation of protoplasts and whole cells and tissues has also been described. Donn, et al., In Abstracts of VIIth International Congress on Plant Cell and Tissue Culture IAPTC, A2-38, p. 53,1990; D'Halluin, et al., *Plant Cell*, 4:1495-1505,1992; and Spencer, et al., *Plant Mol. Biol.*, 24:51-61,1994. Another illustrative embodiment of a method for delivering DNA into plant cells by acceleration is the Biolistics Particle Delivery System, which can be used to propel particles coated with DNA or cells through a screen, such as a stainless steel or Nytex screen, onto a surface covered with target celery cells.

Transformation of plants and expression of foreign genetic elements is exemplified in Choi et al., *Plant Cell Rep.*, 13: 344-348, 1994 and Ellul et al., *Theor. Appl. Genet.*, 107:462-469, 2003.

Following transformation of celery target tissues, expression of selectable marker genes allows for preferential selection of transformed cells, tissues, and/or plants, using regeneration and selection methods now well known in the art.

The methods described herein for transformation would typically be used for producing a transgenic variety. The transgenic variety could then be crossed, with another (non-transformed or transformed) variety, in order to produce a new transgenic variety. Alternatively, a genetic trait which has been engineered into a particular celery cultivar using the transformation techniques described could be moved into another cultivar using traditional backcrossing techniques that are well known in the plant breeding arts. For example, a backcrossing approach could be used to move an engineered trait from a public, non-elite variety into an elite variety, or from a variety containing a foreign gene in its genome into a variety or varieties which do not contain that gene. As used herein, "crossing" can refer to a simple X by Y cross, or the process of backcrossing, depending on the context.

Expression Vectors for Celery Transformation: Marker Genes

Expression vectors include at least one genetic marker, operably linked to a regulatory element (a promoter, for example) that allows transformed cells containing the marker to be either recovered by negative selection, i.e., inhibiting growth of cells that do not contain the selectable marker gene, or by positive selection, i.e., screening for the product encoded by the genetic marker. Many commonly used selectable marker genes for plant transformation are well known in the transformation arts, and include, for example, genes that code for enzymes that metabolically detoxify a selective chemical agent which may be an antibiotic or a herbicide, or genes that encode an altered target which is insensitive to the inhibitor. A few positive selection methods are also known in the art.

One commonly used selectable marker gene for plant transformation is the neomycin phosphotransferase II (nptII) gene, isolated from transposon Tn5, which when placed under the control of plant regulatory signals which confers resistance to kanamycin. Fraley et al., *Proc. Natl. Acad. Sci. U.S.A.*, 80:4803 (1983). Another commonly used selectable marker gene is the hygromycin phosphotransferase gene which confers resistance to the antibiotic hygromycin. Van-den Elzen et al., *Plant Mol. Biol.*, 5:299 (1985).

Additional selectable marker genes of bacterial origin that confer resistance to antibiotics include gentamycin acetyl transferase, streptomycin phosphotransferase, aminoglyco-side-3'-adenyl transferase, the bleomycin resistance determinant. Hayford et al., *Plant Physiol.* 86:1216 (1988), Jones et al., *Mol. Gen. Genet.*, 210:86 (1987), Svab et al., *Plant Mol. Biol.* 14:197 (1990) Hille et al., *Plant Mol. Biol.* 7:171 (1986). Other selectable marker genes confer resistance to herbicides such as glyphosate, glufosinate or bromoxynil. Comai et al., *Nature* 317:741-744 (1985), Gordon-Kamm et al., *Plant Cell* 2:603-618 (1990) and Stalker et al., *Science* 242:419-423 (1988). Selectable marker genes for plant transformation not of bacterial origin include, for example, mouse dihydrofolate reductase, plant 5-enolpyruvylshikimate-3-phosphate synthase and plant acetolactate synthase. Eichholtz et al., *Somatic Cell Mol. Genet.* 13:67 (1987), Shah et al., *Science* 233:478 (1986), Charest et al., *Plant Cell Rep.* 8:643 (1990).

Another class of marker genes for plant transformation requires screening of presumptively transformed plant cells rather than direct genetic selection of transformed cells for resistance to a toxic substance such as an antibiotic. These genes are particularly useful to quantify or visualize the spatial pattern of expression of a gene in specific tissues and are frequently referred to as reporter genes because they can be fused to a gene or gene regulatory sequence for the investigation of gene expression. Commonly used genes for screening presumptively transformed cells include α-glucuronidase (GUS, α-galactosidase, luciferase and chloramphenicol, acetyltransferase. Jefferson, R. A., *Plant Mol. Biol. Rep.* 5:387 (1987), Teeri et al., *EMBO J.* 8:343 (1989), Koncz et al., *Proc. Natl. Acad. Sci U.S.A.* 84:131 (1987), DeBlock et al., *EMBO J.* 3:1681 (1984).

In vivo methods for visualizing GUS activity that do not require destruction of plant tissue are available. Molecular Probes publication 2908, IMAGENE GREEN, p. 1-4 (1993) and Naleway et al., *J. Cell Biol.* 115:151a (1991). However, these in vivo methods for visualizing GUS activity have not proven useful for recovery of transformed cells because of low sensitivity, high fluorescent backgrounds and limitations associated with the use of luciferase genes as selectable markers.

More recently, a gene encoding Green Fluorescent Protein (GFP) has been utilized as a marker for gene expression in prokaryotic and eukaryotic cells. Chalfie et al., *Science* 263:802 (1994). GFP and mutants of GFP may be used as screenable markers.

Expression Vectors for Celery Transformation: Promoters

Genes included in expression vectors must be driven by a nucleotide sequence comprising a regulatory element, for example, a promoter. Several types of promoters are now well known in the transformation arts, as are other regulatory elements that can be used alone or in combination with promoters.

As used herein, "promoter" includes reference to a region of DNA upstream from the start of transcription and involved in recognition and binding of RNA polymerase and other proteins to initiate transcription. A "plant promoter" is a promoter capable of initiating transcription in plant cells. Examples of promoters under developmental control include promoters that preferentially initiate transcription in certain tissues, such as leaves, roots, seeds, fibers, xylem vessels, tracheids, or sclerenchyma. Such promoters are referred to as "tissue-preferred". Promoters which initiate transcription only in certain tissue are referred to as "tissue-specific". A "cell type" specific promoter primarily drives expression in certain cell types in one or more organs, for example, vascular cells in roots or leaves. An "inducible" promoter is a promoter which is under environmental control. Examples of environmental conditions that may affect transcription by inducible promoters include anaerobic conditions or the presence of light. Tissue-specific, tissue-preferred, cell type specific, and inducible promoters constitute the class of "non-constitutive" promoters. A "constitutive" promoter is a promoter which is active under most environmental conditions.

A. Inducible Promoters:

An inducible promoter is operably linked to a gene for expression in celery. Optionally, the inducible promoter is operably linked to a nucleotide sequence encoding a signal sequence which is operably linked to a gene for expression in celery. With an inducible promoter the rate of transcription increases in response to an inducing agent.

Any inducible promoter can be used in the instant invention. See Ward et al., *Plant Mol. Biol.* 22:361-366 (1993). Exemplary inducible promoters include, but are not limited to, that from the ACEI system which responds to copper (Meft et al., PNAS 90:4567-4571 (1993)); In2 gene from maize which responds to benzenesulfonamide herbicide safeners (Hershey et al., *Mol. Gen Genetics* 227:229-237 (1991) and Gatz et al., *Mol. Gen. Genetics* 243:32-38 (1994)) or Tet repressor from Tn10 (Gatz et al., *Mol. Gen. Genetics* 227:229-237 (1991). A particularly preferred inducible promoter is a promoter that responds to an inducing agent to which plants do not normally respond. An exemplary inducible promoter is the inducible promoter from a steroid hormone gene, the transcriptional activity of which is induced by a glucocorticosteroid hormone. Schena et al., *Proc. Natl. Acad. Sci. U.S.A.* 88:0421 (1991).

B. Constitutive Promoters:

A constitutive promoter is operably linked to a gene for expression in celery or the constitutive promoter is operably linked to a nucleotide sequence encoding a signal sequence which is operably linked to a gene for expression in celery.

Many different constitutive promoters can be utilized in the instant invention. Exemplary constitutive promoters include, but are not limited to, the promoters from plant viruses such as the 35S promoter from CaMV (Odell et al., *Nature* 313:810-812 (1985) and the promoters from such genes as rice actin (McElroy et al., *Plant Cell* 2:163-171 (1990)); ubiquitin (Christensen et al., *Plant Mol. Biol.* 12:619-632 (1989) and Christensen et al., *Plant Mol. Biol.* 18:675-689 (1992)); pEMU (Last et al., *Theor. Appl. Genet.* 81:581-588 (1991)); MAS (Velten et al., *EMBO J.* 3:2723-2730 (1984)) and maize H3 histone (Lepetit et al., *Mol. Gen.*

*Genetics* 231:276-285 (1992) and Atanassova et al., *Plant Journal* 2 (3): 291-300 (1992)). The ALS promoter, Xba1/Ncol fragment 5' to the *Brassica napus* ALS3 structural gene (or a nucleotide sequence similarity to said Xba1/Ncol fragment), represents a particularly useful constitutive promoter. See PCT application WO 96/30530.

C. Tissue-Specific or Tissue-Preferred Promoters:

A tissue-specific promoter is operably linked to a gene for expression in celery. Optionally, the tissue-specific promoter is operably linked to a nucleotide sequence encoding a signal sequence which is operably linked to a gene for expression in celery. Plants transformed with a gene of interest operably linked to a tissue-specific promoter produce the protein product of the transgene exclusively, or preferentially, in a specific tissue.

Any tissue-specific or tissue-preferred promoter can be utilized in the instant invention. Exemplary tissue-specific or tissue-preferred promoters include, but are not limited to, a root-preferred promoter, such as that from the phaseolin gene (Murai et al., *Science* 23:476-482 (1983) and Sengupta-Gopalan et al., *Proc. Natl. Acad. Sci. U.S.A.* 82:3320-3324 (1985)); a leaf-specific and light-induced promoter such as that from cab or rubisco (Simpson et al., *EMBO J* 4(11):2723-2729 (1985) and Timko et al., *Nature* 318:579-582 (1985)); an anther-specific promoter such as that from LAT52 (Twell et al., *Mol. Gen. Genetics* 217:240-245 (1989)); a pollen-specific promoter such as that from Zm13 (Guerrero et al., *Mol. Gen. Genetics* 244:161-168 (1993)) or a microspore-preferred promoter such as that from apg (Twell et al., *Sex. Plant Reprod.* 6:217-224 (1993)).

Signal Sequences for Targeting Proteins to Subcellular Compartments

Transport of protein produced by transgenes to a subcellular compartment such as the chloroplast, vacuole, peroxisome, glyoxysome, cell wall or mitochondrion or for secretion into the apoplast, is accomplished by means of operably linking the nucleotide sequence encoding a signal sequence to the 5' and/or 3' region of a gene encoding the protein of interest. Targeting sequences at the 5' and/or 3' end of the structural gene may determine, during protein synthesis and processing, where the encoded protein is ultimately compartmentalized.

The presence of a signal sequence directs a polypeptide to either an intracellular organelle or subcellular compartment or for secretion to the apoplast. Many signal sequences are known in the art. See, for example Becker et al., *Plant Mol. Biol.* 20:49 (1992), Close, P. S., Master's Thesis, Iowa State University (1993), Knox, C., et al., "Structure and Organization of Two Divergent Alpha-Amylase Genes from Barley", *Plant Mol. Biol.* 9:3-17 (1987), Lerner et al., *Plant Physiol.* 91:124-129 (1989), Fontes et al., *Plant Cell* 3:483-496 (1991), Matsuoka et al., *Proc. Natl. Acad. Sci.* 88:834 (1991), Gould et al., *J. Cell. Biol.* 108:1657 (1989), Creissen et al., *Plant J.* 2:129 (1991), Kalderon, et al., A short amino acid sequence able to specify nuclear location, Cell 39:499-509 (1984), Steifel, et al., Expression of a maize cell wall hydroxyproline-rich glycoprotein gene in early leaf and root vascular differentiation, *Plant Cell* 2:785-793 (1990).

Additional Methods for Genetic Engineering of Celery

In general, methods to transform, modify, edit or alter plant endogenous genomic DNA include altering the plant native DNA sequence or a pre-existing transgenic sequence including regulatory elements, coding and non-coding sequences. These methods can be used, for example, to target nucleic acids to pre-engineered target recognition sequences in the genome. Such pre-engineered target sequences may be introduced by genome editing or modification. As an example, a genetically modified plant variety is generated using "custom" or engineered endonucleases such as meganucleases produced to modify plant genomes (see e.g., WO 2009/114321; Gao et al. (2010) *Plant Journal* 1:176-187). Another site-directed engineering method is through the use of zinc finger domain recognition coupled with the restriction properties of restriction enzyme. See e.g., Urnov, et al., (2010) *Nat Rev Genet.* 11(9):636-46; Shukla, et al., (2009) *Nature* 459 (7245):437-41. A transcription activator-like (TAL) effector-DNA modifying enzyme (TALE or TALEN) is also used to engineer changes in plant genome. See e.g., US20110145940, Cermak et al., (2011) *Nucleic Acids Res.* 39(12) and Boch et al., (2009), *Science* 326(5959): 1509-12. Site-specific modification of plant genomes can also be performed using the bacterial type II CRISPR (clustered regularly interspaced short palindromic repeats)/Cas (CRISPR-associated) system, as well as similar CRISPR related technologies. See e.g., Belhaj et al., (2013), *Plant Methods* 9: 39; The Cas9/guide RNA-based system allows targeted cleavage of genomic DNA guided by a customizable small noncoding RNA in plants (see e.g., WO 2015026883A1, incorporated herein by reference).

A genetic map can be generated that identifies the approximate chromosomal location of an integrated DNA molecule, for example via conventional restriction fragment length polymorphisms (RFLP), polymerase chain reaction (PCR) analysis, simple sequence repeats (SSR), and single nucleotide polymorphisms (SNP). For exemplary methodologies in this regard, see Glick and Thompson, *Methods in Plant Molecular Biology and Biotechnology*, pp. 269-284 (CRC Press, Boca Raton, 1993).

Wang et al. discuss "Large Scale Identification, Mapping and Genotyping of Single-Nucleotide Polymorphisms in the Human Genome", *Science* (1998) 280:1077-1082, and similar capabilities are increasingly available for the celery genome. Map information concerning chromosomal location is useful for proprietary protection of a subject transgenic plant. If unauthorized propagation is undertaken and crosses made with other germplasm, the map of the integration region can be compared to similar maps for suspect plants to determine if the latter have a common parentage with the subject plant. Map comparisons could involve hybridizations, RFLP, PCR, SSR, sequencing or combinations thereof, all of which are conventional techniques. SNPs may also be used alone or in combination with other techniques.

Celery Cultivar TBG 54 Further Comprising a Transgene

Transgenes and transformation methods provide means to engineer the genome of plants to contain and express heterologous genetic elements, including but not limited to foreign genetic elements, additional copies of endogenous elements, and/or modified versions of native or endogenous genetic elements, in order to alter at least one trait of a plant in a specific manner. Any heterologous DNA sequence(s), whether from a different species or from the same species, which are inserted into the genome using transformation, backcrossing, or other methods known to one of skill in the art are referred to herein collectively as transgenes. The sequences are heterologous based on sequence source, location of integration, operably linked elements, or any combination thereof. One or more transgenes of interest can be introduced into celery cultivar TBG 54. Transgenic variants of celery cultivar TBG 54 plants, seeds, cells, and parts thereof or derived therefrom are provided. Transgenic variants of TBG 54 comprise the physiological and morphological characteristics of celery cultivar TBG 54, such as determined at the 5% significance level when grown in the same environmental conditions, and/or may be characterized or identified by percent similarity or identity to TBG 54 as determined by SSR or other molecular markers. In some examples, transgenic variants of celery cultivar TBG 54 are produced by introducing at least one transgene of interest into celery cultivar TBG 54 by transforming TBG 54 with a polynucleotide comprising the transgene of interest. In other examples, transgenic variants of celery cultivar TBG 54 are produced by introducing at least one transgene by introgressing the transgene into celery cultivar TBG 54 by crossing.

In one example, a process for modifying celery cultivar TBG 54 with the addition of a desired trait, said process comprising transforming a celery plant of cultivar TBG 54 with a transgene that confers a desired trait is provided. Therefore, transgenic TBG 54 celery cells, plants, plant parts, and seeds produced from this process are provided. In some examples one more desired traits may include traits such as sterility (nuclear and cytoplasmic), fertility restoration, nutritional enhancements, drought tolerance, nitrogen utilization, altered fatty acid profile, modified fatty acid metabolism, modified carbohydrate metabolism, industrial enhancements, yield stability, yield enhancement, disease resistance (bacterial, fungal, or viral), insect resistance, and herbicide resistance. The specific gene may be any known in the art or listed herein, including but not limited to a polynucleotide conferring resistance to an ALS-inhibitor herbicide, imidazolinone, sulfonylurea, protoporphyrinogen oxidase (PPO) inhibitors, hydroxyphenyl pyruvate dioxygenase (HPPD) inhibitors, glyphosate, glufosinate, triazine, 2,4-dichlorophenoxyacetic acid (2,4-D), dicamba, broxynil, metribuzin, or benzonitrile herbicides; a polynucleotide encoding a *Bacillus thuringiensis* polypeptide, a polynucleotide encoding a phytase, a fatty acid desaturase (e.g., FAD-2, FAD-3), galactinol synthase, a raffinose synthetic enzyme; or a polynucleotide conferring resistance to tipburn, *Fusarium oxysporum, Nasonovia ribisnigri, Sclerotinia sclerotiorum* or other plant pathogens.

Foreign Protein Genes and Agronomic Genes

By means of the present invention, plants can be genetically engineered to express various phenotypes of agronomic interest. Through the transformation of celery, the expression of genes can be altered to enhance disease resistance, insect resistance, herbicide resistance, agronomic, nutritional quality, and other traits. Transformation can also be used to insert DNA sequences which control or help control male-sterility. DNA sequences native to celery, as well as non-native DNA sequences, can be transformed into celery and used to alter levels of native or non-native proteins. Various promoters, targeting sequences, enhancing sequences, and other DNA sequences can be inserted into the genome for the purpose of altering the expression of proteins. Reduction of the activity of specific genes (also known as gene silencing or gene suppression) is desirable for several aspects of genetic engineering in plants.

Many techniques for gene silencing are well known to one of skill in the art, including, but not limited to, knock-outs (such as by insertion of a transposable element such as mu (Vicki Chandler, The Maize Handbook, Ch. 118 (Springer-Verlag 1994)) or other genetic elements such as a FRT and Lox that are used for site specific integrations, antisense technology (see, e.g., Sheehy, et al., *PNAS USA,* 85:8805-8809 (1988); and U.S. Pat. Nos. 5,107,065, 5,453,566, and 5,759,829); co-suppression (e.g., Taylor, *Plant Cell,* 9:1245 (1997); Jorgensen, *Trends Biotech.,* 8(12):340-344 (1990); Flavell, *PNAS USA,* 91:3490-3496 (1994); Finnegan, et al.,

*Bio/Technology,* 12:883-888 (1994); Neuhuber, et al., *Mol. Gen. Genet.,* 244:230-241 (1994)); RNA interference (Napoli, et al., *Plant Cell,* 2:279-289 (1990); U.S. Pat. No. 5,034,323; Sharp, *Genes Dev.,* 13:139-141 (1999); Zamore, et al., *Cell,* 101:25-33 (2000); Montgomery, et al., *PNAS USA,* 95:15502-15507 (1998)), virus-induced gene silencing (Burton, et al., *Plant Cell,* 12:691-705 (2000); Baulcombe, Curr. *Op. Plant Bio.,* 2:109-113 (1999)); target-RNA-specific ribozymes (Haseloff, et al., *Nature,* 334: 585-591 (1988)); hairpin structures (Smith, et al., *Nature,* 407:319-320 (2000); WO 99/53050; WO 98/53083); MicroRNA (Aukerman & Sakai, *Plant Cell,* 15:2730-2741 (2003)); ribozymes (Steinecke, et al., *EMBO J.,* 11:1525 (1992); Perriman, et al., *Antisense Res. Dev.,* 3:253 (1993)); oligonucleotide mediated targeted modification (e.g., WO 03/076574 and WO 99/25853); Zn-finger targeted molecules (e.g., WO 01/52620, WO 03/048345, and WO 00/42219); and other methods or combinations of the above methods known to those of skill in the art.

Likewise, by means of the present invention, agronomic genes can be expressed in transformed plants. More particularly, plants can be genetically engineered to express various phenotypes of agronomic interest. Exemplary nucleotide sequences and/or native loci that confer at least one trait of interest, which optionally may be conferred or altered by genetic engineering, transformation or introgression of a transformed event include, but are not limited to, those categorized below:

1. Genes that Confer Resistance to Pests or Disease and that Encode:

A. Plant disease resistance genes. Plant defenses are often activated by specific interaction between the product of a disease resistance gene (R) in the plant and the product of a corresponding avirulence (Avr) gene in the pathogen. A plant line can be transformed with a cloned resistance gene to engineer plants that are resistant to specific pathogen strains. See, for example Jones et al., *Science* 266:789 (1994) (cloning of the tomato Cf-9 gene for resistance to *Cladosporium fulvum*); Martin et al., *Science* 262:1432 (1993) (tomato Pto gene for resistance to *Pseudomonas syringae* pv. Tomato encodes a protein kinase); Mindrinos et al., *Cell* 78:1089 (1994) (*Arabidopsis* RSP2 gene for resistance to *Pseudomonas syringae*).

B. A *Bacillus thuringiensis* protein, a derivative thereof or a synthetic polypeptide modeled thereon. See, for example, Geiser et al., *Gene* 48:109 (1986), who disclose the cloning and nucleotide sequence of a Bt δ-endotoxin gene. Moreover, DNA molecules encoding δ-endotoxin genes can be purchased from American Type Culture Collection, Manassas, Virginia, for example, under ATCC Accession Nos. 40098, 67136, 31995 and 31998.

C. A lectin. See, for example, the disclosure by Van Damme et al., *Plant Molec. Biol.* 24:25 (1994), who disclose the nucleotide sequences of several *Clivia miniata* mannose-binding lectin genes.

D. A vitamin-binding protein such as avidin. See PCT application US93/06487, the contents of which are hereby incorporated by reference. The application teaches the use of avidin and avidin homologues as larvicides against insect pests.

E. An enzyme inhibitor, for example, a protease or proteinase inhibitor or an amylase inhibitor. See, for example, Abe et al., *J. Biol. Chem.* 262:16793 (1987) (nucleotide sequence of rice cysteine proteinase inhibitor), Huub et al., *Plant Molec. Biol.* 21:985 (1993)

(nucleotide sequence of cDNA encoding tobacco proteinase inhibitor I), Sumitani et al., *Biosci. Biotech. Biochem.* 57:1243 (1993) (nucleotide sequence of *Streptomyces nitrosporeus* α-amylase inhibitor).

F. An insect-specific hormone or pheromone such as an ecdysteroid and juvenile hormone, a variant thereof, a mimetic based thereon, or an antagonist or agonist thereof. See, for example, the disclosure by Hammock et al., *Nature* 344:458 (1990), of baculovirus expression of cloned juvenile hormone esterase, an inactivator of juvenile hormone.

G. An insect-specific peptide or neuropeptide which, upon expression, disrupts the physiology of the affected pest. For example, see the disclosures of Regan, *J. Biol. Chem.* 269:9 (1994) (expression cloning yields DNA coding for insect diuretic hormone receptor), and Pratt et al., *Biochem. Biophys. Res. Comm.* 163:1243 (1989) (an allostatin is identified in *Diploptera puntata*). See also U.S. Pat. No. 5,266,317 to Tomalski et al., who disclose genes encoding insect-specific, paralytic neurotoxins.

H. An insect-specific venom produced in nature by a snake, a wasp, etc. For example, see Pang et al., *Gene* 116:165 (1992), for disclosure of heterologous expression in plants of a gene coding for a scorpion insectotoxic peptide.

I. An enzyme responsible for a hyper accumulation of a monoterpene, a sesquiterpene, a steroid, hydroxamic acid, a phenylpropanoid derivative or another non-protein molecule with insecticidal activity.

J. An enzyme involved in the modification, including the post-translational modification, of a biologically active molecule; for example, a glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase and a glucanase, whether natural or synthetic. See PCT application WO 93/02197 in the name of Scott et al., which discloses the nucleotide sequence of a callase gene. DNA molecules which contain chitinase-encoding sequences can be obtained, for example, from ATCC under Accession Nos. 39637 and 67152. See also Kramer et al., *Insect Biochem. Molec. Biol.* 23:691 (1993), who teach the nucleotide sequence of a cDNA encoding tobacco hookworm chitinase, and Kawalleck et al., *Plant Molec. Biol.* 21:673 (1993), who provide the nucleotide sequence of the parsley ubi4-2 polyubiquitin gene.

K. A molecule that stimulates signal transduction. For example, see the disclosure by Botella et al., *Plant Molec. Biol.* 24:757 (1994), of nucleotide sequences for mung bean calmodulin cDNA clones, and Griess et al., *Plant Physiol.* 104:1467 (1994), who provide the nucleotide sequence of a maize calmodulin cDNA clone.

L. A hydrophobic moment peptide. See PCT application WO 95/16776 (disclosure of peptide derivatives of Tachyplesin which inhibit fungal plant pathogens) and PCT application WO 95/18855 (teaches synthetic antimicrobial peptides that confer disease resistance), the respective contents of which are hereby incorporated by reference.

M. A membrane permease, a channel former or a channel blocker. For example, see the disclosure of Jaynes et al., *Plant Sci* 89:43 (1993), of heterologous expression of a cecropin-β, lytic peptide analog to render trans-
genic tobacco plants resistant to *Pseudomonas solan-
acearum*.

N. A viral-invasive protein or a complex toxin derived
therefrom. For example, the accumulation of viral coat
proteins in transformed plant cells imparts resistance to
viral infection and/or disease development effected by
the virus from which the coat protein gene is derived,
as well as by related viruses. See Beachy et al., *Ann.
rev. Phytopathol.* 28:451 (1990). Coat protein-mediated
resistance has been conferred upon transformed plants
against alfalfa mosaic virus, cucumber mosaic virus,
tobacco streak virus, potato virus X, potato virus Y,
tobacco etch virus, tobacco rattle virus and tobacco
mosaic virus. Id.

O. An insect-specific antibody or an immunotoxin derived
therefrom. Thus, an antibody targeted to a critical
metabolic function in the insect gut would inactivate an
affected enzyme, killing the insect. Cf. Taylor et al.,
Abstract #497, Seventh Int'l Symposium on Molecular
Plant-Microbe Interactions (Edinburgh, Scotland)
(1994) (enzymatic inactivation in transgenic tobacco
via production of single-chain antibody fragments).

P. A virus-specific antibody. See, for example, Tavlado-
raki et al., *Nature* 366:469 (1993), who show that
transgenic plants expressing recombinant antibody
genes are protected from virus attack.

Q. A developmental-arrestive protein produced in nature
by a pathogen or a parasite. Thus, fungal endo α-1,
4-D-polygalacturonases facilitate fungal colonization
and plant nutrient release by solubilizing plant cell wall
homo-α-1,4-D-galacturonase. See Lamb et al., *Bio/
Technology* 10:1436 (1992). The cloning and charac-
terization of a gene which encodes a celery endopoly-
galacturonase-inhibiting protein is described by
Toubart et al., *Plant J.* 2:367 (1992).

R. A developmental-arrestive protein produced in nature
by a plant. For example, Logemann et al., *Bio/Tech-
nology* 10:305 (1992), have shown that transgenic
plants expressing the barley ribosome-inactivating
gene have an increased resistance to fungal disease.

S. A lettuce mosaic potyvirus (LMV) coat protein gene
introduced into celery in order to increase its resistance
to LMV infection. See Dinant et al., *Molecular Breed-
ing.* 1997, 3: 1, 75-86.

T. Genes involved in the Systemic Acquired Resistance
(SAR) Response and/or the pathogenesis-related genes.
Briggs, S., *Current Biology,* 5(2) (1995).

U. Antifungal genes. See Cornelissen and Melchers, *Plant
Physiol.,* 101:709-712 (1993); Parijs et al., *Planta*
183:258-264 (1991) and Bushnell et al., *Can. J. of
Plant Path.* 20(2):137-149 (1998).

V. Genes that confer resistance to *Phytophthora* root rot,
such as the Rps 1, Rps 1-a, Rps 1-b, Rps 1-c, Rps 1-d,
Rps 1-e, Rps 1-k, Rps 2, Rps 3-a, Rps 3-b, Rps 3-c, Rps
4, Rps 5, Rps 6, Rps 7 and other Rps genes. See, for
example, Shoemaker et al., *Phytophthora* Root Rot
Resistance Gene Mapping in Soybean, Plant Genome
IV Conference, San Diego, Calif (1995).

2. Genes that Confer Resistance to an Herbicide:

A. An herbicide that inhibits the growing point or meri-
stem, such as an imidazolinone or a sulfonylurea.
Exemplary genes in this category code for mutant ALS
and AHAS enzyme as described, for example, by Lee
et al., *EMBO J.* 7:1241 (1988), and Miki et al., *Theor.
Appl. Genet.* 80:449 (1990), respectively.

B. Glyphosate (resistance impaired by mutant
5-enolpyruvlshikimate-3-phosphate synthase (EPSPS)
and aroA genes, respectively) and other phosphono
compounds such as glufosinate (phosphinothricin
acetyl transferase, PAT and *Streptomyces hygroscopi-
cus* phosphinothricin-acetyl transferase, bar, genes),
and pyridinoxy or phenoxy proprionic acids and cyclo-
hexones (ACCase inhibitor-encoding genes). See, for
example, U.S. Pat. No. 4,940,835 to Shah, et al., which
discloses the nucleotide sequence of a form of EPSPs
which can confer glyphosate resistance. A DNA mol-
ecule encoding a mutant aroA gene can be obtained
under ATCC accession number 39256, and the nucleo-
tide sequence of the mutant gene is disclosed in U.S.
Pat. No. 4,769,061 to Comai. See also Umaballava-
Mobapathie in *Transgenic Research.* 1999, 8: 1, 33-44
that discloses *Lactuca sativa* resistant to glufosinate.
European patent application No. 0 333 033 to Kumada
et al., and U.S. Pat. No. 4,975,374 to Goodman et al.,
disclose nucleotide sequences of glutamine synthetase
genes which confer resistance to herbicides such as
L-phosphinothricin. The nucleotide sequence of a
phosphinothricin-acetyl-transferase gene is provided in
European application No. 0 242 246 to Leemans et al.,
DeGreef et al., *Bio/Technology* 7:61 (1989), describe
the production of transgenic plants that express chime-
ric bar genes coding for phosphinothricin acetyl trans-
ferase activity. Exemplary of genes conferring resis-
tance to phenoxy proprionic acids and cyclohexones,
such as sethoxydim and haloxyfop are the Accl-S1,
Accl-S2 and Accl-S3 genes described by Marshall et
al., *Theor. Appl. Genet.* 83:435 (1992).

C. An herbicide that inhibits photosynthesis, such as a
triazine (psbA and gs+ genes) and a benzonitrile (nit-
rilase gene). Przibilla et al., *Plant Cell* 3:169 (1991),
describe the transformation of *Chlamydomonas* with
plasmids encoding mutant psbA genes. Nucleotide
sequences for nitrilase genes are disclosed in U.S. Pat.
No. 4,810,648 to Stalker, and DNA molecules contain-
ing these genes are available under ATCC Accession
Nos. 53435, 67441, and 67442. Cloning and expression
of DNA coding for a glutathione S-transferase is
described by Hayes et al., *Biochem. J.* 285:173 (1992).

D. Acetohydroxy acid synthase, which has been found to
make plants that express this enzyme resistant to mul-
tiple types of herbicides, has been introduced into a
variety of plants. See Hattori et al., *Mol. Gen. Genet.*
246:419, 1995. Other genes that confer tolerance to
herbicides include a gene encoding a chimeric protein
of rat cytochrome P4507A1 and yeast NADPH-cy-
tochrome P450 oxidoreductase (Shiota et al., *Plant
Physiol.,* 106:17, 1994), genes for glutathione
reductase and superoxide dismutase (Aono et al., *Plant
Cell Physiol.* 36:1687, 1995), and genes for various
phosphotransferases (Datta et al., *Plant Mol. Biol.*
20:619, 1992).

E. Protoporphyrinogen oxidase (PPO; protox) is the target
of the PPO-inhibitor class of herbicides; a PPO-inhibi-
tor resistant PPO gene was recently identified in *Ama-
ranthus tuberculatus* (Patzoldt et al., PNAS, 103(33):
12329-2334, 2006). PPO is necessary for the
production of chlorophyll, which is necessary for all
plant survival. The protox enzyme serves as the target
for a variety of herbicidal compounds. These herbicides
also inhibit growth of all the different species of plants
present, causing their total destruction. The develop-
ment of plants containing altered protox activity which are resistant to these herbicides are described in U.S. Pat. Nos. 6,288,306, 6,282,837, 5,767,373, and International Publication WO 01/12825.

F. Genes that confer resistance to auxin or synthetic auxin herbicides. For example an aryloxyalkanoate dioxy- genase (AAD) gene may confer resistance to arlyoxy-alkanoate herbicides, such as 2,4-D, as well as pyridy-loxyacetate herbicides, such as described in U.S. Pat. No. 8,283,522, and US2013/0035233. In other examples, a dicamba monooxygenase (DMO) is used to confer resistance to dicamba. Other polynucleotides of interest related to auxin herbicides and/or uses thereof include, for example, the descriptions found in U.S. Pat. Nos. 8,119,380; 7,812,224; 7,884,262; 7,855, 326; 7,939,721; 7,105,724; 7,022,896; 8,207,092; US2011/067134; and US2010/0279866. Any of the above listed herbicide genes (1-6) can be introduced into the claimed celery cultivar through a variety of means including, but not limited to, transformation and crossing.

3. Genes that Confer or Contribute to a Value-Added Trait, Such as:

A. Increased iron content of the celery, for example by transforming a plant with a soybean ferritin gene as described in Goto et al., *Acta Horticulturae.* 2000, 521, 101-109.

B. Decreased nitrate content of leaves, for example by transforming a celery with a gene coding for a nitrate reductase. See for example Curtis et al., *Plant Cell Report.* 1999, 18:11, 889-896.

C. Increased sweetness of the celery by transferring a gene coding for monellin that elicits a flavor 100,000 times sweeter than sugar on a molar basis. See Penarrubia et al., *Biotechnology.* 1992, 10:5, 561-564.

D. Modified fatty acid metabolism, for example, by transforming a plant with an antisense gene of stearyl-ACP desaturase to increase stearic acid content of the plant. See Knultzon et al., *Proc. Natl. Acad. Sci. USA* 89:2625 (1992).

E. Modified carbohydrate composition effected, for example, by transforming plants with a gene coding for an enzyme that alters the branching pattern of starch. See Shiroza et al., *J. Bacteriol.* 170:810 (1988) (nucleotide sequence of *Streptococcus* mutants fructosyltransferase gene), Steinmetz et al., *Mol. Gen. Genet.* 20:220 (1985) (nucleotide sequence of *Bacillus subtilis* levansucrase gene), Pen et al., Bio Technology 10:292 (1992) (production of transgenic plants that express *Bacillus lichenfonnis* α-amylase), Elliot et al., *Plant Molec. Biol.* 21:515 (1993) (nucleotide sequences of tomato invertase genes), Søgaard et al., *J. Biol. Chem.* 268:22480 (1993) (site-directed mutagenesis of barley α-amylase gene), and Fisher et al., *Plant Physiol.* 102:1045 (1993) (maize endosperm starch branching enzyme II).

F. Altered antioxidant content or composition, such as alteration of tocopherol or tocotrienols. See, for example, U.S. Pat. Nos. 6,787,683, 7,154,029, WO 00/68393 (involving the manipulation of antioxidant levels through alteration of a phytl prenyl transferase (ppt)); WO 03/082899 (through alteration of a homogentisate geranyl geranyl transferase (hggt)).

G. Modified bolting tolerance in plants for example, by transferring a gene encoding for gibberellin 2-oxidase (U.S. Pat. No. 7,262,340). Bolting has also been modified using non-transformation methods; see Wittwer, S. H., et al. (1957) *Science.* 126(3262): 30-31; Booij, R. et al., (1995) *Scientia Horticulturae.* 63:143-154; and Booij, R. et al., (1994) *Scientia Horticulturae.* 58:271-282.

H. Decreased browning of the celery, for example by transforming a plant with an siRNA, RNAi or microRNA vector, or other suppression sequence coding for polyphenol oxidase (PPO) to silence the expression of PPO genes. See Araji et al. (2014) Plant Physiology 164:1191-1203, Chi et al. (2014) BMC Plant Biology 14:62, and Carter, N., (2012) Petition for Determination of Nonregulated Status: Arctic™ Apple (*Malus×domestica*) Events GD743 and GS784, received by *APHIS.*

4. Genes that Control Male-Sterility

A. Introduction of a deacetylase gene under the control of a tapetum-specific promoter and with the application of the chemical N-Ac-PPT. See international publication WO 01/29237.

B. Introduction of various stamen-specific promoters. See international publications WO 92/13956 and WO 92/13957.

C. Introduction of the barnase and the barstar genes. See Paul et al., *Plant Mol. Biol.* 19:611-622, 1992).

For additional examples of nuclear male and female sterility systems and genes, see also, U.S. Pat. Nos. 5,859, 341, 6,297,426, 5,478,369, 5,824,524, 5,850,014, and 6,265, 640, all of which are hereby incorporated by reference.

5. Genes that Affect Abiotic Stress Resistance

Genes that affect abiotic stress resistance (including but not limited to flowering, seed development, enhancement of nitrogen utilization efficiency, altered nitrogen responsiveness, drought resistance or tolerance, cold resistance or tolerance, high or low light intensity, and salt resistance or tolerance) and increased yield under stress. For example, see: WO 00/73475 where water use efficiency is altered through alteration of malate; U.S. Pat. Nos. 5,892,009, 5,965,705, 5,929,305, 5,891,859, 6,417,428, 6,664,446, 6,706,866, 6,717,034, 6,801,104, WO 2000/060089, WO 2001/026459, WO 2001/035725, WO 2001/034726, WO 2001/035727, WO 2001/036444, WO 2001/036597, WO 2001/036598, WO 2002/015675, WO 2002/017430, WO 2002/077185, WO 2002/079403, WO 2003/013227, WO 2003/013228, WO 2003/014327, WO 2004/031349, WO 2004/076638, WO 98/09521, and WO 99/38977 describing genes, including CBF genes and transcription factors effective in mitigating the negative effects of freezing, high salinity, and drought on plants, as well as conferring other positive effects on plant phenotype; U.S. Publ. No. 2004/0148654 and WO 01/36596, where abscisic acid is altered in plants resulting in improved plant phenotype, such as increased yield and/or increased tolerance to abiotic stress; WO 2000/006341, WO 04/090143, U.S. Pat. Nos. 7,531,723 and 6,992,237, where cytokinin expression is modified resulting in plants with increased stress tolerance, such as drought tolerance, and/or increased yield. See also, WO 02/02776, WO 2003/052063, JP 2002281975, U.S. Pat. No. 6,084,153, WO 01/64898, and U.S. Pat. Nos. 6,177,275 and 6,107,547 (enhancement of nitrogen utilization and altered nitrogen responsiveness). For ethylene alteration, see, U.S. Publ. Nos. 2004/0128719, 2003/0166197, and WO 2000/32761. For plant transcription factors or transcriptional regulators of abiotic stress, see, e.g., U.S. Publ. Nos. 2004/0098764 or 2004/0078852.

Other genes and transcription factors that affect plant growth and agronomic traits, such as yield, flowering, plant growth, and/or plant structure, can be introduced or introgressed into plants. See, e.g., WO 97/49811 (LHY), WO 98/56918 (ESD4), WO 97/10339, U.S. Pat. No. 6,573,430 (TFL), 6,713,663 (FT), 6,794,560, 6,307,126 (GAI), WO 96/14414 (CON), WO 96/38560, WO 01/21822 (VRN1), WO 00/44918 (VRN2), WO 99/49064 (GI), WO 00/46358 (FRI), WO 97/29123, WO 99/09174 (D8 and Rht), WO 2004/076638, and WO 004/031349 (transcription factors).

Tissue Culture

Further reproduction of the variety can occur by tissue culture and regeneration. Tissue culture of various tissues of celery and regeneration of plants there from is well known and widely published. For example, reference may be had to Teng et al., *Hort Science.* 1992, 27: 9, 1030-1032 Teng et al., *Hort Science.* 1993, 28: 6, 669-1671, Zhang et al., *Journal of Genetics and Breeding.* 1992, 46: 3, 287-290, Webb et al., *Plant Cell Tissue and Organ Culture.* 1994, 38: 1, 77-79, Curtis et al., *Journal of Experimental Botany.* 1994, 45: 279, 1441-1449, Nagata et al., *Journal for the American Society for Horticultural Science.* 2000, 125: 6, 669-672, and Ibrahim et al., *Plant Cell,* Tissue and Organ Culture. (1992), 28(2): 139-145. It is clear from the literature that the state of the art is such that these methods of obtaining plants are routinely used and have a very high rate of success. Thus, another aspect of this invention is to provide cells which upon growth and differentiation produce celery plants having the physiological and morphological characteristics of variety TBG 54.

As used herein, the term "tissue culture" indicates a composition comprising isolated cells of the same or a different type or a collection of such cells organized into parts of a plant. Exemplary types of tissue cultures are protoplasts, calli, plant clumps, and plant cells that can generate tissue culture that are intact in plants or parts of plants, such as embryos, hypocotyls, pollen, flowers, seeds, leaves, stems, roots, root tips, pistils, anthers, meristematic cells and the like. Means for preparing and maintaining plant tissue culture are well known in the art. By way of example, a tissue culture comprising organs has been used to produce regenerated plants. U.S. Pat. Nos. 5,959,185; 5,973,234 and 5,977,445 describe certain techniques, the disclosures of which are incorporated herein by reference.

Industrial Uses of Celery Cultivar TBG 54

Celery may be used in a variety of manners including but not limited to, use in salads, soups, being filled with cheese, soybean, vegetable, peanut butter, or dairy type products, served raw, cooked, baked or frozen, served as sticks, pieces, diced, or dipped like potato chips, or used as straws.

Tables

In the tables that follow, the traits and characteristics of celery cultivar TBG 54 are given compared to other celery cultivars. Color references made in the Tables refer to the Munsell Color Chart. NA=Not Available.

Tables 2-4 show the results of celery cultivar TBG 54 grown in trials in Belle Glade, Florida. Based on these trials alone and depending on the particular trial, TBG 54 has characteristics that are most similar to celery cultivar TBG 31 or celery cultivar TBG 35. Celery cultivar TBG 54 contrasts most with varieties that are traditionally developed in and for Western United States production and in particular California. However, this is not surprising since the objective is to provide celery varieties that have a general characteristic or quality that the consumers prefer and, in the Florida environment, most of these archetype characteristics (height, length of joint, petiole count, color, etc.) have been preferentially selected in these three varieties under Florida production environments.

There are a few characteristics that differentiate celery cultivar TBG 54 from TBG 31 and TBG 35. TBG 54 tends to have a greater propensity to a deep cupped petiole shape which is more similar to TBG 31 but contrasting to TBG 35. This is not typically preferred since it is more likely to have the cup close onto (pinch) inner petioles or leaves which make the inner petioles bend and warp as they elongate with maturity and frequently break. However, it generally escapes this pinching issue because the celery plant is slightly less cylindrical/compact in its growing habit so less pinching occurs.

Celery cultivar TBG 54 typically has lower overall defect issues compared to TBG 31 and TBG 35. While for all of these varieties, defects usually occur with greater frequency as the celery gets over mature, the lower level of defects will generally allow more time for production which frequently coincides with increased yield.

Table 2 shows the result of a trial transplanted in Belle Glade, Florida Nov. 29, 2018, and evaluated Mar. 8, 2019 (99 days). This trial was grown in a normal and traditional production block that had no particular diseases or environmental stress. The plant population was 39,100 plants to the acre.

TABLE 2

| | | TBG 54 | TBG 31 | TBG 35 | ADS-8 | TBG 32 | ADS-23 |
|---|---|---|---|---|---|---|---|
| Plant Height (cm) | Average | 73.7 | 70.5 | 71.5 | 70.1 | 74.3 | 84.3 |
| | Range | (72-76) | (66-73) | (69-73) | (68-72) | (70-76) | (80-88) |
| Whole Plant | Average | 1.25 | 1.12 | 1.11 | 1.08 | 1.02 | 1.00 |
| weight (kg) | Range | (0.95-1.52) | (0.84-1.43) | (0.89-1.37) | (0.82-1.3) | (0.67-1.26) | (0.77-1.32) |
| Trimmed Plant Weight | Average | 1.02 | 0.93 | 0.93 | 0.91 | 0.81 | 0.75 |
| (kg @ 35.6 cm) | Range | (0.78-1.26) | (0.7-1.2) | (0.77-1.19) | (0.67-1.09) | (0.52-1.05) | (0.58-1.01) |
| Number of Outer | Average | 13.1 | 14.7 | 13.9 | 12.0 | 15.2 | 13.1 |
| Petioles (>35.6 cm) | Range | (4-16) | (11-17) | (11-17) | (10-14) | (10-19) | (12-14) |
| Number of Inner | Average | 6.7 | 6.9 | 7.1 | 6.6 | 6.1 | 6.4 |
| Petioles (<35.6 cm) | Range | (5-9) | (6-8) | (6-9) | (6-8) | (5-8) | (5-8) |
| Length of Outer | Average | 28.9 | 30.5 | 28.5 | 27.2 | 34.9 | 31.6 |
| Petioles @ joint (cm) | Range | (26-30) | (28-32.3) | (26.7-29.7) | (24.7-30.3) | (33-37.7) | (28.3-35) |
| Width of Outer | Average | 21.7 | 19.4 | 20.5 | 21.3 | 19.5 | 19.2 |
| Petioles @ midrib (mm) | Range | (20.3-23.3) | (18-21.3) | (18.7-22.3) | (20-22.7) | (18.3-20.7) | (17.7-23) |
| Thickness of Outer | Average | 10.4 | 8.7 | 10.0 | 10.4 | 8.7 | 8.7 |
| Petioles @ midrib (mm) | Range | (9.3-11.7) | (7.3-11) | (9.3-11.3) | (9.3-11) | (7.7-9.7) | (8-10) |
| Petiole Color | | 5gy 7/6 | 5gy 7/6 | 5gy 7/6 | 5gy 7/8- | 5gy 7/6 | 5gy 7/8- |
| (Munsell Color) | | | | | 5gy 6/10 | | 5gy 7/6 |
| Leaf Color | | 5gy 4/4 | 5gy 4/4 | 5gy 4/8 | 5gy 4/8 | 5gy 3/4 | 5gy 4/4 |
| (Munsell Color) | | | | | | | |
| Petiole Smoothness | | Smooth/ | Slight Rib | Smooth/ | Smooth/ | Smooth | Smooth/ |

TABLE 2-continued

| Petiole Cup | Slight Rib Cup/Deep Cup | Cup | Slight Rib Cup | Slight Rib Cup | Slight Cup/Cup | Slight Rib Cup |
|---|---|---|---|---|---|---|
| % Marketable Defects: | 100% | 100% | 100% | 100% | 100% | 100% |
| % Node Crack | 0% | 0% | 0% | 20% | 0% | 0% |
| % Brown Stem | 0% | 0% | 0% | 10% | 0% | 0% |
| % Butt Crack | 0% | 0% | 0% | 0% | 0% | 0% |
| % Top Pith | 0% | 0% | 10% | 20% | 10% | 90% |
| % Butt Pith | 0% | 0% | 0% | 10% | 0% | 50% |
| % Feather Leaf | 0% | 10% | 30% | 60% | 30% | 50% |
| % Blackheart | 0% | 0% | 0% | 0% | 0% | 0% |
| % Twist | 0% | 0% | 0% | 0% | 0% | 0% |

| | | Floribelle | TBG 37 | TBG 28 | TBG 29 | TBG 33 |
|---|---|---|---|---|---|---|
| Plant Height (cm) | Average | 69.60 | 73.9 | 79.2 | 72.3 | 71.2 |
| | Range | (65-75) | (68-80) | (75-84) | (68-79) | (67-77) |
| Whole Plant weight (kg) | Average | 0.89 | 0.80 | 0.77 | 0.93 | 0.79 |
| | Range | (0.64-1.29) | (0.64-1.04) | (0.66-0.89) | (0.61-1.26) | (0.46-0.96) |
| Trimmed Plant Weight (kg @ 35.6 cm) | Average | 0.74 | 0.62 | 0.60 | 0.75 | 0.63 |
| | Range | (0.53-1.07) | (0.5-0.85) | (0.51-0.68) | (0.5-1.01) | (0.37-0.76) |
| Number of Outer Petioles (>35.6 cm) | Average | 12.4 | 11.9 | 13.8 | 12.5 | 11.0 |
| | Range | (10-15) | (10-14) | (12-16) | (9-16) | (9-12) |
| Number of Inner Petioles (<35.6 cm) | Average | 6.2 | 5.5 | 5.1 | 6.6 | 5.0 |
| | Range | (4-16) | (4-7) | (4-6) | (4-9) | (3-6) |
| Length of Outer Petioles @ joint (cm) | Average | 28.0 | 28.4 | 30.1 | 25.7 | 26.4 |
| | Range | (26-32) | (26-31) | (29-31.7) | (22.3-29.7) | (24-29.3) |
| Width of Outer Petioles @ midrib (mm) | Average | 18.8 | 17.4 | 18.4 | 19.5 | 18.1 |
| | Range | (15.7-22.7) | (14.3-21.3) | (16.7-21) | (17-22) | (15.3-20.7) |
| Thickness of Outer Petioles @ midrib (mm) | Average | 8.3 | 7.8 | 7.9 | 9.1 | 7.7 |
| | Range | (6.7-10.3) | (7-9) | (6.3-9.7) | (6.3-10.3) | (5.7-8.7) |
| Petiole Color (Munsell Color) | | 5gy 7/8-5gy 6/10 | 5gy 6/6 | 5gy 6/6 | 5gy 7/8 | 5gy 7/6-5gy 6/6 |
| Leaf Color (Munsell Color) | | 5gy 4/8 | 5gy 4/4 | 5gy 4/8 | 5gy 4/8 | 5gy 4/6 |
| Petiole Smoothness | | Rib | Smooth | Smooth | Smooth/Slight Rib | Smooth/Slight Rib |
| Petiole Cup | | Slight Cup/Deep Cup | Cup | Slight Cup/Cup | Cup | Cup |
| % Marketable Defects: | | 0% | 10% | 0% | 0% | 20% |
| % Node Crack | | 10% | 0% | 30% | 10% | 20% |
| % Brown Stem | | 10% | 0% | 0% | 0% | 0% |
| % Butt Crack | | 10% | 0% | 0% | 0% | 0% |
| % Top Pith | | 60% | 90% | 100% | 90% | 80% |
| % Butt Pith | | 70% | 90% | 100% | 100% | 80% |
| % Feather Leaf | | 100% | 0% | 60% | 80% | 0% |
| % Blackheart | | 0% | 0% | 0% | 20% | 0% |
| % Twist | | 70% | 0% | 100% | 0% | 0% |

As shown in Table 2, under these conditions Floribelle and ADS-8 were the shortest for overall plant height and except for ADS-23 and TBG 28 which were the tallest the remaining varieties were fairly similar. TBG 35 was an improvement over ADS-8 for height, number and length of outer petioles and had considerably less defects. Under these conditions TBG 54 outperformed sister TBG 31 for height, yield (trimmed plant weight) and while it had less outer petioles they were wider and thicker. TBG 54 also out yielded each variety based on whole and trimmed weight and had thicker and wider petioles compared to all of the varieties. TBG 54 was also most similar but improved over sister TBG 31 for defects and considerably better than all other varieties. The California varieties planted in the trial (TBG 37, TBG 33, TBG 29 and TBG 28 were generally the lowest yielding (trimmed plant weight), poorest marketability and had significant issues with defects, in particular pith.

Table 3 shows the result of a trial transplanted in Belle Glade, Florida Oct. 13, 2018, and evaluated Jan. 22, 2019 (101 days). This trial was grown in a normal and traditional production block that had no particular diseases or environmental stress. The plant population was 39,100 plants to the acre. Represented in the trial of Florida varieties were California varieties TBG 37, TBG 29 and TBG 33 as well as a variety that was developed for use in Michigan, TBG 28

TABLE 3

| | | TBG 54 | TBG 31 | TBG 35 | ADS-8 | TBG 32 |
|---|---|---|---|---|---|---|
| Plant Height (cm) | Average | 72.1 | 77.0 | 73.3 | 70.5 | 82.4 |
| | Range | (68-76) | (75-79) | (70-77) | (66-74) | (80-85) |
| Whole Plant weight (kg) | Average | 1.23 | 1.37 | 1.35 | 1.30 | 1.34 |
| | Range | (0.99-1.41) | (1.16-1.61) | (1.11-1.52) | (0.95-1.65) | (1.11-1.55) |

TABLE 3-continued

| | | | | | | |
|---|---|---|---|---|---|---|
| Trimmed Plant Weight | Average | 1.01 | 1.09 | 1.07 | 1.06 | 0.99 |
| (kg @ 35.6 cm) | Range | (0.82-1.16) | (0.91-1.3) | (0.89-1.22) | (0.8-1.36) | (0.84-1.16) |
| Number of Outer | Average | 13.3 | 12.6 | 11.4 | 11.4 | 11.9 |
| Petioles (>35.6 cm) | Range | (11-15) | (11-14) | (10-13) | (10-14) | (10-13) |
| Number of Inner | Average | 6.5 | 5.5 | 7.1 | 6.7 | 5.5 |
| Petioles (<35.6 cm) | Range | (5-8) | (3-7) | (5-8) | (6-8) | (4-7) |
| Length of Outer | Average | 29.5 | 33.1 | 28.1 | 25.5 | 35.8 |
| Petioles @ joint (cm) | Range | (27.3-31.7) | (31.7-34.7) | (23-30.7) | (19-29.3) | (32.7-37.7) |
| Width of Outer | Average | 20.9 | 21.6 | 22.1 | 23.0 | 22.2 |
| Petioles @ midrib (mm) | Range | (19-23) | (19.7-23.7) | (19.7-24) | (20-24.7) | (20.7-24) |
| Thickness of Outer | Average | 11.1 | 11.0 | 11.2 | 11.6 | 11.4 |
| Petioles @ midrib (mm) | Range | (10.3-12.7) | (10-12) | (10.7-12.3) | (10.3-13.3) | (10.7-12.7) |
| Petiole Color (Munsell Color) | | 5GY 7/8 | 5GY 7/8 | 5GY 7/8 | 5GY 6/6 | 2.5GY 8/6 |
| Leaf Color (Munsell Color) | | 5GY 4/6 | 7.5GY 5/6 | 7.5GY 4/4 | 5GY 4/4 | 5GY 4/8 |
| Petiole Smoothness | | Smooth/ Slight Rib | Smooth/ Slight Rib | Smooth/ Slight Rib | Smooth | Smooth |
| Petiole Cup | | Cup | Cup | Cup | Cup/ Deep Cup | Cup |
| % Marketable | | 100% | 100% | 100% | 100% | 100% |
| Defects: | | | | | | |
| % Node Crack | | 40% | 70% | 60% | 100% | 40% |
| % Feather Leaf | | 0% | 10% | 20% | 60% | 40% |
| % Blackheart | | 0% | 0% | 0% | 0% | 0% |

| | | ADS-23 | TBG 37 | TBG 28 | TBG 29 | TBG 33 |
|---|---|---|---|---|---|---|
| Plant Height (cm) | Average | 88.6 | 82.9 | 84.4 | 72.8 | 79.0 |
| | Range | (84-92) | (79-87) | (80-89) | (66-79) | (73-82) |
| Whole Plant | Average | 1.42 | 1.20 | 0.96 | 0.80 | 0.88 |
| weight (kg) | Range | (1.01-1.79) | (1.03-1.39) | (0.77-1.28) | (0.65-0.93) | (0.56-1.07) |
| Trimmed Plant Weight | Average | 1.00 | 0.89 | 0.68 | 0.66 | 0.65 |
| (kg @ 35.6 cm) | Range | (0.7-1.27) | (0.77-1.05) | (0.55-0.88) | (0.55-0.76) | (0.42-0.82) |
| Number of Outer | Average | 11.7 | 12.9 | 11.9 | 9.6 | 9.4 |
| Petioles (>35.6 cm) | Range | (10-14) | (12-14) | (10-15) | (7-12) | (7-11) |
| Number of Inner | Average | 6.5 | 6.2 | 5.2 | 6.3 | 4.6 |
| Petioles (<35.6 cm) | Range | (5-8) | (5-7) | (4-7) | (5-9) | (3-6) |
| Length of Outer | Average | 33.8 | 34.2 | 32.5 | 25.1 | 32.0 |
| Petioles @ joint (cm) | Range | (31.3-36.7) | (31.3-37.3) | (30.3-35.7) | (21.3-27) | (28.3-36) |
| Width of Outer | Average | 22.0 | 20.3 | 18.6 | 19.2 | 19.6 |
| Petioles @ midrib (mm) | Range | (18.3-23.3) | (18.3-22.3) | (16.3-20) | (16.7-21) | (17.3-21.3) |
| Thickness of Outer | Average | 10.7 | 9.9 | 9.4 | 9.4 | 9.0 |
| Petioles @ midrib (mm) | Range | (9.3-11.3) | (8.7-11) | (8.3-11) | (8-10.3) | (8.3-9.7) |
| Petiole Color (Munsell Color) | | 5GY 7/6 | 5GY 7/8 | 5GY 7/8 | 5GY 7/8 | 5GY 7/8 |
| Leaf Color (Munsell Color) | | 5GY 4/4 | 5GY 5/8 | 7.5GY 4/6 | 5GY 4/8 | 5GY 4/8 |
| Petiole Smoothness | | Smooth | Smooth | Smooth/ Slight Rib | Smooth/ Slight Rib | Smooth/ Slight Rib |
| Petiole Cup | | Cup/Deep Cup | Cup | Slight Cup/Cup | Cup | Cup |
| % Marketable | | 100% | 100% | 100% | 0% | 90% |
| Defects: | | | | | | |
| % Node Crack | | 0% | 40% | 0% | 0% | 70% |
| % Feather Leaf | | 0% | 100% | 0% | 0% | 0% |
| % Blackheart | | 0% | 0% | 0% | 100% | 0% |

As shown in Table 3, under these conditions ADS-23 is the tallest (plant height) of the varieties followed by TBG 28 and TBG 32 and TBG 37 which were similar. ADS-8 was the shortest of the varieties followed by TBG 54. ADS-23 also had the greatest whole plant weight followed by TBG 31, TBG 35 and TBG 32 which were all fairly similar. In contrast TBG 31, TBG 35 and ADS-8 all had had the highest trimmed weight (market weight) followed by TBG 54, ADS-23 and TBG 32 which were fairly similar. The lowest trimmed weight was for the California varieties and TBG 28. While TBG 54 was shorter than sister TBG 31 and had slightly lower trimmed weight than TBG 31 and ADS-8 and its progeny TBG 35, it was fairly similar to sister TBG 31 for width and thickness of outer petioles. Where TBG 54 stood out was having less defects compared to its sister TBG 31 and ADS-8 and its progeny TBG 35.

Table 4 shows the result of a trial transplanted in Belle Glade, Florida Oct. 24, 2019, and evaluated Jan. 31, 2020 (99 days). Both Eastern varieties developed for Florida (TBG 31, 32, 35, 53, 54, Floribelle, ADS-8 and 23) and Michigan (TBG 28) production in muck soil and Western varieties, developed for California and Arizona production on mineral soil (TBG 29, 33, 37 and ADS-1) where grown in a normal production block on muck soil that had no particular diseases or environmental stress. The plant population was 39,100 plants to the acre.

TABLE 4

| | | TBG 54 | TBG 31 | TBG 35 | ADS-8 | TBG 32 | TBG 53 | ADS-23 |
|---|---|---|---|---|---|---|---|---|
| Plant Height (cm) | Average | 75.8 | 73.4 | 75.9 | 74.8 | 78.1 | 73.3 | 85.5 |
| | Range | (74-78) | (70-77) | (72-79) | (69-80) | (76-81) | (69-79) | (82-89) |
| Whole Plant | Average | 1.23 | 1.13 | 1.34 | 1.01 | 1.21 | 1.23 | 1.17 |
| weight (kg) | Range | (1.09-1.51) | (0.86-1.31) | (0.88-1.84) | (0.8-1.22) | (0.88-1.53) | (1.03-1.49) | (1.03-1.46) |
| Trimmed Plant Weight | Average | 0.98 | 0.90 | 1.09 | 0.83 | 0.94 | 1.00 | 0.85 |
| (kg @ 35.6 cm) | Range | (0.84-1.27) | (0.71-1.07) | (0.7-1.5) | (0.69-1) | (0.68-1.21) | (0.81-1.22) | (0.73-1.04) |
| Number of Outer | Average | 12.7 | 13.3 | 13.2 | 11.0 | 12.9 | 14.6 | 12.1 |
| Petioles (>35.6 cm) | Range | (11-16) | (10-17) | (8-17) | (10-13) | (9-15) | (13-17) | (10-13) |
| Number of Inner | Average | 4.2 | 4.6 | 4.0 | 3.9 | 3.9 | 5.1 | 4.8 |
| Petioles (<35.6 cm) | Range | (3-5) | (3-5) | (3-5) | (3-5) | (2-6) | (3-6) | (4-6) |
| Length of Outer | Average | 32.9 | 32.1 | 31.4 | 29.0 | 34.2 | 34.6 | 34.7 |
| Petioles to the joint (cm) | Range | (31.3-35) | (29-36.3) | (27.7-36) | (26.7-32) | (31-36.3) | (32.7-36.7) | (30.7-37.7) |
| Width of Outer | Average | 22.3 | 21.8 | 20.8 | 20.5 | 21.8 | 21.3 | 21.0 |
| Petioles at the midrib (mm) | Range | (20.3-24) | (20.3-23.3) | (19-25) | (19-22.3) | (19.7-23.7) | (19.3-23.7) | (19.7-22.3) |
| Thickness of Outer | Average | 9.6 | 8.9 | 9.6 | 9.2 | 9.8 | 9.3 | 9.4 |
| Petioles at the midrib (mm) | Range | (8.7-10.3) | (8-10) | (8.7-10.7) | (7.7-10.3) | (8.3-10.7) | (8.3-10) | (8.3-10.3) |
| Petiole Color (Munsell Color Chart) | | 5GY 6/8 | 5 GY 5/10 | 5GY 6/8 | 5GY 6/6 | 5 GY 6/8 | 5 GY 6/10 | 5GY 7/6 |
| Leaf Color (Munsell Color Chart) | | 5GY 4/8 | 5 GY 4/8 | 5GY 5/4 | 5GY 4/4 | 5GY 4/8 | 5GY 5/6 | 5GY 5/6 |
| Petiole Smoothness | | Smooth/ Slight Rib | Smooth/ Slight Rib | Slight Rib | Smooth/ Slight Rib | Smooth/ Slight Rib | Smooth/ Slight Rib | Smooth |
| Petiole Cup | | Cup/ Deep Cup | Cup/ Deep Cup | Cup | Cup/ Deep Cup | Slight Cup/Cup | Cup/ Deep Cup | Cup/ Deep Cup |
| % Marketable | | 100% | 100% | 100% | 70% | 100% | 100% | 100% |
| Defects: | | | | | | | | |
| % Node Crack | | 10% | 10% | 10% | 40% | 0% | 10% | 0% |
| % Brown Stem | | 0% | 0% | 0% | 0% | 0% | 0% | 10% |
| % Top Pith | | 0% | 10% | 0% | 20% | 0% | 0% | 0% |
| % Butt Pith | | 20% | 30% | 10% | 0% | 0% | 0% | 10% |
| % Feather Leaf | | 30% | 30% | 80% | 30% | 40% | 40% | 40% |
| % Twist | | 40% | 10% | 30% | 0% | 10% | 0% | 60% |

| | | Floribelle | TBG 28 | TBG 37 | ADS-1 | TBG 29 | TBG 33 |
|---|---|---|---|---|---|---|---|
| Plant Height (cm) | Average | 70.8 | 83.1 | 83.6 | 82.0 | 77.6 | 79.8 |
| | Range | (65-76) | (80-87) | (80-86) | (76-86) | (75-81) | (69-87) |
| Whole Plant | Average | 1.08 | 1.26 | 1.05 | 1.00 | 0.94 | 0.95 |
| weight (kg) | Range | (0.83-1.32) | (0.99-1.58) | (0.75-1.37) | (0.73-1.22) | (0.62-1.2) | (0.54-1.36) |
| Trimmed Plant Weight | Average | 0.86 | 0.95 | 0.79 | 0.77 | 0.74 | 0.71 |
| (kg @ 35.6 cm) | Range | (0.67-1.03) | (0.73-1.2) | (0.56-1.03) | (0.57-0.93) | (0.48-0.96) | (0.4-1.03) |
| Number of Outer | Average | 12.3 | 13.7 | 11.4 | 10.6 | 11.3 | 11.3 |
| Petioles (>35.6 cm) | Range | (9-15) | (10-17) | (9-14) | (9-12) | (10-15) | (8-13) |
| Number of Inner | Average | 3.4 | 3.5 | 3.6 | 3.6 | 3.3 | 3.1 |
| Petioles (<35.6 cm) | Range | (2-4) | (2-5) | (3-4) | (2-5) | (2-4) | (2-4) |
| Length of Outer | Average | 28.9 | 32.3 | 32.6 | 28.8 | 20.7 | 30.5 |
| Petioles to the joint (cm) | Range | (25.7-32.7) | (30-36) | (28.7-35.7) | (27-30.3) | (17.3-23.3) | (26.7-35) |
| Width of Outer | Average | 20.7 | 21.6 | 20.2 | 19.8 | 20.7 | 19.0 |
| Petioles at the midrib (mm) | Range | (18.7-23) | (20.3-24) | (18.3-22.3) | (18-21.7) | (17.3-23.3) | (15.7-21) |
| Thickness of Outer | Average | 9.4 | 9.9 | 8.9 | 9.0 | 9.2 | 8.5 |
| Petioles at the midrib (mm) | Range | (8.3-10.3) | (9.3-10.7) | (8-10) | (8.3-10) | (6.3-10) | (7-10.3) |
| Petiole Color (Munsell Color Chart) | | 5GY 7/6 | 5GY7/6- 5GY6/6 | 5GY 6/6 | 5GY 7/6 | 5GY 7/6 | 5GY 7/6- 5GY6/6 |
| Leaf Color (Munsell Color Chart) | | 5GY 4/6 | 5GY 4/4 | 5GY 3/4 | 5GY 3/4 | 5GY 4/4 | 5GY 4/4 |
| Petiole Smoothness | | Rib | Smooth | Smooth | Smooth/ Slight Rib | Smooth | Slight Rib |
| Petiole Cup | | Cup | Cup | Cup | Deep Cup | Cup | Cup/ Deep Cup |
| % Marketable | | 0% | 100% | 100% | 60% | 40% | 50% |
| Defects: | | | | | | | |
| % Node Crack | | 0% | 0% | 0% | 10% | 0% | 20% |
| % Brown Stem | | 40% | 0% | 0% | 0% | 0% | 0% |
| % Top Pith | | 100% | 0% | 0% | 0% | 10% | 30% |
| % Butt Pith | | 100% | 0% | 10% | 50% | 40% | 30% |
| % Feather Leaf | | 100% | 0% | 10% | 30% | 60% | 20% |
| % Twist | | 0% | 0% | 0% | 40% | 0% | 0% |

43

44

As shown in Tables 4, under these conditions, except for ADS-23 and TBG 29, the California and Michigan varieties produced the tallest stalks. However, the California varieties (ADS-1, TBG 29, 22 and 37) were also the lowest yielding (trimmed plant weight), had the lowest outer petiole count and except for TBG 37 had very low percentage of marketable stalks. Of the Florida varieties TBG 54 was a definite improvement over its sister TBG 31 for trimmed weight, length of outer petioles and plant height. TBG 53 similarly out yielded its parent TBG 32 for trimmed weight and number of outer petioles. While it had outer petiole length similar to TBG 32 it was shorter for overall height indicating that there had less foliage. Under these conditions TBG 53 was also fairly similar to TBG 54 for trimmed weight however it possessed higher petiole count (inner and outer) and had longer petioles as measured to the joint. Under these conditions both were out yielded by TBG 35 based on trimmed plant weight. TBG 35 was also a significant improvement over its progenitor ADS-8 which had lower yield, shorter height and length to the joint and lower marketability. TBG 35 was also significantly improved over ADS-8 for propensity for node cracks but was faster maturing and showing signs of increased feather leaf, though not at a level which caused loss of market grade. TBG 53 and TBG 32 were very similar for defects as were TBG 54 and TBG 31 and none were sufficient to cause loss of market grade or marketability. The only variety free from defects was TBG 28 which was developed for Michigan and summer production in muck soil. TBG 54 was not only one of the tallest varieties (stalk height) but was also had smoother petioles than the Florida varieties and yield fairly similar (trimmed weight) to TBG 32 and TBG 54.

Where celery cultivar TBG 54 differentiates itself from celery cultivar TBG 31, celery cultivar TBG 35, and several other Florida varieties is a surprising improvement in bolting tolerance. Tables 5 through 8 show the results of TBG 54 being grown in trials in California that have had considerable cold exposure during the winter production months.

Under these conditions, TBG 54 demonstrates improvement for bolting tolerance as measured by seed stem length compared to its sister, TBG 31, and Florida varieties ADS-8, TBG 35, and TBG 32. TBG 53 a descendant of TBG 32 and ADS-23, also Florida varieties show fairly comparable or improved tolerance but differ in other archetypal characteristics.

This tolerance does not compare to Western varieties like ADS-20 which have very strong bolting tolerance, however Florida does not receive the amount of cold temperature accumulation that can occur in California. Hence, the level of bolting tolerance required is lower for Florida varieties. In contrast, a Florida bolting tolerant variety may not have sufficient tolerance to be bolting tolerant under bolting induction conditions of other areas like California (in example: TBG 54, TBG 53, ADS-23, Florida Slowbolt, etc.). Keeping in mind the occurrence of a regional consideration for bolting tolerance, these California bolting trials provide an excellent opportunity for comparing varieties.

The improved bolting tolerance demonstrated by celery cultivar TBG 54 in tables 5-8 demonstrate its advantage over prior preeminent Florida varieties like ADS-8 and TBG 31 as well as ADS-8's descendant TBG 35 for the Florida spring harvest season. During this harvest season, March to May, especially cool Florida winters can cause the less tolerant varieties to bolt which can significantly decrease quality and marketability.

Tables 5A and 5B show the result of a trial transplanted in Oxnard, California Dec. 19, 2019, and evaluated Apr. 26, 2020 (129 days). This trial was grown in a normal production field that had moderate to heavy pressure for bolting (864 hours below 50° F.), measured by seed stem length. The only characteristics measured for varieties with an average seed stem length of 10 cm and higher were length of outer petioles at the joint and seed stem length. NA represents no data available. The plant population (58,080 plants to the acre) was higher than the commercial norm of approximately 45,000 to 47,000 plants to the acre.

TABLE 5A

| | | TBG 54 | TBG 31 | TBG 35 | ADS-8 | TBG 32 | TBG 53 | ADS-22 | TBG 37 | TBG 43 | TBG 29 | ADS-1 |
|---|---|---|---|---|---|---|---|---|---|---|---|---|
| Plant Height (cm) | Average | NA | NA | NA | NA | NA | NA | NA | NA | NA | NA | NA |
| | Range | | | | | | | | | | | |
| Whole Plant weight (kg) | Average | NA | NA | NA | NA | NA | NA | NA | NA | NA | NA | NA |
| | Range | | | | | | | | | | | |
| Trimmed Plant Weight (kg @ 35.6 cm) | Average | NA | NA | NA | NA | NA | NA | NA | NA | NA | NA | NA |
| | Range | | | | | | | | | | | |
| Number of Outer Petioles (>35.6 cm) | Average | NA | NA | NA | NA | NA | NA | NA | NA | NA | NA | NA |
| | Range | | | | | | | | | | | |
| Number of Inner Petioles (<35.6 cm) | Average | NA | NA | NA | NA | NA | NA | NA | NA | NA | NA | NA |
| | Range | | | | | | | | | | | |
| Length of Outer Petioles to the joint (cm) | Average | NA | NA | NA | NA | NA | NA | NA | NA | NA | NA | NA |
| | Range | | | | | | | | | | | |
| Width of Outer Petioles at the midrib (mm) | Average | NA | NA | NA | NA | NA | NA | NA | NA | NA | NA | NA |
| | Range | | | | | | | | | | | |
| Thickness of Outer Petioles at the midrib (mm) | Average | NA | NA | NA | NA | NA | NA | NA | NA | NA | NA | NA |
| | Range | | | | | | | | | | | |
| Seed Stem Length (cm) | Average | 28.9 | 51.2 | 56.1 | 47.9 | 50.8 | 35.7 | 18.0 | 32.7 | 28.6 | 23.1 | 26.3 |
| Reading Date 1 | Range | (23-35) | (35-70) | (44-68) | (36-56) | (42-58) | (18-52) | (13-26) | (23-55) | (12-46) | (4-41) | (6-37) |
| | Median | 29.5 | 50.0 | 55.0 | 48.5 | 52.0 | 40.0 | 16.5 | 30.5 | 28.5 | 22.0 | 27.5 |
| Petiole Color (Munsell Color Chart) | | NA | NA | NA | NA | NA | NA | NA | NA | NA | NA | NA |
| Leaf Color (Munsell Color Chart) | | NA | NA | NA | NA | NA | NA | NA | NA | NA | NA | NA |
| Petiole Smoothness | | NA | NA | NA | NA | NA | NA | NA | NA | NA | NA | NA |
| Petiole Cup | | NA | NA | NA | NA | NA | NA | NA | NA | NA | NA | NA |
| % Marketable | | 0% | 0% | 0% | 0% | 0% | 0% | 0% | 0% | 20% | 30% | 10% |

TABLE 5A-continued

| | TBG 54 | TBG 31 | TBG 35 | ADS-8 | TBG 32 | TBG 53 | ADS-22 | TBG 37 | TBG 43 | TBG 29 | ADS-1 |
|---|---|---|---|---|---|---|---|---|---|---|---|
| Defects: | | | | | | | | | | | |
| % Butt Pith | NA | NA | NA | NA | NA | NA | NA | NA | NA | NA | NA |
| % Twist | NA | NA | NA | NA | NA | NA | NA | NA | NA | NA | NA |

TABLE 5B

| | | TBG 34 | TBG 28 | TBG 33 | Hill's Special | ADS-20 | Challenger |
|---|---|---|---|---|---|---|---|
| Plant Height (cm) | Average | 79.70 | NA | NA | 71.70 | 70.00 | NA |
| | Range | (75-85) | | | (68-74) | (62-75) | |
| Whole Plant weight (kg) | Average | 1.23 | NA | NA | 1.13 | 1.00 | NA |
| | Range | (0.84-1.62) | | | (0.82-1.54) | (0.74-1.28) | |
| Trimmed Plant Weight (kg @ 35.6 cm) | Average | 0.93 | NA | NA | 0.90 | 0.81 | NA |
| | Range | (0.66-1.22) | | | (0.66-1.2) | (0.6-1.02) | |
| Number of Outer Petioles (>35.6 cm) | Average | 10.1 | NA | NA | 10.1 | 12.5 | NA |
| | Range | (8-12) | | | (7-13) | (11-14) | |
| Number of Inner Petioles (<35.6 cm) | Average | 7.2 | NA | NA | 7.2 | 7.6 | NA |
| | Range | (5-8) | | | (5-10) | (6-9) | |
| Length of Outer Petioles to the joint (cm) | Average | 36.4 | NA | NA | 35.6 | 27.2 | NA |
| | Range | (33.3-43) | | | (33-37.3) | (24.7-29.3) | |
| Width of Outer Petioles at the midrib (mm) | Average | 30.7 | NA | NA | 28.2 | 27.2 | NA |
| | Range | (28.3-33.3) | | | (22.3-31.3) | (24.7-29.3) | |
| Thickness of Outer Petioles at the midrib (mm) | Average | 10.9 | NA | NA | 9.9 | 9.2 | NA |
| | Range | (10-12) | | | (8.7-11.7) | (7.7-10) | |
| Seed Stem Length (cm) | Average | 0.0 | 26.9 | 44.4 | 4.3 | 0.0 | 35.2 |
| Reading Date 1 | Range | (0-0) | (10-40) | (17-53) | (0-20) | (0-0) | (24-56) |
| | Median | 0.0 | 26.5 | 48.0 | 0.5 | 0.0 | 30.5 |
| Petiole Color (Munsell Color Chart) | | 5GY 5/6 | NA | NA | 5gy 7/6 | 5GY 7/8 | NA |
| Leaf Color (Munsell Color Chart) | | 5GY 3/4 | NA | NA | 5gy 3/4 | 5GY 3/4 | NA |
| Petiole Smoothness | | Smooth/ Slight Rib | NA | NA | Smooth/ Slight Rib | Smooth/ Slight Rib | NA |
| Petiole Cup | | Cup | NA | NA | Cup | Cup | NA |
| % Marketable Defects: | | 100% | 10% | 0% | 100% | 100% | 0% |
| % Butt Pith | | 0% | NA | NA | 40% | 0% | NA |
| % Twist | | 0% | NA | NA | 100% | 30% | NA |

| | | Sonora | Conquistador | Command | Mission | Tall Utah 52-70 'R' Strain |
|---|---|---|---|---|---|---|
| Plant Height (cm) | Average | NA | NA | NA | NA | NA |
| | Range | | | | | |
| Whole Plant weight (kg) | Average | NA | NA | NA | NA | NA |
| | Range | | | | | |
| Trimmed Plant Weight (kg @ 35.6 cm) | Average | NA | NA | NA | NA | NA |
| | Range | | | | | |
| Number of Outer Petioles (>35.6 cm) | Average | NA | NA | NA | NA | NA |
| | Range | | | | | |
| Number of Inner Petioles (<35.6 cm) | Average | NA | NA | NA | NA | NA |
| | Range | | | | | |
| Length of Outer Petioles to the joint (cm) | Average | NA | NA | NA | NA | NA |
| | Range | | | | | |
| Width of Outer Petioles at the midrib (mm) | Average | NA | NA | NA | NA | NA |
| | Range | | | | | |
| Thickness of Outer Petioles at the midrib (mm) | Average | NA | NA | NA | NA | NA |
| | Range | | | | | |
| Seed Stem Length (cm) | Average | 31.6 | 36.1 | 32.5 | 28.0 | 56.0 |
| Reading Date 1 | Range | (26-35) | (17-47) | (25-43) | (15-44) | (36-72) |
| | Median | 33.0 | 41.0 | 33.0 | 27.0 | 52.5 |
| Petiole Color (Munsell Color Chart) | | NA | NA | NA | NA | NA |
| Leaf Color (Munsell Color Chart) | | NA | NA | NA | NA | NA |
| Petiole Smoothness | | NA | NA | NA | NA | NA |
| Petiole Cup | | NA | NA | NA | NA | NA |
| % Marketable Defects: | | 0% | 0% | 0% | 0% | 0% |
| % Butt Pith | | NA | NA | NA | NA | NA |
| % Twist | | NA | NA | NA | NA | NA |

As shown in Tables 5A and 5B, under these conditions ADS-20 and TBG 34 were the most bolting tolerant with no seed stem development, followed by Hill's Special. ADS-22 was the next most bolting tolerant followed by TBG 29.

ADS-1 and TBG 28 were very similar and TBG 43 while similar was slightly poorer for seed stem development. TBG 37 was more similar to Sonora and Command for lack of tolerance to bolting. Traditionally Florida varieties do not require significant bolting tolerance and being developed in Florida where bolting pressure is fairly low they traditionally do not have much bolting tolerance. However, some winters in Florida can produce enough cold hours for Florida varieties to bolt so improved bolting tolerance can be critical for varieties planted for spring harvest. Of the Florida developed varieties planted in this trial TBG 31, 32, 35 and ADS-8 were the least tolerant and more risky for spring harvest window with colder production conditions, TBG 53 was more bolting tolerant than its parent TBG 32 and TBG 54 was more bolting tolerant than its sister TBG 31 providing them as better less risk varieties for Florida production in more bolting stressful years.

Tables 6A and 6B shows the result of a trial transplanted in Oxnard, California Dec. 19, 2020, and evaluated Apr. 27, 2021 (129 days). This trial was grown in a normal production field that had moderate to heavy pressure for bolting (1,061 hours below 50° F.), measured by seed stem length. The only characteristics measured for varieties with an average seed stem length of 10 cm and higher were length of outer petioles at the joint and seed stem length. The plant population (58,080 plants to the acre) was higher than the commercial norm of approximately 45,000 to 47,000 plants to the acre.

With the cold hours being so high one would have expected considerably more seed stem development, however, it remained a little lower than the hours would suggest. There are many environmental issues that can alter expected results including cold periods being interrupted by warmer periods which may break the bolting triggers. Full characteristic notes were only taken for more bolting tolerant cultivars (seed stem development of less than 10 cm). C-20 and C-30 were the most bolting tolerant with no seed stem development under these conditions followed by Hill's Special. C-29 was the next most bolting tolerant followed by C-49 and C-45 which were both very similar. C-29 had the highest yield based on average stalk weight, petiole count (outer) and the widest petioles. Next best yielding were C-45 and C-49 based on weight which were similar to C-30, however due to the expanded seed stem weight was likely misstated since considerable weight may be attributed to the seed stem compared to C-30 which has none. C-49 was worse than C-45 for defects. Traditionally Florida varieties do not require significant bolting tolerance and being developed in Florida where bolting pressure is fairly low they traditionally do not have much bolting tolerance. However, some winters in Florida can produce enough cold hours for Florida varieties to bolt so improved bolting tolerance can be critical for varieties planted for spring harvest. Of the Florida developed varieties planted in this trial TBG 31, 32, 35 and ADS-8 were the least tolerant and more risky for spring harvest window with colder production conditions, TBG 53 was slightly more bolting tolerant than its parent TBG 32, TBG 54 was more bolting tolerant than its sister TBG 31 and ADS-23 the least bolting susceptible Florida variety.

TABLE 6A

| | | TBG 54 | TBG 31 | TBG 35 | ADS-8 | TBG 32 | TBG 53 |
|---|---|---|---|---|---|---|---|
| Plant Height (cm) | Average | NA | NA | NA | NA | NA | NA |
| | Range | | | | | | |
| Whole Plant Weight (kg) | Average | NA | NA | NA | NA | NA | NA |
| | Range | | | | | | |
| Trimmed Plant Weight (kg) | Average | NA | NA | NA | NA | NA | NA |
| | Range | | | | | | |
| Number of Outer Petioles | Average | NA | NA | NA | NA | NA | NA |
| | Range | | | | | | |
| Number of Inner Petioles | Average | NA | NA | NA | NA | NA | NA |
| | Range | | | | | | |
| Length of Outer Petioles @ joint (cm) | Average | 35.8 | 40.3 | 37.4 | 33.0 | 41.6 | 45.0 |
| | Range | (33.3-42) | (37-44.7) | (32.7-41.3) | (28.3-36.7) | (38-44.7) | (43.7-46.7) |
| Width of Outer Petioles @ midrib (mm) | Average | NA | NA | NA | NA | NA | NA |
| | Range | | | | | | |
| Thickness of Outer Petioles @ midrib (mm) | Average | NA | NA | NA | NA | NA | NA |
| | Range | | | | | | |
| Seed Stem Length (cm) | Average | 24.6 | 38.7 | 60.4 | 42.6 | 40.1 | 37.6 |
| | Range | (15-40) | (23-65) | (38-83) | (34-52) | (25-61) | (23-49) |
| | Median | 23.5 | 37.5 | 60 | 42 | 39.5 | 37 |
| Petiole Color | | NA | NA | NA | NA | NA | NA |
| Leaf Color | | NA | NA | NA | NA | NA | NA |
| Petiole Smoothness | | NA | NA | NA | NA | NA | NA |
| Petiole Cup | | NA | NA | NA | NA | NA | NA |
| Defects: | | | | | | | |
| % Node Crack | | NA | NA | NA | NA | NA | NA |
| % Butt Crack | | NA | NA | NA | NA | NA | NA |
| % Suckers | | NA | NA | NA | NA | NA | NA |
| % Twist | | NA | NA | NA | NA | NA | NA |
| % Feather Leaf | | NA | NA | NA | NA | NA | NA |

| | | Floribelle | ADS-23 | TBG 45 | TBG 43 | TBG 29 | ADS-1 |
|---|---|---|---|---|---|---|---|
| Plant Height (cm) | Average | NA | NA | 81.7 | 84.6 | 1.65 | NA |
| | Range | | | (76-85) | (68-93) | (1.16-2.04) | |
| Whole Plant Weight (kg) | Average | NA | NA | 1.55 | 1.57 | 1.65 | NA |
| | Range | | | (1.02-2) | (1.28-2) | (1.16-2.04) | |
| Trimmed Plant Weight (kg) | Average | NA | NA | 1.17 | 1.17 | 1.31 | NA |
| | Range | | | (0.78-1.48) | (0.96-1.5) | (0.96-1.62) | |
| Number of Outer | Average | NA | NA | 12.2 | 11.2 | 14.2 | NA |

TABLE 6A-continued

| | | | | | | | |
|---|---|---|---|---|---|---|---|
| Petioles | Range | | | (11-14) | (10-13) | (13-15) | |
| Number of Inner | Average | NA | NA | 8.4 | 9.3 | 10.4 | NA |
| Petioles | Range | | | (6-12) | (8-10) | (9-13) | |
| Length of Outer | Average | 32.6 | 38.7 | 43.1 | 36.0 | 35.0 | 33.3 |
| Petioles @ joint (cm) | Range | (28.7-35.7) | (34.3-43) | (36.7-48) | (31.7-38.7) | (31.3-37.3) | (29.3-37) |
| Width of Outer | Average | NA | NA | 28.4 | 29.0 | 31.8 | NA |
| Petioles @ midrib (mm) | Range | | | (24.3-32) | (25.3-31.7) | (28.0-36.7) | |
| Thickness of Outer | Average | NA | NA | 9.9 | 11.3 | 10.6 | NA |
| Petioles @ midrib (mm) | Range | | | (8.7-11) | (9.7-12.7) | (9.3-11.3) | |
| Seed Stem Length (cm) | Average | 56.1 | 11.9 | 4.7 | 4.7 | 2.5 | 11.1 |
| | Range | (40-86) | (0-21) | (0-14) | (0-16) | (0-5) | (4-21) |
| | Median | 50.5 | 16 | 2.5 | 3.5 | 2.5 | 11 |
| Petiole Color | | NA | NA | 5gy 6/6 | 5gy 6/4 | 5gy 6/6 | NA |
| Leaf Color | | NA | NA | 5gy 3/4 | 5gy 3/4 | 5gy 4/4 | NA |
| Petiole Smoothness | | NA | NA | Smooth/Rib | Smooth | Smooth/Slight Rib | NA |
| Petiole Cup | | NA | NA | Cup | Cup | Slight Cup | NA |
| Defects: | | | | | | | |
| % Node Crack | | NA | NA | 0% | 0 | 0% | NA |
| % Butt Crack | | NA | NA | 0% | 0% | 0% | NA |
| % Suckers | | NA | NA | 70% | 0% | 0% | NA |
| % Twist | | NA | NA | 40% | 30% | 0% | NA |
| % Feather Leaf | | NA | NA | 0% | 0% | 0% | NA |

TABLE 6B

| | | TBG 34 | TBG 37 | TBG 28 | TBG 33 | Hills Special | ADS-20 |
|---|---|---|---|---|---|---|---|
| Plant Height (cm) | Average | 76.2 | 83.8 | NA | NA | 71.5 | 73.0 |
| | Range | (72-80) | (77-91) | | | (69-76) | (70-76) |
| Whole Plant Weight (kg) | Average | 1.57 | 1.46 | NA | NA | 1.25 | 1.21 |
| | Range | (1.06-1.84) | (0.96-2.06) | | | (1.08-1.56) | (1-1.58) |
| Trimmed Plant Weight (kg) | Average | 1.13 | 1.23 | NA | NA | 1.08 | 0.94 |
| | Range | (0.74-1.36) | (0.84-1.64) | | | (0.96-1.34) | (0.74-1.22) |
| Number of Outer Petioles | Average | 11.5 | NA | NA | NA | 9.2 | 11.6 |
| | Range | (9-13) | | | | (8-12) | (10-13) |
| Number of Inner Petioles | Average | 9.2 | NA | NA | NA | 9.2 | 8.7 |
| | Range | (7-12) | | | | (8-12) | (7-10) |
| Length of Outer Petioles @ joint (cm) | Average | 33.1 | 39.2 | 44.1 | 44.3 | 34.6 | 34.3 |
| | Range | (29.7-37) | (34-49) | (39-50) | (41-47.3) | (31.3-37.7) | (32.3-36.7) |
| Width of Outer Petioles @ midrib (mm) | Average | 28.7 | NA | NA | NA | 26.0 | 27.0 |
| | Range | (26.3-32.3) | | | | (23.7-30.7) | (22.7-29.3) |
| Thickness of Outer Petioles @ midrib (mm) | Average | 10.8 | NA | NA | NA | 9.4 | 9.6 |
| | Range | (9.7-12) | | | | (8.3-10.7) | (8.3-11) |
| Seed Stem Length (cm) | Average | 0 | 10.1 | 13.9 | 16.6 | 0.7 | 0 |
| | Range | (0-0) | (0-22) | (2-35) | (8-24) | (0-5) | (0-0) |
| | Median | 0 | 11.5 | 13.5 | 17.5 | 0 | 0 |
| Petiole Color | | 5gy 6/6 | 5gy 6/4 | NA | NA | 5gy 6/6 | 5gy 6/6 |
| Leaf Color | | 5gy 4/4 | 5gy 3/4 | NA | NA | 5gy 4/4 | 5gy 4/4 |
| Petiole Smoothness | | Slight Rib/Rib | Slight Rib/Rib | NA | NA | Smooth | Smooth |
| Petiole Cup | | Cup | Slight Cup/Cup | NA | NA | Cup | Cup |
| Defects: | | | | | | | |
| % Node Crack | | 0% | 30% | NA | NA | 0% | 0 |
| % Butt Crack | | 0% | 10% | NA | NA | 0% | 0% |
| % Suckers | | 60% | 100% | NA | NA | 0% | 20% |
| % Twist | | 60% | 100% | NA | NA | 50% | 0% |
| % Feather Leaf | | 0% | 0% | NA | NA | 0% | 0% |

| | | Challenger | Sonora | Conquistador | Mission | Command |
|---|---|---|---|---|---|---|
| Plant Height (cm) | Average | NA | NA | NA | NA | NA |
| | Range | | | | | |
| Whole Plant Weight (kg) | Average | NA | NA | NA | NA | NA |
| | Range | | | | | |
| Trimmed Plant Weight (kg) | Average | NA | NA | NA | NA | NA |
| | Range | | | | | |
| Number of Outer Petioles | Average | NA | NA | NA | NA | NA |
| | Range | | | | | |
| Number of Inner Petioles | Average | NA | NA | NA | NA | NA |
| | Range | | | | | |
| Length of Outer Petioles @ joint (cm) | Average | 41.8 | 36.8 | 35.5 | 35.8 | 34.4 |
| | Range | (37-47.7) | (34.7-38.7) | (33.3-40) | (33-39) | (31-38.7) |

TABLE 6B-continued

| | | | | | | |
|---|---|---|---|---|---|---|
| Width of Outer Petioles @ midrib (mm) | Average Range | NA | NA | NA | NA | NA |
| Thickness of Outer Petioles @ midrib (mm) | Average Range | NA | NA | NA | NA | NA |
| Seed Stem Length (cm) | Average | 21.9 | 17.5 | 16.7 | 10.3 | 16.6 |
| | Range | (15-34) | (6-35) | (8-33) | (2-21) | (10-31) |
| | Median | 21 | 15 | 16 | 9.5 | 15 |
| Petiole Color | | NA | NA | NA | NA | NA |
| Leaf Color | | NA | NA | NA | NA | NA |
| Petiole Smoothness | | NA | NA | NA | NA | NA |
| Petiole Cup | | NA | NA | NA | NA | NA |
| Defects: | | | | | | |
| % Node Crack | | NA | NA | NA | NA | NA |
| % Butt Crack | | NA | NA | NA | NA | NA |
| % Suckers | | NA | NA | NA | NA | NA |
| % Twist | | NA | NA | NA | NA | NA |
| % Feather Leaf | | NA | NA | NA | NA | NA |

Table 7 shows the result of a trial transplanted in Oxnard, California Mar. 8, 2021, and evaluated Jun. 25, 2021, (109 days) in a normal production field with very low pressure due to *Fusarium oxysporum* race 2, but slight pressure for bolting (442 hours below 50° F.). The plant population (58,080 plants to the acre) was higher than the commercial norm of approximately 45,000 to 47,000 plants to the acre. NA=Not Available.

TABLE 7

| | | TBG 54 | TBG 31 | TBG 35 | TBG 32 | TBG 53 | TBG 37 | TBG 43 |
|---|---|---|---|---|---|---|---|---|
| Plant Height (cm) | Average | 48.8 | 43.6 | NA | 35.4 | 91.8 | 89.0 | 88.9 |
| | Range | (0-85) | (0-89) | | (0-91) | (89-95) | (83-95) | (86-92) |
| Whole Plant weight (kg) | Average | 0.77 | 0.85 | NA | 0.59 | 1.20 | 1.53 | 1.77 |
| | Range | (0-1.55) | (0-2) | | (0-1.72) | (0-1.7) | (1.18-1.86) | (1.48-2.02) |
| Trimmed Plant Weight (kg @ 35.6 cm) | Average | 0.57 | 0.48 | NA | 0.43 | 0.81 | 1.14 | 1.27 |
| | Range | (0-1.18) | (0-1.38) | | (0-1.24) | (0-1.16) | (0.82-1.44) | (1.1-1.46) |
| Number of Outer Petioles (>35.6 cm) | Average | 6.8 | 4.9 | NA | 4.4 | −9.5 | 11.7 | 11.2 |
| | Range | (0-13) | (0-14) | | (0-14) | (0-13) | (9-13) | (10-12) |
| Number of Inner Petioles (<35.6 cm) | Average | 2.2 | 1.7 | NA | 4.4 | 3.3 | 5.2 | 5.2 |
| | Range | (0-5) | (0-6) | | (0-14) | (0-5) | (4-6) | (4-6) |
| Length of Outer Petioles to the joint (cm) | Average | 17.9 | 13.7 | NA | 14.0 | 27.5 | 34.4 | 30.2 |
| | Range | (0-33.3) | (0-37.3) | | (0-37) | (0-38) | (30.7-38.7) | (28-31.7) |
| Width of Outer Petioles at the midrib (mm) | Average | 14.2 | 10.1 | NA | 10.6 | 19.7 | 25.3 | 28.3 |
| | Range | (0-25.7) | (0-26.7) | | (0-29.7) | (0-25.7) | (22.3-27) | (25.3-30.3) |
| Thickness of Outer Petioles at the midrib (mm) | Average | 6.5 | 4.7 | NA | 4.7 | 8.6 | 10.3 | 12.5 |
| | Range | (0-12.7) | (0-13.3) | | (0-12.3) | (0-12) | (9.3-11.7) | (12-13.3) |
| Seed Stem Length (cm) Reading Date 1 | Average | 23.2 | 43.7 | 118.7 | 68.3 | 13.1 | 0.5 | 0.0 |
| | Range | (0-71) | (0-96) | (99-140) | (0-131) | (0-80) | (0-4) | (0-0) |
| | Median | 16.0 | 53.5 | 118.0 | 84.0 | 0.8 | 0.0 | 0.0 |
| Petiole Color (Munsell Color Chart) | | 5gy 7/6 | 5gy 7/6 | NA | 5 gy 7/6 | 5gy 6/6 | 5gy 6/6 | 5gy 6/6 |
| Leaf Color (Munsell Color Chart) | | 5gy 4/4 | 5gy 4/4 | NA | 5gy 4/4 | 5gy 4/4 | 5gy 3/4 | 5gy 3/4 |
| Petiole Smoothness | | Smooth | Smooth | NA | Smooth | Smooth | Smooth | Smooth |
| Petiole Cup | | Cup | Cup | NA | Slight Cup | Slight Cup | Cup | Cup |
| % Marketable | | 0% | 0% | 0% | 30% | 80% | 100% | 100% |
| Defects: | | | | | | | | |
| % Top Pith | | 100% | 100% | NA | 100% | 20% | 0% | 0% |
| % Butt Pith | | 40% | 100% | NA | 80% | 20% | 0% | 0% |
| % Node Crack | | 0% | 0% | NA | 0% | 10% | 0% | 0% |
| % Butt Crack | | 0% | 10% | NA | 0% | 0% | 0% | 0% |
| % Suckers | | 40% | 40% | NA | 60% | 20% | 0% | 0% |
| % Feather Leaf | | 0% | 0% | NA | 0% | 0% | 0% | 0% |
| % Twist | | 0% | 40% | NA | 60% | 20% | 40% | 10% |
| % Black Heart | | 0% | 10% | NA | 0% | 0% | 0% | 0% |
| % Brown Stem | | 80% | 30% | NA | 70% | 20% | 10% | 0% |

| | | TBG 45 | TBG 29 | ADS-1 | TBG 34 | TBG 28 |
|---|---|---|---|---|---|---|
| Plant Height (cm) | Average | 83.4 | 80.5 | 80.2 | 80.4 | 97.5 |
| | Range | (82-88) | (78-83) | (75-85) | (77-84) | (94-104) |
| Whole Plant weight (kg) | Average | 1.76 | 1.87 | 1.69 | 1.27 | 1.72 |
| | Range | (1.46-2.1) | (1.6-2.28) | (1.46-2.12) | (0.98-1.62) | (1.32-2.12) |

TABLE 7-continued

| | | | | | | |
|---|---|---|---|---|---|---|
| Trimmed Plant Weight | Average | 1.29 | 1.42 | 1.31 | 0.94 | 1.25 |
| (kg @ 35.6 cm) | Range | (1.06-1.52) | (1.22-1.74) | (1.1-1.6) | (0.76-1.18) | (0.94-1.5) |
| Number of Outer | Average | 12.1 | 12.0 | 10.5 | 9.6 | 12.9 |
| Petioles (>35.6 cm) | Range | (10-14) | (10-14) | (9-12) | (8-11) | (11-16) |
| Number of Inner | Average | 4.5 | 4.9 | 6.1 | 3.3 | 5.6 |
| Petioles (<35.6 cm) | Range | (3-5) | (4-8) | (5-7) | (3-4) | (4-7) |
| Length of Outer | Average | 31.3 | 26.9 | 29.4 | 31.0 | 38.9 |
| Petioles to the | Range | (28-36.3) | (18-30.3) | (26.3-31.7) | (28.7-33.7) | (36.3-40.7) |
| joint (cm) | | | | | | |
| Width of Outer | Average | 27.3 | 30.3 | 26.8 | 27.1 | 28.1 |
| Petioles at the | Range | (24.3-29) | (28.7-33.7) | (22.3-29.3) | (26-28.7) | (26.7-29.7) |
| midrib (mm) | | | | | | |
| Thickness of Outer | Average | 11.0 | 12.6 | 12.0 | 11.0 | 11.9 |
| Petioles at the | Range | (10-12) | (11.3-14) | (10.3-13) | (9.7-12.3) | (11-13) |
| midrib (mm) | | | | | | |
| Seed Stem Length | Average | 0.0 | 0.0 | 1.3 | 0.0 | 0.0 |
| (cm) Reading | Range | (0-0) | (0-0) | (0-11) | (0-0) | (0-0) |
| Date 1 | Median | 0.0 | 0.0 | 0.0 | 0.0 | 0.0 |
| Petiole Color | | 5gy 6/6 | 5gy 7/6 | 5gy 6/6 | 5gy 6/6 | 5gy 6/6 |
| (Munsell Color Chart) | | | | | | |
| Leaf Color | | 5gy 3/4 | 5gy 3/4 | 5gy 3/4 | 5gy 3/4 | 5gy 3/4 |
| (Munsell Color Chart) | | | | | | |
| Petiole | | Slight | Smooth/ | Smooth | Smooth | Smooth |
| Smoothness | | Rib/Rib | Slight Rib | | | |
| Petiole Cup | | Slight | Slight Cup | Cup/Deep | Cup | Cup |
| | | Cup/Cup | | Cup | | |
| % Marketable | | 100% | 100% | 100% | 100% | 100% |
| Defects: | | | | | | |
| % Top Pith | | 0% | 0% | 0% | 100% | 0% |
| % Butt Pith | | 0% | 0% | 0% | 0% | 0% |
| % Node Crack | | 0% | 20% | 0% | 30% | 0% |
| % Butt Crack | | 0% | 0% | 0% | 0% | 0% |
| % Suckers | | 20% | 0% | 0% | 10% | 0% |
| % Feather Leaf | | 20% | 30% | 0% | 0% | 0% |
| % Twist | | 0% | 0% | 0% | 20% | 100% |
| % Black Heart | | 0% | 0% | 0% | 0% | 0% |
| % Brown Stem | | 0% | 0% | 0% | 0% | 0% |

As shown in Table 7, under the slight bolting pressure that this trial experienced varieties specially developed for production in Florida had significant seed stem development (TBG 35, TBG 31, TBG 32, TBG 54). Except for ADS-1 there was very little impact on the remaining varieties which had been developed for production in California. Under these conditions TBG 29 out yielded all varieties (trimmed plant weight) and TBG 45, TBG 43, ADS-1 and TBG 28 were very similar and next in line for trimmed weight. However, it and TBG 45 were impacted more by feather leaves. TBG 28 performed as it would normally producing the tallest plants with the longest petioles to the joint followed by TBG 37; however, both also had more petiole twisting. TBG 45, TBG 29 and TBG 28 were similar in producing an average 12 or more petioles longer than 35.6 cm. ADS-1 and TBG 43 appeared to be most similar with one another for most of their characteristics and the two that were most free from defects. Traditionally Florida varieties do not require significant bolting tolerance and being developed in Florida where bolting pressure is fairly low they traditionally do not have much bolting tolerance. However, some winters in Florida can produce enough cold hours for Florida varieties to bolt so improved bolting tolerance can be critical for varieties planted for spring harvest. Of the Florida developed varieties planted in this trial TBG 31, 32 and 35 were the least tolerant and more risky for spring harvest window with colder winter production conditions, TBG 53 was more bolting tolerant than its parent TBG 32, TBG 54 was more bolting tolerant than its sister TBG 31 as measured by seed stem length.

Tables 8-9 show the results of trials grown in fields in Oxnard, California that have Fusarium oxysporum race 2 present. The field represented by the results presented in Table 8 was a field that was created with especially high inoculum levels of Fusarium oxysporum race 2 inoculums in order to develop and evaluate cultivars for tolerance. As indicated above, this same trial coincidentally had sufficient cold hour accumulation to induce bolting in many varieties. The field represented by the results in Table 9 also had fairly high levels Fusarium oxysporum race 2 inoculums.

In both trials, Tables 8 and 9, TBG 54 was very susceptible to fusarium race 2, as indicated by the fusarium ratings, and slightly more susceptible than its sister TBG 31. While fusarium race 2 is not currently an issue in Florida, this information does demonstrate that TBG 54 is not appropriate for production in Michigan or California where the disease is endemic.

Tables 8A and 8B show the result of a trial transplanted in Oxnard, California Mar. 17, 2021, and evaluated Jun. 27, 2021, (102 days). This trial was grown in a production block that has been developed with especially high levels of Fusarium oxysporum race 2 in order to evaluate and develop varieties for increased tolerance to the disease. The celery in this trial was also exposed to slight pressure for bolting (442 hours below 50° F.). The plant population (58,080 plants to the acre) was higher than the commercial norm of approximately 45,000 to 47,000 plants to the acre.

TABLE 8A

| | | TBG 54 | TBG 31 | TBG 35 | TBG 32 | TBG 53 | ADS-23 |
|---|---|---|---|---|---|---|---|
| Plant Height (cm) | Average | 26.5 | NA | NA | NA | NA | 22.9 |
| | Range | (20-35) | | | | | (0-42) |
| Whole Plant weight (kg) | Average | NA | NA | NA | NA | NA | NA |
| | Range | | | | | | |
| Trimmed Plant Weight (kg @ 35.6 cm) | Average | NA | NA | NA | NA | NA | NA |
| | Range | | | | | | |
| Number of Outer Petioles (>35.6 cm) | Average | NA | NA | NA | NA | NA | NA |
| | Range | | | | | | |
| Number of Inner Petioles (<35.6 cm) | Average | NA | NA | NA | NA | NA | NA |
| | Range | | | | | | |
| Length of Outer Petioles to the joint (cm) | Average | NA | NA | NA | NA | NA | NA |
| | Range | | | | | | |
| Width of Outer Petioles at the midrib (mm) | Average | NA | NA | NA | NA | NA | NA |
| | Range | | | | | | |
| Thickness of Outer Petioles at the midrib (mm) | Average | NA | NA | NA | NA | NA | NA |
| | Range | | | | | | |
| Seed Stem Length (cm) | Average | 28.4 | 78.2 | 26.9 | 63.2 | 44.2 | 18.6 |
| | Range | (10-53) | (55-101) | (0-58) | (0-88) | (0-55) | (0-41) |
| | Median | 26.0 | 78.0 | 34.5 | 76.0 | 49.0 | 14.5 |
| Petiole Color (Munsell Color Chart) | | NA | NA | NA | NA | NA | NA |
| Leaf Color (Munsell Color Chart) | | NA | NA | NA | NA | NA | NA |
| Petiole Smoothness | | NA | NA | NA | NA | NA | NA |
| Petiole Cup | | NA | NA | NA | NA | NA | NA |
| % Marketable | | 0% | 0% | 0% | 0% | 0% | 0% |
| Disease: | | | | | | | |
| Overall Fusarium Ratings [0 to 5 (0 = dead, 5 = tolerant)] | Average | 1 | 1.5 | 1 | 1 | 1 | 1 |
| | Range | 0-1 | 1-2 | 0-1 | 0-1 | 0-1 | 0-1 |
| Root Fusarium Ratings [0 to 5 (0 = dead, 5 = tolerant)] | Average | 1 | 1 | 1 | 1 | 1 | 1 |
| | Range | 0-1 | 1-2 | 0-1 | 0-1 | 0-1 | 0-1 |

| | | Floribelle | TBG 43 | TBG 45 | TBG 29 |
|---|---|---|---|---|---|
| Plant Height (cm) | Average | 17.0 | 71.7 | 81.2 | 70.1 |
| | Range | (0-27) | (68-75) | (77-86) | (62-74) |
| Whole Plant weight (kg) | Average | NA | 1.42 | 1.37 | 1.25 |
| | Range | | (1.18-1.78) | (1.06-1.64) | (1.02-1.52) |
| Trimmed Plant Weight (kg @ 35.6 cm) | Average | NA | 1.12 | 1.03 | 1.01 |
| | Range | | (1-1.38) | (0.8-1.2) | (0.84-1.28) |
| Number of Outer Petioles (>35.6 cm) | Average | NA | 12.7 | 12.4 | 12.4 |
| | Range | | (11-17) | (11-13) | (10-14) |
| Number of Inner Petioles (<35.6 cm) | Average | NA | 4.8 | 4.4 | 6.1 |
| | Range | | (3-6) | (3-6) | (5-8) |
| Length of Outer Petioles to the joint (cm) | Average | NA | 24.5 | 30.2 | 24.4 |
| | Range | | (23-26.7) | (28-32.3) | (21.7-26) |
| Width of Outer Petioles at the midrib (mm) | Average | NA | 27.9 | 25.8 | 27.2 |
| | Range | | (25.7-29.7) | (23.7-28.3) | (20-30.7) |
| Thickness of Outer Petioles at the midrib (mm) | Average | NA | 11.3 | 11.7 | 10.4 |
| | Range | | (10-12.7) | (10.3-14) | (9.3-11.7) |
| Seed Stem Length (cm) | Average | 20.0 | 0.0 | 0.0 | 0.0 |
| | Range | (0-70) | (0-0) | (0-0) | (0-0) |
| | Median | 8.5 | 0.0 | 0.0 | 0.0 |
| Petiole Color (Munsell Color Chart) | | NA | 5gy 6/6 | 5gy 6/6 | 5gy 6/6 |
| Leaf Color (Munsell Color Chart) | | NA | 5gy 3/4 | 5gy 3/4 | 5gy 3/4 |
| Petiole Smoothness | | NA | Smooth | Smooth | Smooth/Slight Rib |
| Petiole Cup | | NA | Cup | Slight Cup/Cup | Slight Cup |
| % Marketable | | 0% | 90% | 40% | 90% |
| Disease: | | | | | |
| Overall Fusarium Ratings [0 to 5 (0 = dead, 5 = tolerant)] | Average | 1 | 5 | 5 | 4 |
| | Range | 0-1 | 5 | 5 | 4-5 |
| Root Fusarium Ratings [0 to 5 (0 = dead, | Average | 1 | 5 | 5 | 4 |
| | Range | 0-1 | 4-5 | 5 | 3-4 |

TABLE 8A-continued

5 = tolerant)]

TABLE 8B

| | | ADS-1 | TBG 34 | TBG 37 | TBG 28 | Challenger |
|---|---|---|---|---|---|---|
| Plant Height (cm) | Average | 33.7 | 49.2 | 79.6 | 76.5 | NA |
| | Range | (24-38) | (41-67) | (74-88) | (70-81) | |
| Whole Plant weight (kg) | Average | NA | NA | 1.37 | 1.16 | NA |
| | Range | | | (1.18-1.58) | (0.96-1.5) | |
| Trimmed Plant Weight (kg @ 35.6 cm) | Average | NA | NA | 0.95 | 0.89 | NA |
| | Range | | | (0-1.14) | (0.76-1.14) | |
| Number of Outer Petioles (>35.6 cm) | Average | NA | NA | 11.3 | 16.8 | NA |
| | Range | | | (0-15) | (15-20) | |
| Number of Inner Petioles (<35.6 cm) | Average | NA | NA | 4.6 | 4.6 | NA |
| | Range | | | (0-6) | (4-6) | |
| Length of Outer Petioles to the joint (cm) | Average | 14.4 | 16.7 | NA | 31.1 | NA |
| | Range | (11.7-17.3) | (10-21) | | (28-34.3) | |
| Width of Outer Petioles at the midrib (mm) | Average | NA | NA | 24.0 | 23.4 | NA |
| | Range | | | (0-30) | (19.7-25.3) | |
| Thickness of Outer Petioles at the midrib (mm) | Average | NA | NA | 9.0 | 9.5 | NA |
| | Range | | | (0-11.3) | (8-10.3) | |
| Seed Stem Length (cm) | Average | 0.0 | 0.0 | 7.7 | 0.0 | 62.4 |
| | Range | (0-0) | (0-0) | (0-41) | (0-0) | (32-86) |
| | Median | 0.0 | 0.0 | 1.5 | 0.0 | 60.5 |
| Petiole Color (Munsell Color Chart) | | 5gy 6/6 | NA | 5gy 6/6 | 5gy 7/6 | NA |
| Leaf Color (Munsell Color Chart) | | 5gy 3/4 | NA | 5gy 3/4 | 5gy 3/4 | NA |
| Petiole Smoothness | | Smooth/ Slight Rib/Rib | NA | 0 | Smooth/ Slight Rib | NA |
| Petiole Cup | | Cup | NA | Slight Cup/Cup | Slight Cup | NA |
| % Marketable | | 0% | 0% | 80% | 30% | 0% |
| Disease: | | | | | | |
| Overall Fusarium Ratings [0 to 5 (0 = dead, 5 = tolerant)] | Average | 1.5 | 2 | 4.5 | 5 | 3 |
| | Range | 1-2 | 1-2 | 4-5 | 5 | 3-4 |
| Root Fusarium Ratings [0 to 5 (0 = dead, 5 = tolerant)] | Average | 1 | 1.5 | 3.5 | 4.5 | 3 |
| | Range | 1 | 1-3 | 3-4 | 4-5 | 1-4 |

| | | Sonora | Conquistador | Command | Mission | Tall Utah 52-75 |
|---|---|---|---|---|---|---|
| Plant Height (cm) | Average | 24.7 | 20.6 | 50.9 | 22.6 | 17.5 |
| | Range | (0-40) | (0-32) | (47-62) | (0-40) | (0-37) |
| Whole Plant weight (kg) | Average | NA | NA | NA | NA | NA |
| | Range | | | | | |
| Trimmed Plant Weight (kg @ 35.6 cm) | Average | NA | NA | NA | NA | NA |
| | Range | | | | | |
| Number of Outer Petioles (>35.6 cm) | Average | NA | NA | NA | NA | NA |
| | Range | | | | | |
| Number of Inner Petioles (<35.6 cm) | Average | NA | NA | NA | NA | NA |
| | Range | | | | | |
| Length of Outer Petioles to the joint (cm) | Average | 11.0 | 7.2 | 18.2 | 10.5 | 8.1 |
| | Range | (0-19.7) | (0-14) | (16-21) | (0-19) | (0-15.7) |
| Width of Outer Petioles at the midrib (mm) | Average | NA | NA | NA | NA | NA |
| | Range | | | | | |
| Thickness of Outer Petioles at the midrib (mm) | Average | NA | NA | NA | NA | NA |
| | Range | | | | | |
| Seed Stem Length (cm) | Average | 0.0 | 0.0 | 0.0 | 0.0 | 0.0 |
| | Range | (0-0) | (0-0) | (0-0) | (0-0) | (0-0) |
| | Median | 0.0 | 0.0 | 0.0 | 0.0 | 0.0 |
| Petiole Color (Munsell Color Chart) | | NA | NA | NA | NA | NA |
| Leaf Color (Munsell Color Chart) | | NA | NA | NA | NA | NA |
| Petiole Smoothness | | NA | NA | NA | NA | NA |

TABLE 8B-continued

| Petiole Cup | | NA | NA | NA | NA | NA |
|---|---|---|---|---|---|---|
| % Marketable | | 0% | 0% | 0% | 0% | 0% |
| Disease: | | | | | | |
| Overall Fusarium Ratings | Average | 1 | 1 | 2.5 | 1 | 1 |
| [0 to 5 (0 = dead, | Range | 0-1 | 0-1 | 2-3 | 0-2 | 0-1 |
| 5 = tolerant)] | | | | | | |
| Root Fusarium Ratings | Average | 1 | 1 | 2 | 1 | 1 |
| [0 to 5 (0 = dead, | Range | 0-1 | 0-1 | 1-3 | 0-1.5 | 0-1 |
| 5 = tolerant)] | | | | | | |

As shown in Tables 8A and 8B, under the *Fusarium oxysporum* race 2 conditions present in this trial C-45, C49 and C-36 showed the best tolerance when ratings for overall and root infection are considered. These were followed by C-37 and C-29. While the Florida varieties (TBG 35, TBG 31, TBG 54, TBG 32, TBG 53, ADS-23 and Floribelle) showed no tolerance to *fusarium* there were some differences for bolting tolerance. Traditionally Florida varieties do not require significant bolting tolerance and being developed in Florida where bolting pressure is fairly low, they traditionally do not have much bolting tolerance. However, some winters in Florida can produce enough cold hours for Florida varieties to bolt so improved bolting tolerance can be critical for varieties planted for spring harvest. Of the Florida developed varieties planted in this trial TBG 31, 32, 35 and ADS-8 were the least tolerant and more risky for spring harvest window with colder production conditions, TBG 53 was more bolting tolerant than its parent TBG 32, TBG 54 was more bolting tolerant than its sister TBG 31 and ADS-23 the least bolting susceptible Florida variety as measured by seed stem length.

Tables 9A and 9B show the result of a trial transplanted in Oxnard, California Aug. 6, 2020, and evaluated Nov. 5, 2020 (91 days). This trial was grown in a production block that has fairly high levels of *Fusarium oxysporum* race 2. Under these conditions we were able to evaluate varieties for relative tolerance to the disease. The plant population (58, 080 plants to the acre) was higher than the commercial norm of approximately 45,000 to 47,000 plants to the acre.

TABLE 9A

| | | TBG 54 | TBG 31 | TBG 35 | Floribelle | ADS-23 | TBG 32 | TBG 37 |
|---|---|---|---|---|---|---|---|---|
| Plant Height (cm) | Average | 26.1 | 37.6 | 23.8 | 12.3 | 41.6 | 29.9 | 78.1 |
| | Range | (0-45) | (0-56) | (0-34) | (0-37) | (0-60) | (0-49) | (75-82) |
| Whole Plant | Average | NA | NA | NA | NA | NA | NA | 1.06 |
| weight (kg) | Range | | | | | | | (0.92-1.49) |
| Trimmed Plant Weight | Average | NA | NA | NA | NA | NA | NA | 0.84 |
| (kg @ 35.6 cm) | Range | | | | | | | (0.71-1.11) |
| Number of Outer | Average | NA | NA | NA | NA | NA | NA | 11.1 |
| Petioles (>35.6 cm) | Range | | | | | | | (9-12) |
| Number of Inner | Average | NA | NA | NA | NA | NA | NA | 5.2 |
| Petioles (<35.6 cm) | Range | | | | | | | (4-6) |
| Length of Outer | Average | 15.0 | 17.0 | 9.7 | 6.1 | 18.4 | 13.5 | 29.7 |
| Petioles to the | Range | (0-27.7) | (0-26) | (0-14.3) | (0-18.7) | (0-26.7) | (0-23) | (26.7-33) |
| joint (cm) | | | | | | | | |
| Width of Outer | Average | NA | NA | NA | NA | NA | NA | 21.7 |
| Petioles at the | Range | | | | | | | (19-25) |
| midrib (mm) | | | | | | | | |
| Thickness of Outer | Average | NA | NA | NA | NA | NA | NA | 10.9 |
| Petioles at the | Range | | | | | | | (10.3-12) |
| midrib (mm) | | | | | | | | |
| Petiole Color | | NA | NA | NA | NA | NA | NA | 5gy 7/6 |
| (Munsell Color Chart) | | | | | | | | |
| Leaf Color | | NA | NA | NA | NA | NA | NA | 5gy 3/4 |
| (Munsell Color Chart) | | | | | | | | |
| Petiole Smoothness | | NA | NA | NA | NA | NA | NA | Smooth |
| Petiole Cup | | NA | NA | NA | NA | NA | NA | Cup |
| % Marketable | | 0% | 0% | 0% | 0% | 0% | 0% | 100% |
| Disease: | | | | | | | | |
| Overall Fusarium Ratings | Average | 1 | 2.5 | 1 | 1 | 1 | 2 | 5 |
| [0 to 5 (0 = dead, | Range | 0-2 | 0-3 | 0-1 | 0-2 | 0-2 | 0-3 | 5 |
| 5 = tolerant)] | | | | | | | | |
| Defects: | | | | | | | | |
| % Top Pith | | NA | NA | NA | NA | NA | NA | 0% |
| % Butt Pith | | NA | NA | NA | NA | NA | NA | 0% |
| % Butt Crack | | NA | NA | NA | NA | NA | NA | 0% |
| % Twist | | NA | NA | NA | NA | NA | NA | 0% |
| % Black Heart | | NA | NA | NA | NA | NA | NA | 0% |

| | | TBG 43 | TBG 45 | TBG 29 | ADS-1 | TBG 34 |
|---|---|---|---|---|---|---|
| Plant Height (cm) | Average | 77.7 | 78.7 | 71.8 | 50.0 | 50.4 |
| | Range | (71-84) | (72-84) | (67-74) | (42-59) | (44-54) |

TABLE 9A-continued

|  |  |  |  |  |  |  |
|---|---|---|---|---|---|---|
| Whole Plant | Average | 1.08 | 1.22 | 1.07 | NA | NA |
| weight (kg) | Range | (0.77-1.37) | (0.79-1.56) | (0.77-1.33) |  |  |
| Trimmed Plant Weight | Average | 0.85 | 0.93 | 0.92 | NA | NA |
| (kg @ 35.6 cm) | Range | (0.59-1.04) | (0.64-1.14) | (0.63-1.1) |  |  |
| Number of Outer | Average | 11.1 | 11.7 | 12.3 | NA | NA |
| Petioles (>35.6 cm) | Range | (8-13) | (8-14) | (10-14) |  |  |
| Number of Inner | Average | 5.0 | 4.6 | 5.5 | NA | NA |
| Petioles (<35.6 cm) | Range | (4-6) | (4-6) | (5-6) |  |  |
| Length of Outer | Average | 27.3 | 30.1 | 25.1 | 17.6 | 23.0 |
| Petioles to the | Range | (24-29.3) | (28-32) | (23.3-28) | (14.3-21) | (18.3-27.7) |
| joint (cm) |  |  |  |  |  |  |
| Width of Outer | Average | 22.5 | 22.8 | 23.3 | NA | NA |
| Petioles at the | Range | (19.7-25.3) | (20-24.7) | (20.7-25) |  |  |
| midrib (mm) |  |  |  |  |  |  |
| Thickness of Outer | Average | 11.5 | 10.7 | 11.1 | NA | NA |
| Petioles at the | Range | (9.3-13.3) | (9.3-11.3) | (9.7-13) |  |  |
| midrib (mm) |  |  |  |  |  |  |
| Petiole Color | | 5gy 7/6 | 5gy 7/8 | 5gy 7/4 | NA | NA |
| (Munsell Color Chart) |  |  |  |  |  |  |
| Leaf Color | | 5gy 3/4 | 5gy 3/4 | 5gy 3/4 | NA | NA |
| (Munsell Color Chart) |  |  |  |  |  |  |
| Petiole Smoothness | | Smooth | Slight Rib/Rib | Slight Rib/Rib | NA | NA |
| Petiole Cup | | Cup | Cup | Cup | NA | NA |
| % Marketable | | 100% | 100% | 100% | 0% | 0% |
| Disease: |  |  |  |  |  |  |
| Overall Fusarium Ratings | Average | 5 | 5 | 5 | 2.5 | 2.5 |
| [0 to 5 (0 = dead, | Range | 5 | 5 | 5 | 2-3 | 2-3 |
| 5 = tolerant)] |  |  |  |  |  |  |
| Defects: |  |  |  |  |  |  |
| % Top Pith | | 0% | 0% | 0% | NA | NA |
| % Butt Pith | | 0% | 0% | 0% | NA | NA |
| % Butt Crack | | 0% | 0% | 0% | NA | NA |
| % Twist | | 0% | 0% | 0% | NA | NA |
| % Black Heart | | 0% | 0% | 0% | NA | NA |

TABLE 9B

|  |  | TBG 28 | TBG 33 | ADS-22 | Hill's Special | ADS-20 | Challenger | Sonora |
|---|---|---|---|---|---|---|---|---|
| Plant Height (cm) | Average | 73.3 | 68.1 | 72.3 | 47.6 | 36.7 | 77.5 | 21.0 |
|  | Range | (57-87) | (64-72) | (62-82) | (43-54) | (28-46) | (64-87) | (0-34) |
| Whole Plant | Average | 0.38 | 0.76 | 0.81 | NA | NA | 1.08 | NA |
| weight (kg) | Range | (0-1.4) | (0.19-1.2) | (0.67-1.07) |  |  | (0.41-1.61) |  |
| Trimmed Plant Weight | Average | 0.29 | 0.71 | 0.69 | NA | NA | 0.89 | NA |
| (kg @ 35.6 cm) | Range | (0-1.03) | (0.38-0.99) | (0.57-0.9) |  |  | (0.63-1.23) |  |
| Number of Outer | Average | 3.3 | 11.6 | 10.2 | NA | NA | 10.5 | NA |
| Petioles (>35.6 cm) | Range | (0-13) | (9-14) | (9-12) |  |  | (8-13) |  |
| Number of Inner | Average | 1.8 | 4.4 | 6.3 | NA | NA | 7.4 | NA |
| Petioles (<35.6 cm) | Range | (0-7) | (3-6) | (4-10) |  |  | (5-9) |  |
| Length of Outer | Average | 27.5 | 23.3 | 21.6 | 21.3 | 16.0 | 29.2 | 7.8 |
| Petioles to the | Range | (19-33) | (21-25) | (21-22.3) | (17.3-25.3) | (13-20) | (23.7-34.7) | (0-13) |
| joint (cm) |  |  |  |  |  |  |  |  |
| Width of Outer | Average | 7.1 | 19.7 | 23.1 | NA | NA | 20.9 | NA |
| Petioles at the | Range | (0-25) | (16.7-21.3) | (21-24.7) |  |  | (14.7-24.3) |  |
| midrib (mm) |  |  |  |  |  |  |  |  |
| Thickness of Outer | Average | 3.8 | 9.9 | 9.4 | NA | NA | 10.4 | NA |
| Petioles at the | Range | (0-13.3) | (8.7-10.7) | (7.7-10.3) |  |  | (5-12.7) |  |
| midrib (mm) |  |  |  |  |  |  |  |  |
| Petiole Color | | 5gy 7/6 | 5gy 7/6 | 5gy 7/6 | NA | NA | 5gy 7/6 | NA |
| (Munsell Color Chart) |  |  |  |  |  |  |  |  |
| Leaf Color | | 5gy 3/4 | 5gy 3/4 | 5gy 3/4 | NA | NA | 5gy 3/4 | NA |
| (Munsell Color Chart) |  |  |  |  |  |  |  |  |
| Petiole Smoothness | | Smooth | Slight Rib/Rib | Smooth | NA | NA | Smooth | NA |
| Petiole Cup | | Cup | Cup | Cup | NA | NA | Cup/Deep Cup | NA |
| % Marketable | | 30% | 70% | 100% | 0% | 0% | 70% | 0% |
| Disease: |  |  |  |  |  |  |  |  |
| Overall Fusarium Ratings | Average | 4.5 | 4 | 5 | 3 | 2 | 4 | 1 |
| [0 to 5 (0 = dead, | Range | 3-5 | 3-5 | 5 | 2-3 | 1-2 | 3-5 | 0-2 |
| 5 = tolerant)] |  |  |  |  |  |  |  |  |
| Defects: |  |  |  |  |  |  |  |  |

65 66

TABLE 9B-continued

| | | | | | | | |
|---|---|---|---|---|---|---|---|
| % Top Pith | 0% | 0% | 0% | NA | NA | 10% | NA |
| % Butt Pith | 0% | 0% | 0% | NA | NA | 10% | NA |
| % Butt Crack | 50% | 0% | 0% | NA | NA | 30% | NA |
| % Twist | 70% | 0% | 0% | NA | NA | 100% | NA |
| % Black Heart | 0% | 0% | 0% | NA | NA | 10% | NA |

| | | Conquistador | Command | Mission | Tall Utah 52-70 'R' Strain | Tall Uah 5275 |
|---|---|---|---|---|---|---|
| Plant Height (cm) | Average | 32.1 | 51.3 | 32.9 | 17.0 | 24.5 |
| | Range | (0-49) | (38-60) | (0-45) | (0-32) | (0-37) |
| Whole Plant weight (kg) | Average Range | NA | NA | NA | NA | NA |
| Trimmed Plant Weight (kg @ 35.6 cm) | Average Range | NA | NA | NA | NA | NA |
| Number of Outer Petioles (>35.6 cm) | Average Range | NA | NA | NA | NA | NA |
| Number of Inner Petioles (<35.6 cm) | Average Range | NA | NA | NA | NA | NA |
| Length of Outer Petioles to the joint (cm) | Average Range | 13.1 (0-21) | 19.5 (11-24.3) | 14.3 (0-21.7) | 6.2 (0-12.7) | 8.6 (0-14) |
| Width of Outer Petioles at the midrib (mm) | Average Range | NA | NA | NA | NA | NA |
| Thickness of Outer Petioles at the midrib (mm) | Average Range | NA | NA | NA | NA | NA |
| Petiole Color (Munsell Color Chart) | | NA | NA | NA | NA | NA |
| Leaf Color (Munsell Color Chart) | | NA | NA | NA | NA | NA |
| Petiole Smoothness | | NA | NA | NA | NA | NA |
| Petiole Cup | | NA | NA | NA | NA | NA |
| % Marketable | | 0% | 0% | 0% | 0% | 0% |
| Disease: | | | | | | |
| Overall Fusarium Ratings [0 to 5 (0 = dead, 5 = tolerant)] | Average Range | 1 0-2 | 3 2-3 | 1.5 0-2 | 1 0-1 | 1 0-2 |
| Defects: | | | | | | |
| % Top Pith | | NA | NA | NA | NA | NA |
| % Butt Pith | | NA | NA | NA | NA | NA |
| % Butt Crack | | NA | NA | NA | NA | NA |
| % Twist | | NA | NA | NA | NA | NA |
| % Black Heart | | NA | NA | NA | NA | NA |

As shown in Tables 9A and 9B, Under the *Fusarium oxysporum* race 2 conditions present in this trial TBG 43, TBG 45, TBG 29 and TBG 37 showed the best tolerance to *Fusarium oxysporum* race 2 when overall infection ratings and percent marketability were considered. These were followed by TBG 28 and Challenger which also had other major defects that impacted marketability; some as a result of the *fusarium* infection. TBG 45 and TBG 29 looked most similar when comparing trim plant though TBG 45 had more initial untrimmed weight which may have been due to its greater plant height and length to first joint which were more similar to TBG 37. However, TBG 37, TBG 43 and TBG 29 were very similar in slightly lower trimmed weight. TBG 45 and TBG 29 were also more similar for ribbiness. Of the six Florida varieties (TBG 31, 32, 35, 54, ADS-23 and Floribelle) in the trial TBG 31 and TBG 32 showed slightly more tolerance but were unmarketable. TBG 54 performed poorer than sister TBG 31 but were similarly unmarketable. Fortunately, this disease has not been an issue in Florida production.

Table 10 shows the results of a trial that was grown in an Oxnard, California production field that had lower/moderate level of *Fusarium oxysporum* race 2 inoculums and slight bolting pressure that induced bolting in several of the Florida varieties as well as the traditional Western bolting susceptible check variety, Tall Utah 52-70 'R' Strain. Both levels were sufficiently low to allow the Florida varieties to demonstrate better differentiation for both bolting and their *fusarium* race 2 tolerance tendencies.

Under these conditions both TBG 54 and TBG 53 demonstrated improved bolting tolerance compared to their respective relatives TBG 31 and TBG 32, as measured by length of seed stem. TBG 35 was also improved compared to ADS-8 under these low bolting pressure thresholds.

The trial results in Table 10 and the low *fusarium* race 2 infection rates reiterates the results observed in Table 8 and Table 9 where TBG 54 is slightly worse than TBG 31 as demonstrated by *fusarium* ratings. However, TBG 54 did have slightly higher marketability but due to its improved bolting tolerance. In contrast TBG 53 demonstrated improvement for bolting and *fusarium* tolerance compared to its parent TBG 32 and had 80% marketability. Under these low infectious rates for *fusarium* TBG 35, ADS-8, and ADS-23 are still significantly impacted indicating extreme susceptibility.

Based on the entirety of the results between Tables 8 to 10 TBG 54 and the other Florida varieties (ADS-8, TBG 23, 31, 32, 32 and 53) would not be dependable varieties for production in Michigan and California or any other state that has *Fusarium oxysporum* race 2 endemic.

Table 10A and 10B show the result of a trial transplanted in Oxnard, California Mar. 21, 2020, and evaluated Jun. 28, 2020, (99 days) in a normal production field with moderate pressure due to *Fusarium oxysporum* race 2 as, and slight bolting pressure. Tall Utah 52-70 'R' Strain, considered the susceptible check for both traits, was significantly impacted by *fusarium* while slightly impacted by bolting. The plant population (58,080 plants to the acre) was higher than the commercial norm of approximately 45,000 to 47,000 plants to the acre. NA=Not Available.

TABLE 10A

| | | TBG 54 | TBG 31 | TBG 35 | ADS-8 | TBG 32 | TBG 53 | ADS-23 |
|---|---|---|---|---|---|---|---|---|
| Plant Height (cm) | Average | 64.0 | 69.4 | 49.7 | 52.8 | 69.9 | 75.8 | 51.4 |
| | Range | (59-70) | (32-83) | (28-92) | (36-77) | (63-79) | (72-79) | (32-70) |
| Whole Plant weight (kg) | Average | 0.93 | 1.28 | 0.45 | 0.34 | 1.03 | 1.34 | 0.43 |
| | Range | (0.7-1.26) | (0.14-1.94) | (0.12-1.08) | (0.1-0.96) | (0.48-1.94) | (1-1.68) | (0.1-0.86) |
| Trimmed Plant Weight (kg @ 35.6 cm) | Average | 0.28 | 0.50 | NA | NA | 0.17 | 0.85 | NA |
| | Range | (0-1.06) | (0-1.44) | | | (0-1) | (0-1.32) | |
| Number of Outer Petioles (>35.6 cm) | Average | 2.7 | 4.7 | NA | NA | 2.5 | 10.2 | NA |
| | Range | (0-10) | (0-13) | | | (0-14) | (0-15) | |
| Number of Inner Petioles (<35.6 cm) | Average | 1.3 | 2.2 | NA | | 0.9 | 4.1 | NA |
| | Range | (0-5) | (0-6) | | NA | (0-6) | (0-7) | |
| Length of Outer Petioles @ joint (cm) | Average | 29.2 | 27.9 | 15.3 | 13.9 | 29.3 | 32.1 | 16.4 |
| | Range | (22-66) | (11.7-36) | (9.3-22.3) | (10.7-20) | (16.7-35.7) | (28.7-36.7) | (10.3-25.3) |
| Width of Outer Petioles @ midrib (mm) | Average | 7.1 | 10.0 | NA | NA | 3.9 | 18.0 | NA |
| | Range | (0-25) | (0-26.3) | | | (0-19.3) | (0-24) | |
| Thickness of Outer Petioles @ midrib (mm) | Average | 3.5 | 5.0 | NA | NA | 2.1 | 9.0 | NA |
| | Range | (0-12.7) | (0-13) | | | (0-11.3) | 0-12.7 | |
| Length of Seed Stems (cm) | Average | 0.0 | 18.4 | 12.7 | 29.3 | 20.2 | 0.0 | 2.3 |
| | Range | (0-0) | (0-83) | (0-92) | (0-77) | (0-64) | (0-0) | (0-23) |
| | Median | 0.0 | 0.0 | 2.0 | 15.5 | 12.5 | 0.0 | 0.0 |
| Petiole Color (Munsell Color) | | 5gy 7/4- 5gy 6/6 | 5gy 7/4- 5gy 6/6 | NA | NA | NA | 5gy 7/4- 5gy 6/6 | NA |
| Leaf Color (Munsell Color) | | 5gy 3/4 | 5gy 3/4 | NA | NA | NA | 5gy 3/4 | NA |
| Petiole Smoothness | | Smooth/ Slight Rib | Slight Rib/Rib | NA | NA | Smooth | Slight Rib/Rib | NA |
| Petiole Cup | | Cup | Cup | NA | NA | Slight Cup | Slight Cup/Cup | NA |
| % Marketable | | 30% | 20% | 0% | 0% | 10% | 80% | 0% |
| Disease Ratings | | | | | | | | |
| Overall Fusarium Ratings [1 to 5 (1 = susceptible, 5 = tolerant)] | Average | 3.5 | 4 | 1 | 1 | 3.5 | 4 | 1 |
| | Range | 3-4 | 1-5 | 1-2 | 0-2 | 3-4 | 4-5 | 1-2 |
| Root Fusarium Ratings [1 to 5 (1 = susceptible, 5 = tolerant)] | Average | 2 | 2.5 | 1 | 1 | 2 | 3 | 1 |
| | Range | 1-3 | 1-3 | 1-2 | 0-1 | 1-3 | 3 | 1 |
| Defects: | | | | | | | | |
| % Node Crack | | 0% | 0% | 0% | 0% | 0% | 0% | 0% |
| % Brown Stem | | 0% | 30% | 40% | 80% | 0% | 0% | 90% |
| % Butt Crack | | 30% | 60% | 100% | 100% | 50% | 0% | 100% |
| % Top Pith | | 70% | 60% | 100% | 100% | 90% | 0% | 100% |
| % Butt Pith | | 100% | 70% | 100% | 100% | 90% | 100% | 100% |
| % Suckers | | 0% | 30% | 100% | 100% | 60% | 0% | 100% |
| % Feather Leaf | | 70% | 50% | 0% | 0% | 40% | 30% | 70% |
| % Twist | | 0% | 60% | 100% | 100% | 60% | 0% | 100% |

| | | TBG 37 | TBG 43 | TBG 45 | TBG 29 | ADS-1 | TBG 34 |
|---|---|---|---|---|---|---|---|
| Plant Height (cm) | Average | 78.8 | 88.6 | 82.7 | 82.9 | 76.9 | 76.5 |
| | Range | (76-82) | (82-94) | (81-85) | (80-89) | (70-81) | (72-82) |
| Whole Plant weight (kg) | Average | 1.25 | 1.49 | 1.66 | 1.51 | 1.23 | 1.18 |
| | Range | (1.02-1.5) | (1.24-1.76) | (1.3-2.12) | (1.12-2.14) | (0.68-1.72) | (1-1.34) |
| Trimmed Plant Weight (kg @ 35.6 cm) | Average | 0.94 | 1.09 | 1.3 | 1.17 | 0.60 | 0.87 |
| | Range | (0.74-1.06) | (0.9-1.3) | (1.02-1.7) | (0.9-1.56) | (0-1.32) | (0-1.12) |
| Number of Outer Petioles (>35.6 cm) | Average | 11.6 | 10.4 | 12.0 | 11.0 | 6.2 | 7.4 |
| | Range | (10-13) | (8-13) | (9-14) | (10-12) | (0-13) | (0-10) |
| Number of Inner Petioles (<35.6 cm) | Average | 5.1 | 4.8 | 5.2 | 5.3 | 3.1 | 4.2 |
| | Range | (4-6) | (4-6) | (3-6) | (4-6) | (0-6) | (0-5) |
| Length of Outer Petioles @ joint (cm) | Average | 28.4 | 28.1 | 32.3 | 28.6 | 24.5 | 28.6 |
| | Range | (26.3-33) | (26.7-29) | (28-36) | (27-31) | (22-27.3) | (27-30) |
| Width of Outer Petioles @ midrib (mm) | Average | 22.4 | 26.1 | 24.9 | 25.4 | 14.6 | 22.9 |
| | Range | (21-23.7) | (25-28.3) | (22.3-28.3) | (24-28.7) | (0-26) | (0-27) |
| Thickness of Outer Petioles @ midrib (mm) | Average | 10.5 | 12.7 | 12.2 | 12.7 | 6.9 | 10.6 |
| | Range | (7-12.3) | (11.3-13.7) | (11.3-12.7) | (11.7-14) | (0-12.7) | (0-13) |
| Length of Seed Stems (cm) | Average | 0.0 | 0.0 | 0.0 | 0.0 | 0.0 | 0.0 |
| | Range | (0-0) | (0-0) | (0-0) | (0-0) | (0-0) | (0-0) |
| | Median | 0.0 | 0.0 | 0.0 | 0.0 | 0.0 | 0.0 |
| Petiole Color | | 5gy 6/4 | 5gy 6/8, | 5gy 6/6 | 5gy 6/6 | 5gy 6/6 | 5gy 6/6 |

TABLE 10A-continued

| | | | | | | | |
|---|---|---|---|---|---|---|---|
| (Munsell Color) | | | 5gy 3/4 | | | | |
| Leaf Color (Munsell Color) | | 5gy 3/4 | 5gy 3/4 | 5gy 3/4 | 5gy 3/4 | 5gy 3/4 | 5gy 3/4 |
| Petiole Smoothness | | Smooth | Smooth | Slight Rib | Smooth/ Slight Rib | Smooth | Slight Rib/Rib |
| Petiole Cup | | Cup | Cup | Cup | Cup | Cup | Cup |
| % Marketable | | 100% | 100% | 100% | 100% | 60% | 100% |
| Disease Ratings | | | | | | | |
| Overall Fusarium Ratings | Average | 5 | 5 | 5 | 5 | 3.5 | 5 |
| [1 to 5 (1 = susceptible, 5 = tolerant)] | Range | 5 | 5 | 5 | 5 | 3-5 | 5 |
| Root Fusarium Ratings | Average | 4 | 5 | 5 | 4 | 3 | 3.5 |
| [1 to 5 (1 = susceptible, 5 = tolerant)] | Range | 4 | 4-5 | 4-5 | 4-5 | 1-4 | 2-4 |
| Defects: | | | | | | | |
| % Node Crack | | 0% | 0% | 0% | 0% | 0% | 0% |
| % Brown Stem | | 0% | 0% | 0% | 0% | 0% | 0% |
| % Butt Crack | | 0% | 0% | 0% | 0% | 10% | 0% |
| % Top Pith | | 0% | 0% | 0% | 0% | 10% | 10% |
| % Butt Pith | | 20% | 70% | 0% | 0% | 80% | 100% |
| % Suckers | | 0% | 0% | 20% | 0% | 0% | 0% |
| % Feather Leaf | | 0% | 0% | 0% | 0% | 0% | 0% |
| % Twist | | 0% | 20% | 0% | 0% | 0% | 40% |

TABLE 10B

| | | TBG 28 | TBG 33 | Hill's Special | ADS-20 | ADS-22 | Challenger |
|---|---|---|---|---|---|---|---|
| Plant Height (cm) | Average | 96.0 | 78.2 | 65.5 | 67.6 | 84.6 | 74.2 |
| | Range | (92-100) | (68-85) | (56-70) | (61-73) | (81-89) | (37-90) |
| Whole Plant weight (kg) | Average | 1.27 | 1.18 | 1.02 | 1.00 | 1.35 | 1.07 |
| | Range | (1.1-1.5) | (0.84-1.44) | (0.66-1.36) | (0.6-1.28) | (0.98-1.52) | (0.08-1.52) |
| Trimmed Plant Weight (kg @ 35.6 cm) | Average | 1.01 | 0.53 | 0.79 | 0.67 | 1.08 | 0.50 |
| | Range | (0-1.5) | (0-1.16) | (0-1.8) | (0-1.1) | (0.8-1.18) | (0-1.22) |
| Number of Outer Petioles (>35.6 cm) | Average | 10.6 | 5 | 7.8 | 6.5 | 10.9 | 4.8 |
| | Range | (0-16) | (0-12) | (0-12) | (0-11) | (9-13) | (0-11) |
| Number of Inner Petioles (<35.6 cm) | Average | 5.4 | 2.5 | 4 | 3.5 | 5.5 | 2.8 |
| | Range | (0-8) | (0-6) | (0-6) | (0-6) | (4-7) | (0-7) |
| Length of Outer Petioles @ joint (cm) | Average | 33.3 | 28.0 | 25.4 | 26.2 | 24.4 | 29.0 |
| | Range | (30-37) | (23-33) | (22.3-27.7) | (21.3-30.3) | (22.7-25.7) | (16-34.7) |
| Width of Outer Petioles @ midrib (mm) | Average | 20.9 | 13.2 | 19.3 | 17.2 | 25.2 | 11.2 |
| | Range | (0-27) | (0-27.7) | (0-28.3) | (0-26) | (23-27.3) | (0-26) |
| Thickness of Outer Petioles @ midrib (mm) | Average | 9.9 | 6.3 | 8.7 | 8.1 | 12.0 | 5.6 |
| | Range | (0-13.3) | (0-13.3) | (0-11.3) | (0-12.7) | (10.7-13) | (0-12.7) |
| Length of Seed Stems (cm) | Average | 0.0 | 0.0 | 0.0 | 0.0 | 0.0 | 0.0 |
| | Range | (0-0) | (0-0) | (0-0) | (0-0) | (0-0) | (0-0) |
| | Median | 0.0 | 0.0 | 0.0 | 0.0 | 0.0 | 0.0 |
| Petiole Color (Munsell Color) | | 5gy 6/6 | 5gy 6/6 | 5gy 7/4, 5gy 6/4 | 5gy 7/4, 5gy 6/4 | 5gy 6/6 | 5gy 6/6 |
| Leaf Color (Munsell Color) | | 5gy 3/4 | 5gy 3/4 | 5gy 3/4 | 5gy 3/4 | 5gy 3/4 | 5gy 3/4 |
| Petiole Smoothness | | Smooth | Smooth/ Slight Rib | Smooth | Smooth | Smooth | Smooth/ Slight Rib |
| Petiole Cup | | Cup | Cup | Cup | Cup | Cup | Cup |
| % Marketable | | 80% | 50% | 80% | 70% | 100% | 40% |
| Disease Ratings | | | | | | | |
| Overall Fusarium Ratings | Average | 5 | 4 | 3.5 | 4 | 5 | 4.5 |
| [1 to 5 (1 = susceptible, 5 = tolerant)] | Range | 5 | 3-5 | 3-4 | 3-4 | 5 | 1-5 |
| Root Fusarium Ratings | Average | 3.5 | 2.5 | 2.5 | 2.5 | 4 | 3 |
| [1 to 5 (1 = susceptible, 5 = tolerant)] | Range | 2-5 | 1-4 | 2-3 | 1-3 | 3-4 | 1-4 |
| Defects: | | | | | | | |
| % Node Crack | | 0% | 30% | 100% | 100% | 10% | 0% |
| % Brown Stem | | 0% | 0% | 0% | 0% | 0% | 40% |
| % Butt Crack | | 10% | 30% | 20% | 30% | 10% | 50% |
| % Top Pith | | 0% | 50% | 0% | 30% | 0% | 50% |
| % Butt Pith | | 0% | 50% | 50% | 50% | 50% | 0% |
| % Suckers | | 0% | 20% | 100% | 80% | 0% | 10% |
| % Feather Leaf | | 0% | 40% | 0% | 0% | 0% | 30% |
| % Twist | | 10% | 30% | 100% | 100% | 40% | 100% |

TABLE 10B-continued

| | | Sonora | Conquistador | Command | Mission | Tall Utah 52-70 'R' Strain | Tall Utah 52-75 |
|---|---|---|---|---|---|---|---|
| Plant Height (cm) | Average | 67.1 | 64.3 | 71.8 | 70.7 | 54.8 | 65.8 |
| | Range | (62-72) | (23-74) | (63-77) | (65-75) | (46-62) | (57-72) |
| Whole Plant | Average | 1.03 | 0.80 | 1.20 | 0.98 | 0.68 | 0.82 |
| weight (kg) | Range | (0.46-1.44) | (0.06-1.3) | (0.92-1.42) | (0.68-1.26) | (0.2-1.48) | (0-1.24) |
| Trimmed Plant Weight | Average | 0.45 | 0.60 | 1.04 | 0.26 | NA | 0.44 |
| (kg @ 35.6 cm) | Range | (0-1.22) | (0-1.56) | (0.8-1.28) | (0-1.06) | | (0-1.04) |
| Number of Outer | Average | 4.9 | 5.1 | 10.0 | 2.8 | NA | 4.4 |
| Petioles (>35.6 cm) | Range | (0-14) | (0-13) | (9-11) | (0-10) | | (0-10) |
| Number of Inner | Average | 4.4 | 3.2 | 6.7 | 1.7 | NA | 2.7 |
| Petioles (<35.6 cm) | Range | (0-14) | (0-8) | (6-8) | (0-7) | | (0-6) |
| Length of Outer | Average | 25.1 | 23.9 | 25.7 | 27.8 | 20.5 | 25.0 |
| Petioles @ joint (cm) | Range | (18.3-27) | (8-29) | (21.3-29.7) | (26-30.7) | (16-24) | (19.3-29.3) |
| Width of Outer | Average | 8.4 | 11.3 | 24.7 | 6.8 | NA | 11.2 |
| Petioles @ midrib (mm) | Range | (0-22.3) | (0-23.7) | (22-27.7) | (0-21) | | (0-24) |
| Thickness of Outer | Average | 3.9 | 5.3 | 11.8 | 2.8 | NA | 5.4 |
| Petioles @ midrib (mm) | Range | (0-10.3) | (0-11.3) | (10-14.7) | (0-10) | | (0-12) |
| Length of Seed Stems (cm) | Average | 0.0 | 0.0 | 0.0 | 0.0 | 6.4 | 0.0 |
| | Range | (0-0) | (0-0) | (0-0) | (0-0) | (0-30) | (0-0) |
| | Median | 0.0 | 0.0 | 0.0 | 0.0 | 1.5 | 0.0 |
| Petiole Color (Munsell Color) | | 5gy 6/6 | 5gy 6/6 | 5gy 6/6 | 5gy 6/6 | NA | 5gy 6/6 |
| Leaf Color (Munsell Color) | | 5gy 4/4 | 5gy 4/4 | 5gy 4/4 | 5gy 4/4 | NA | 5gy 4/4 |
| Petiole Smoothness | | Slight Rib | Smooth | Slight Rib | Slight Rib | NA | Smooth |
| Petiole Cup | | Cup | Cup | Cup | Cup | NA | Cup |
| % Marketable | | 40% | 50% | 100% | 30% | 0% | 50% |
| Disease Ratings | | | | | | | |
| Overall Fusarium Ratings | Average | 3.5 | 3.5 | 5 | 3.5 | 1.5 | 3 |
| [1 to 5 (1 = susceptible, 5 = tolerant)] | Range | 2-5 | 1-5 | 5 | 2-5 | 0-3 | 1-5 |
| Root Fusarium Ratings | Average | 2.5 | 2.5 | 2.5 | 1.5 | 1.5 | 2 |
| [1 to 5 (1 = susceptible, 5 = tolerant)] | Range | 1-4 | 1-4 | 1-4 | 1-4 | 0-3 | 1-3 |
| Defects: | | | | | | | |
| % Node Crack | | 10% | 0% | 50% | 0% | 0% | 0% |
| % Brown Stem | | 30% | 0% | 0% | 40% | 60% | 0% |
| % Butt Crack | | 40% | 30% | 0% | 30% | 100% | 40% |
| % Top Pith | | 60% | 50% | 40% | 70% | 100% | 70% |
| % Butt Pith | | 90% | 90% | 50% | 90% | 100% | 90% |
| % Suckers | | 0% | 30% | 0% | 0% | 100% | 0% |
| % Feather Leaf | | 60% | 70% | 20% | 40% | 100% | 50% |
| % Twist | | 60% | 50% | 20% | 50% | 100% | 50% |

As shown in Tables 10A and 10B, TBG 43 and TBG 45 were the most tolerant to *Fusarium oxysporum* race 2 based on both the overall and root infection ratings in addition to the % marketability followed closely by TBG 29 and TBG 37 and slightly more distantly TBG 28. Of these TBG 28 had was the tallest for plant height followed by TBG 45 and the others were fairly similar. TBG 45 and TBG 28 were very similar with longer petiole length compared to TBG 43, TBG 29 and TBG 37. Except for Tall Utah 52-70 'R' Strain bolting pressure as measured by seed stem length was not notable in what most would consider the California coastal varieties. However, it was a significant issue in several varieties developed for Florida production (ADS-8, ADS-23, TBG 31, TBG 32). However, it was not severe in three Florida varieties ADS-23, TBG 54, and TBG 53 as measured by seed stem length. TBG 54 was considerably improved compared to sister TBG 31 and TBG 53 compared to parent TBG 32. TBG 54 was fairly similar to sister TBG 31 for *fusarium* impact as were TBG 53 and parent TBG 32 (*fusarium* ratings).

Table 11 represents the results of a trial in Oxnard, California that was specially developed with especially high levels of *Fusarium oxysporum* race 2 inoculums in order to develop and evaluate cultivars for tolerance. This field is also infused with a low level of *Fusarium oxysporum* race 4 representing the disease transition that is occurring in many of the production areas in California. Since TBG 54 is susceptible to race 2, it is not surprising that a trial that had high levels of race 2 and low levels of race-4, Table 10, would further demonstrate TBG 54's susceptibility as indicated by *fusarium* ratings and survival data.

Tables 11A and 11B show the result of a trial transplanted in Oxnard, California Aug. 9, 2020, and evaluated Dec. 12, 2020, (125 days) in a block that has been developed with especially high levels of *Fusarium oxysporum* race 2 and slight to moderate levels from *Fusarium oxysporum* race 4. The plant population (58,080 plants to the acre) was higher than the commercial norm of approximately 45,000 to 47,000 plants to the acre.

TABLE 11A

|  |  | TBG 54 | TBG 31 | TBG 35 | ADS-23 | TBG 32 | TBG 53 | TBG 37 |
|---|---|---|---|---|---|---|---|---|
| Plant Height (cm) | Average | 5.0 | 1.5 | 0.6 | 0.0 | 3.4 | 3.0 | 37.3 |
|  | Range | (0-22) | (0-13) | (0-12) | (0-0) | (0-23) | (0-20) | (0-58) |
| Whole Plant weight (kg) | Average | NA | NA | NA | NA | NA | NA | NA |
|  | Range |  |  |  |  |  |  |  |
| Trimmed Plant Weight (kg @ 35.6 cm) | Average | NA | NA | NA | NA | NA | NA | NA |
|  | Range |  |  |  |  |  |  |  |
| Number of Outer Petioles (>35.6 cm) | Average | NA | NA | NA | NA | NA | NA | NA |
|  | Range |  |  |  |  |  |  |  |
| Number of Inner Petioles (<35.6 cm) | Average | NA | NA | NA | NA | NA | NA | NA |
|  | Range |  |  |  |  |  |  |  |
| Length of Outer Petioles to the joint (cm) | Average | 2.8 | 0.6 | 0.3 | 0.0 | 1.2 | 1.3 | 15.9 |
|  | Range | (0-8) | (0-8) | (0-6) | (0-0) | (0-9) | (0-8) | (0-25) |
| Width of Outer Petioles at the midrib (mm) | Average | NA | NA | NA | NA | NA | NA | NA |
|  | Range |  |  |  |  |  |  |  |
| Thickness of Outer Petioles at the midrib (mm) | Average | NA | NA | NA | NA | NA | NA | NA |
|  | Range |  |  |  |  |  |  |  |
| Petiole Smoothness |  | NA | NA | NA | NA | NA | NA | NA |
| Petiole Cup |  | NA | NA | NA | NA | NA | NA | NA |
| % Marketable |  | NA | NA | NA | NA | NA | NA | NA |
| Disease: |  |  |  |  |  |  |  |  |
| Survival Rate (%) | Healthy | 0% | 0% | 0% | 0% | 0% | 0% | 0% |
|  | Dying | 37% | 12% | 5% | 0% | 22% | 22% | 80% |
|  | Dead | 63% | 88% | 95% | 100% | 78% | 78% | 20% |
| Overall Fusarium Ratings [0 to 5 (0 = dead, 5 = tolerant)] | Average | 0.4 | 0.2 | 0.1 | 0.0 | 0.4 | 0.5 | 3.2 |
|  | Range | (0-1) | (0-1) | (0-1) | (0-0) | (0-2) | (0-1) | (0-5) |
| Root Fusarium Ratings [0 to 5 (0 = dead, 5 = tolerant)] | Average | 0.4 | 0.2 | 0.1 | 0.0 | 0.3 | 0.5 | 0.8 |
|  | Range | (0-1) | (0-1) | (0-1) | (0-0) | (0-1) | (0-1) | (0-1) |

|  |  | TBG 43 | TBG 45 | TBG 29 | ADS-1 | TBG 34 |
|---|---|---|---|---|---|---|
| Plant Height (cm) | Average | 84.6 | 83.1 | 60.4 | 9.9 | 21.2 |
|  | Range | (78-93) | (80-89) | (0-81) | (0-27) | (0-32) |
| Whole Plant weight (kg) | Average | 1.04 | 1.24 | 0.74 | NA | NA |
|  | Range | (0.53-1.33) | (0.94-1.53) | (0-1.41) |  |  |
| Trimmed Plant Weight (kg @ 35.6 cm) | Average | 0.75 | 0.91 | 0.58 | NA | NA |
|  | Range | (0.37-1) | (0.71-1.11) | (0-1.09) |  |  |
| Number of Outer Petioles (>35.6 cm) | Average | 11.1 | 12.6 | 7.2 | NA | NA |
|  | Range | (9-14) | (11-14) | (0-11) |  |  |
| Number of Inner Petioles (<35.6 cm) | Average | 4.4 | 4.3 | 3.3 | NA | NA |
|  | Range | (3-5) | (3-6) | (0-5) |  |  |
| Length of Outer Petioles to the joint (cm) | Average | 26.6 | 32.1 | 20.0 | 3.8 | 8.1 |
|  | Range | (21.3-29) | (26.7-38) | (0-27) | (0-12) | (0-14) |
| Width of Outer Petioles at the midrib (mm) | Average | 21.7 | 23.0 | 16.3 | NA | NA |
|  | Range | (17.3-24.7) | (22-24.7) | (0-26) |  |  |
| Thickness of Outer Petioles at the midrib (mm) | Average | 11.9 | 11.0 | 9.1 | NA | NA |
|  | Range | (9.7-13.3) | (10-12.7) | (0-13.7) |  |  |
| Petiole Smoothness |  | Smooth | Smooth/ Slight Rib | Smooth/ Slight Rib | NA | NA |
| Petiole Cup |  | Cup | Slight Cup/Cup | Cup | NA | NA |
| % Marketable |  | 80% | 100% | 30% | NA | NA |
| Disease: |  |  |  |  |  |  |
| Survival Rate (%) | Healthy | 80% | 100% | 30% | 0% | 0% |
|  | Dying | 20% | 0% | 50% | 47% | 80% |
|  | Dead | 0% | 0% | 20% | 53% | 20% |
| Overall Fusarium Ratings [0 to 5 (0 = dead, 5 = tolerant)] | Average | 4.8 | 5 | 3 | 0.9 | 1.9 |
|  | Range | (3-5) | (5-5) | (0-4) | (0-3) | (0-3) |
| Root Fusarium Ratings [0 to 5 (0 = dead, 5 = tolerant)] | Average | 3.6 | 5 | 3 | 0.7 | 1.1 |
|  | Range | (1-5) | (4-5) | (0-4) | (0-2) | (0-2) |

TABLE 11B

Hill's

TABLE 11B-continued

| | | TBG 28 | TBG 33 | ADS-22 | Special | ADS-20 | Challenger | Sonora |
|---|---|---|---|---|---|---|---|---|
| Plant Height (cm) | Average | 6.4 | 4.1 | 16.5 | 7.7 | 10.5 | 24.4 | 12.6 |
| | Range | (0-36) | (0-27) | (0-63) | (0-35) | (0-33) | (0-56) | (0-33) |
| Whole Plant weight (kg) | Average Range | NA | NA | NA | NA | NA | NA | NA |
| Trimmed Plant Weight (kg @ 35.6 cm) | Average Range | NA | NA | NA | NA | NA | NA | NA |
| Number of Outer Petioles (>35.6 cm) | Average Range | NA | NA | NA | NA | NA | NA | NA |
| Number of Inner Petioles (<35.6 cm) | Average Range | NA | NA | NA | NA | NA | NA | NA |
| Length of Outer Petioles to the joint (cm) | Average | 2.2 | 1.3 | 5.3 | 2.6 | 4.1 | 8.4 | 4.8 |
| | Range | (0-12) | (0-8) | (0-22) | (0-12) | (0-14) | (0-21) | (0-14) |
| Width of Outer Petioles at the midrib (mm) | Average Range | NA | NA | NA | NA | NA | NA | NA |
| Thickness of Outer Petioles at the midrib (mm) | Average Range | NA | NA | NA | NA | NA | NA | NA |
| Petiole Smoothness | | NA | NA | NA | NA | NA | NA | NA |
| Petiole Cup | | NA | NA | NA | NA | NA | NA | NA |
| % Marketable | | NA | NA | NA | NA | NA | NA | NA |
| Disease: | | | | | | | | |
| Survival Rate (%) | Healthy | 0% | 0% | 0% | 0% | 0% | 10% | 0% |
| | Dying | 35% | 27% | 30% | 32% | 50% | 50% | 48% |
| | Dead | 65% | 73% | 70% | 68% | 50% | 40% | 52% |
| Overall Fusarium Ratings [0 to 5 (0 = dead, 5 = tolerant)] | Average | 0.6 | 0.5 | 1.1 | 0.7 | 1.2 | 1.8 | 0.8 |
| | Range | (0-2) | (0-3) | (0-4) | (0-2) | (0-3) | (0-3) | (0-2) |
| Root Fusarium Ratings [0 to 5 (0 = dead, 5 = tolerant)] | Average | 0.4 | 0.3 | 0.4 | 0.5 | 0.7 | 1.2 | 0.6 |
| | Range | (0-1) | (0-1) | (0-2) | (0-1) | (0-2) | (0-2) | (0-1) |

| | | Conquistador | Command | Mission | Tall Utah 52-70 'R' Strain | Tall Utah 52-75 |
|---|---|---|---|---|---|---|
| Plant Height (cm) | Average | 15.4 | 12.8 | 14.0 | 1.7 | 1.7 |
| | Range | (0-37) | (0-38) | (0-30) | (0-19) | (0-22) |
| Whole Plant weight (kg) | Average Range | NA | NA | NA | NA | NA |
| Trimmed Plant Weight (kg @ 35.6 cm) | Average Range | NA | NA | NA | NA | NA |
| Number of Outer Petioles (>35.6 cm) | Average Range | NA | NA | NA | NA | NA |
| Number of Inner Petioles (<35.6 cm) | Average Range | NA | NA | NA | NA | NA |
| Length of Outer Petioles to the joint (cm) | Average | 4.1 | 3.7 | 4.6 | 0.8 | 0.7 |
| | Range | (0-14) | (0-12) | (0-10) | (0-10) | (0-8) |
| Width of Outer Petioles at the midrib (mm) | Average Range | NA | NA | NA | NA | NA |
| Thickness of Outer Petioles at the midrib (mm) | Average Range | NA | NA | NA | NA | NA |
| Petiole Smoothness | | NA | NA | NA | NA | NA |
| Petiole Cup | | NA | NA | NA | NA | NA |
| % Marketable | | NA | NA | NA | NA | NA |
| Disease: | | | | | | |
| Survival Rate (%) | Healthy | 0% | 0% | 0% | 0% | 0% |
| | Dying | 58% | 45% | 60% | 12% | 12% |
| | Dead | 42% | 55% | 40% | 88% | 88% |
| Overall Fusarium Ratings [0 to 5 (0 = dead, 5 = tolerant)] | Average | 1 | 0.9 | 1.1 | 0.3 | 0.3 |
| | Range | (0-2) | (0-2) | (0-2) | (0-1) | (0-2) |
| Root Fusarium Ratings [0 to 5 (0 = dead, 5 = tolerant)] | Average | 0.7 | 0.5 | 0.7 | 0.3 | 0.3 |
| | Range | (0-2) | (0-1) | (0-1) | (0-1) | (0-1) |

As shown in Tables 11A and 111B, under these conditions TBG 45 demonstrated excellent tolerance to both *Fusarium oxysporum* race-2 and race 4 as can be noted by *fusarium* ratings, marketability and survivable rates. TBG 43 did not perform as well as TBG 45 and TBG 29 performed even worse but they were the next best performing varieties in the trial. All three varieties are noted for tolerance to race-2 so the primary marketable differences between them in this trial is their tolerance level to race 4. All other varieties, including the Florida varieties (TBG 31, TBG 32, TBG 35, TBG 53, TBG 54, and ADS-23) showed little to no tolerance to the combined diseases and were not marketable and mostly dead or dying.

Tables 12-13 show the results of trials grown in a field in Oxnard, California, that was created with especially high inoculum levels of *Fusarium oxysporum* race 4 in order to develop and evaluate cultivars for tolerance. This field has had two celery crops produced on it in every year since the disease was first documented in 2013. In fact, this is the actual field where the disease was first observed. With no rotation or attempt to diminish inoculum levels this field has gained inoculum levels and infectious potential over the years and is currently one of the most heavily infested fields in existence.

Under these production conditions with *fusarium* race-4 inoculums, TBG 54 and other Florida varieties (ADS-2, ADS-8, TBG 23, TBG 31, TBG 32, TBG 35, TBG 43, and Floribelle) all are unable to generate marketable stalks (Tables 12 and 13) and have very low survival rates and heavy infection rates (Table 13).

Table 12 shows the result of a trial transplanted in Oxnard, California, Aug. 14, 2019, and evaluated Dec. 23, 2019 (131 days). This trial was grown in a production block that has been developed with especially high levels of *Fusarium oxysporum* race 4 levels in order to evaluate and develop varieties for increased tolerance to the disease. Not only is this field especially high in the disease it is the location where the disease was first identified. The plant population (58,080 plants to the acre) was higher than the commercial norm of approximately 45,000 to 47,000 plants to the acre.

had more survivors than ADS-8 but none were marketable. All other varieties, including the Florida varieties (TBG 31, TBG 32, TBG 35, TBG 53, TBG 54, ADS-23, and Floribelle) showed low survival and no marketable plants. However, percentage survival were better for TBG 54 compared to sister TBG 31, TBG 35 compared to parent ADS-8 and TBG 53 compared to parent TBG 32.

Table 13A and 13B show the result of a trial transplanted in Oxnard, California, Aug. 19, 2020, and evaluated Dec. 2, 2020 (105 days). This trial was grown in a production block that has been developed with especially high levels of *Fusarium oxysporum* race 4 levels in order to evaluate and develop varieties for increased tolerance to the disease. Not only is this field especially high in the disease it is the location where the disease was first identified. The plant population (58,080 plants to the acre) was higher than the commercial norm of approximately 45,000 to 47,000 plants to the acre. NA=Not Available

TABLE 12

| | | TBG 54 | TBG 31 | TBG 35 | ADS-8 | TBG 32 | TBG 53 | Floribelle | ADS-23 | ADS-2 | TBG 37 |
|---|---|---|---|---|---|---|---|---|---|---|---|
| Plant Height (cm) | Average | NA | NA | NA | NA | NA | NA | NA | NA | NA | NA |
| | Range | | | | | | | | | | |
| Whole Plant weight (kg) | Average | NA | NA | NA | NA | NA | NA | NA | NA | NA | NA |
| | Range | | | | | | | | | | |
| Trimmed Plant Weight (kg) | Average | NA | NA | NA | NA | NA | NA | NA | NA | NA | NA |
| | Range | | | | | | | | | | |
| Length of Outer Petioles to the joint (cm) | Average | NA | NA | NA | NA | NA | NA | NA | NA | NA | NA |
| | Range | | | | | | | | | | |
| % Survival | | 23% | 4% | 33% | 12% | 39% | 52% | 21% | 15% | 42% | 8% |
| % Marketable | | 0% | 0% | 0% | 0% | 0% | 0% | 0% | 0% | 0% | 0% |

| | | TBG 43 | TBG 45 | TBG 29 | ADS-1 | TBG 34 | TBG 28 | TBG 33 | ADS-22 | ADS-20 |
|---|---|---|---|---|---|---|---|---|---|---|
| Plant Height (cm) | Average | 32.70 | 80.10 | NA | NA | NA | NA | NA | NA | NA |
| | Range | (0-74) | (0-85) | | | | | | | |
| Whole Plant weight (kg) | Average | 0.65 | 1.35 | NA | NA | NA | NA | NA | NA | NA |
| | Range | (0-1.42) | (0-1.5) | | | | | | | |
| Trimmed Plant Weight (kg) | Average | 0.31 | 1.15 | NA | NA | NA | NA | NA | NA | NA |
| | Range | (0-1.1) | (0-1.32) | | | | | | | |
| Length of Outer Petioles to the joint (cm) | Average | 12.4 | 28.2 | NA | NA | NA | NA | NA | NA | NA |
| | Range | (0-27) | 0-35 | | | | | | | |
| % Survival | | 37% | 81% | 16% | 24% | 31% | 9% | 18% | 17% | 10% |
| % Marketable | | 35% | 80% | 0% | 0% | 0% | 0% | 0% | 0% | 0% |

As shown in Table 12, under the *fusarium* conditions of this trial most varieties had a few to several plants that were still alive at evaluation but were not able to sustain development of marketable celery stalks. Most were barely alive. However, TBG 43 and TBG 45 were each able to produce marketable celery stalks. TBG 43 was fairly tolerant (35% marketable) and essentially all survivors were marketable. Essentially all survivors of TBG 45 were marketable and at 80% marketable showed good tolerance for race 4. TBG 35

TABLE 13A

|  |  | TBG 54 | TBG 31 | TBG 35 | TBG 32 | TBG 53 | ADS-23 | Floribelle |
|---|---|---|---|---|---|---|---|---|
| Plant Height (cm) | Average | 0.0 | 2.9 | 0.0 | 0.5 | 0.5 | 0.7 | 0.0 |
|  | Range | (0-0) | (0-28) | (0-0) | (0-15) | (0-11) | (0-18) | (0-0) |
| Whole Plant weight (kg) | Average | NA | NA | NA | NA | NA | NA | NA |
|  | Range |  |  |  |  |  |  |  |
| Trimmed Plant Weight (kg @ 35.6 cm) | Average | NA | NA | NA | NA | NA | NA | NA |
|  | Range |  |  |  |  |  |  |  |
| Number of Outer Petioles (>35.6 cm) | Average | NA | NA | NA | NA | NA | NA | NA |
|  | Range |  |  |  |  |  |  |  |
| Number of Inner Petioles (<35.6 cm) | Average | NA | NA | NA | NA | NA | NA | NA |
|  | Range |  |  |  |  |  |  |  |
| Length of Outer Petioles to the joint (cm) | Average | 0.0 | 1.1 | 0.0 | 0.2 | 0.1 | 0.3 | 0.0 |
|  | Range | (0-0) | (0-12) | (0-0) | (0-5) | (0-3) | (0-5) | (0-0) |
| Width of Outer Petioles at the midrib (mm) | Average | NA | NA | NA | NA | NA | NA | NA |
|  | Range |  |  |  |  |  |  |  |
| Thickness of Outer Petioles at the midrib (mm) | Average | NA | NA | NA | NA | NA | NA | NA |
|  | Range |  |  |  |  |  |  |  |
| Petiole Smoothness |  | NA | NA | NA | NA | NA | NA | NA |
| Petiole Cup |  | NA | NA | NA | NA | NA | NA | NA |
| % Marketable |  | 0% | 0% | 0% | 0% | 0% | 0% | 0% |
| Disease: |  |  |  |  |  |  |  |  |
| Survival Rate (%) | Healthy | 0% | 2% | 0% | 0% | 0% | 0% | 0% |
|  | Dying | 0% | 13% | 0% | 5% | 5% | 4% | 0% |
|  | Dead | 100% | 85% | 100% | 95% | 95% | 96% | 100% |
| Overall Fusarium Ratings [0 to 5 (0 = dead, 5 = tolerant)] | Average | 0 | 0 | 0 | 0 | 0 | 0 | 0 |
|  | Range | (0-0) | (0-2) | (0-0) | (0-1) | (0-1) | 0-1 | (0-0) |

|  |  | TBG 37 | TBG 43 | TBG 45 | TBG 29 | ADS-1 | TBG 34 |
|---|---|---|---|---|---|---|---|
| Plant Height (cm) | Average | 0.6 | 40.5 | 70.3 | 8.8 | 5.5 | 1.9 |
|  | Range | (0-9) | (0-70) | (68-74) | (0-49) | (0-25) | (0-18) |
| Whole Plant weight (kg) | Average | NA | 0.37 | 0.87 | 0.06 | NA | NA |
|  | Range |  | (0-0.82) | (0.74-1.01) | (0-0.39) |  |  |
| Trimmed Plant Weight (kg @ 35.6 cm) | Average | NA | 0.30 | 0.69 | 0.05 | NA | NA |
|  | Range |  | (0-0.67) | (0.6-0.81) | (0-0.36) |  |  |
| Number of Outer Petioles (>35.6 cm) | Average | NA | 4.4 | 9.9 | 0.7 | NA | NA |
|  | Range |  | (0-9) | (8-11) | (0-4) |  |  |
| Number of Inner Petioles (<35.6 cm) | Average | NA | 5.5 | 6.7 | 1.2 | NA | NA |
|  | Range |  | (0-10) | (6-8) | (0-6) |  |  |
| Length of Outer Petioles to the joint (cm) | Average | 0.1 | 14.5 | 28.8 | 2.7 | 3.2 | 0.7 |
|  | Range | 90-2) | (0-27) | (26-32) | (0-13.7) | (0-12) | (0-7) |
| Width of Outer Petioles at the midrib (mm) | Average | NA | 10.7 | 22.9 | 3.1 | NA | NA |
|  | Range |  | (0-20) | (20.3-25) | (0-16) |  |  |
| Thickness of Outer Petioles at the midrib (mm) | Average | NA | 5.7 | 10.3 | 1.7 | NA | NA |
|  | Range |  | (0-11.3) | (9.3-11.3) | (0-9) |  |  |
| Petiole Smoothness |  | NA | Smooth/ Slight Rib | Smooth/ Slight Rib | Slight Rib | NA | NA |
| Petiole Cup |  | NA | Cup/Deep Cup | Cup | Cup | NA | NA |
| % Marketable |  | 0% | 50% | 94% | 0% | 0% | 0% |
| Disease: |  |  |  |  |  |  |  |
| Survival Rate (%) | Healthy | 0% | 74% | 95% | 18% | 0% | 0% |
|  | Dying | 7% | 3% | 3% | 10% | 17% | 12% |
|  | Dead | 93% | 23% | 3% | 82% | 83% | 88% |
| Overall Fusarium Ratings [0 to 5 (0 = dead, 5 = tolerant)] | Average | 0 | 2.5 | 4.5 | 1.5 | 0 | 0 |
|  | Range | 0-1 | (0-5) | 4-5 | (0-5) | 0-1 | (0-1) |

TABLE 13B

|  |  | TBG 28 | TBG 33 | ADS-22 | Hill's Special | ADS-20 | Challenger | Sonora |
|---|---|---|---|---|---|---|---|---|
| Plant Height (cm) | Average | 0.0 | 0.0 | 3.7 | 1.2 | 1.5 | NA | NA |
|  | Range | (0-0) | (0--0) | (0-34) | (0-18) | (0-21) |  |  |
| Whole Plant weight (kg) | Average | NA | NA | NA | NA | NA | NA | NA |
|  | Range |  |  |  |  |  |  |  |

TABLE 13B-continued

| | | | | | | | | |
|---|---|---|---|---|---|---|---|---|
| Trimmed Plant Weight (kg @ 35.6 cm) | Average Range | NA | NA | NA | NA | NA | NA | NA |
| Number of Outer Petioles (>35.6 cm) | Average Range | NA | NA | NA | NA | NA | NA | NA |
| Number of Inner Petioles (<35.6 cm) | Average Range | NA | NA | NA | NA | NA | NA | NA |
| Length of Outer Petioles to the joint (cm) | Average Range | 0.0 (0-0) | 0.0 (0-0) | 1.1 (0-11) | 0.6 (0-8) | 0.5 (0-7) | NA | NA |
| Width of Outer Petioles at the midrib (mm) | Average Range | NA | NA | NA | NA | NA | NA | NA |
| Thickness of Outer Petioles at the midrib (mm) | Average Range | NA | NA | NA | NA | NA | NA | NA |
| Petiole Smoothness | | NA | NA | NA | NA | NA | NA | NA |
| Petiole Cup | | NA | NA | NA | NA | NA | NA | NA |
| % Marketable | | 0% | 0% | 0% | 0% | 0% | 0% | 0% |
| Disease: | | | | | | | | |
| Survival Rate (%) | Healthy | 0% | 0% | 2% | 0% | 0% | 0% | 0% |
| | Dying | 0% | 0% | 13% | 13% | 10% | 13% | 11% |
| | Dead | 100% | 100% | 85% | 87% | 90% | 87% | 89% |
| Overall Fusarium Ratings [0 to 5 (0 = dead, 5 = tolerant)] | Average Range | 0 (0-0) | 0 (0-0) | 0 (0-3) | 0 0-1 | 1 (0-1) | 0 0-1 | 0 0-1 |

| | | Conquistador | Command | Mission | Tall Utah 52-70 'R' Strain | Tall Utah 72-75 |
|---|---|---|---|---|---|---|
| Plant Height (cm) | Average Range | NA | NA | NA | NA | NA |
| Whole Plant weight (kg) | Average Range | NA | NA | NA | NA | NA |
| Trimmed Plant Weight (kg @ 35.6 cm) | Average Range | NA | NA | NA | NA | NA |
| Number of Outer Petioles (>35.6 cm) | Average Range | NA | NA | NA | NA | NA |
| Number of Inner Petioles (<35.6 cm) | Average Range | NA | NA | NA | NA | NA |
| Length of Outer Petioles to the joint (cm) | Average Range | NA | NA | NA | NA | NA |
| Width of Outer Petioles at the midrib (mm) | Average Range | NA | NA | NA | NA | NA |
| Thickness of Outer Petioles at the midrib (mm) | Average Range | NA | NA | NA | NA | NA |
| Petiole Smoothness | | NA | NA | NA | NA | NA |
| Petiole Cup | | NA | NA | NA | NA | NA |
| % Marketable | | 0% | 0% | 0% | 0% | 0% |
| Disease: | | | | | | |
| Survival Rate (%) | Healthy | 0% | 0% | 0% | 0% | 0% |
| | Dying | 8% | 15% | 10% | 7% | 1% |
| | Dead | 92% | 85% | 90% | 93% | 99% |
| Overall Fusarium Ratings [0 to 5 (0 = dead, 5 = tolerant)] | Average Range | 0 0-1 | 0 0-1 | 0 0-1 | 0 0-1 | 0 0-1 |

As shown in Tables 13A and 13B, under the *fusarium* conditions of this trial TBG 29 had a few plants that had slightly better vigor but with only 18% survival and an average *fusarium* rating of 1.5 even the strongest of the plants were not marketable. Under the *fusarium* conditions of this trial which has been developed to be stronger than traditionally infected fields TBG 43 tolerance is starting to break down with 74% survival and 50% marketable. TBG 45 which was specifically bred for tolerance to race-4 had 94% marketability and was very tolerant (4-5 rating). No other varieties including the Florida varieties (ADS-23, TBG 31, TBG 32, TBG 35, TBG 53, TBG 54, and Floribelle) showed tolerance to the disease (overall *fusarium* ratings) and were mostly dead or dying (survival rate).

Tables 14-15 post the results for disease trials providing tolerance and susceptibility information for numerous varieties for *Septoria apiicola* (celery late blight) and *Colletotrichum* fiorinaiae. Neither disease is currently a problem in Florida production so the fact that TBG 54 is moderately susceptible to *Colletotrichum* and very susceptible to *Septoria* is not currently a prominent issue for its use in Florida winter production. TBG 54 is very similar to sister TBG 31 for susceptibility to *Septoria* and is more susceptible for *Colletotrichum*. Due to combined susceptibility to *Fusarium* race 2 and *Colletotrichum* TBG 54 is not as preferable for production in Michigan.

Table 14 shows the results from trials that were planted in Oxnard, California, in 2018, 2019, 2020, and 2021 specifically for evaluating, identifying and developing varieties with improved tolerance to *Septoria apiicola* (celery late blight). These trials were inoculated with spore suspension of *septoria* in order to induce infection. Infection ratings were scored with 1 representing susceptible and 5 representing tolerant. The range represents variations between replications and the average is their mean. NA=not available=not in the trial.

TABLE 14

| 2018 RATING | | 2019 RATING | | 2020 RATING | | 2021 RATING | | Overall |
| Range | Average | Range | Average | Range | Average | Range | Average | Average |
|---|---|---|---|---|---|---|---|---|
| 2 | 2 | 3-4 | 3.5 | 1-2 | 1.3 | 2-3 | 2.5 | 2.3 |
| 1-3 | 1.5 | 2-4 | 2.5 | NA | NA | 3 | 3 | 2.3 |
| 1-3 | 2.5 | 2 | 2 | 1 | 1 | 2 | 2 | 1.9 |
| 2 | 2 | 1-2 | 1.6 | 1 | 1 | 1 | 1 | 1.4 |
| NA | NA | NA | NA | NA | NA | 2 | 2 | 2.0 |
| 1 | 1 | 1-2 | 1.5 | 1-2 | 1 | 1 | 1 | 1.1 |
| 1-2 | 1 | 2-3 | 2.5 | 1-3 | 1.5 | 3 | 3 | 2.0 |
| 2 | 2 | NA | NA | NA | NA | NA | NA | 2.0 |
| 1 | 1 | 2 | 2 | 1 | 1 | 1-2 | 1.5 | 1.4 |
| 1-2 | 1.5 | 2-4 | 3.5 | 1 | 1 | 1-3 | 2 | 2.0 |
| 4 | 4 | 4 | 4 | 1 | 1 | 1-2 | 1.5 | 2.6 |
| 1 | 1 | NA | NA | 1 | 1 | 1-3 | 2 | 1.3 |
| 1-2 | 1 | NA | NA | NA | NA | NA | NA | 1.0 |
| 2 | 2 | 3 | 3 | 1 | 1 | 1-3 | 2 | 2.0 |
| NA | NA | 3 | 3 | 1 | 1 | NA | NA | 2.0 |
| 1 | 1 | NA | NA | NA | NA | NA | NA | 1.0 |
| 2 | 2 | NA | NA | 1 | 1 | 3 | 3 | 2.0 |

As shown in Table 14, under these conditions there is some variation between years and in particular 2020 which had heavier infection (based on ratings). Much of this can be attributed to variable infectious conditions between years, timing of rating the infection (later ratings generally result in heavier infection rates) and on occasion for plot variation within a year the presence of more infected plots surrounding particular plots which provided more secondary inoculum. on a rating scale of 1 to 5 with 5 being tolerant TBG 37, TBG 28 were generally slightly below moderately tolerant and ADS-23 was moderately tolerant (considering overall average for four years. TBG 35 has no tolerance. Based on these results TBG 54 was susceptible and fairly similar to sister TBG 31 and TBG 53 moderately susceptible and similar to parent TBG 32 for performance. Tables 15-16 post the results for disease trials providing tolerance and susceptibility information for numerous varieties for *Septoria apiicola* (celery late blight) and *Colletotrichum fiorinaiae*. Neither disease is currently a problem in Florida production so the fact that TBG 54 is moderately susceptible to *Colletotrichum* and very susceptible to *Septoria* is not currently a prominent issue for its use in Florida winter production.

Table 15 shows the results from trials that were planted in Byron Center, Michigan, in 2013, 2018, and 2021, specifically for evaluating, identifying, and developing varieties with improved tolerance to *Colletotrichum fioriniae*. These trials were planted in a field that has a strong history for natural *Colletotrichum* infection. Infection data presented in this table represents the percentage of plants infected with *Colletotrichum*. The average is the average between two years (2013 and 2018 only because in 2021 the only varieties included in the trial from prior years were ADS-1 and TBG 28. The data for 2020 was presented in the table to the right of the average.

84

TABLE 15

| Variety | 2013 | 2018 | Average (2013 & 2018) | 2021 |
|---|---|---|---|---|
| TBG 28 | 14.3% | 9.1% | 11.7% | 14% |
| TBG 33 | NA | 10.7% | 10.7% | NA |
| TBG 32 | 5.4% | 16.7% | 11.1% | NA |
| TBG 31 | NA | 21.5% | 21.5% | NA |

TABLE 15-continued

| Variety | 2013 | 2018 | Average (2013 & 2018) | 2021 |
|---|---|---|---|---|
| TBG 35 | 25.6% | 23.1% | 24.4% | NA |
| TBG 54 | NA | 30.2% | 30.2% | NA |
| ADS-22 | 34.1% | 33.3% | 33.7% | NA |
| ADS-8 | 9.0% | 61.8% | 35.4% | NA |
| ADS-1 | 55.9% | 42.4% | 49.2% | 25% |
| TBG 43 | NA | 50.9% | 50.9% | NA |
| TBG 37 | NA | 52.9% | 52.9% | NA |
| ADS-23 | NA | 56.9% | 56.9% | NA |
| TBG 29 | 28.1% | 59.7% | 43.9% | NA |

As shown in Table 15, under these conditions TBG 28, TBG 33, and TBG 32 demonstrated improved *Colletotrichum* tolerance (% infection each year and average for two years) compared to the other varieties including two varieties that are commercial standards in Michigan (ADS-1 and ADS-22). TBG 54 was not as tolerant as sister TBG 32 and TBG 35 was improved compared to ADS-8 in 2018, but not 2013.

*Cercospora apii* (celery early blight) is however a disease that is more critical in Florida celery production and tolerance is particularly critical in Florida organic celery production and seasonal production in the fall and later spring conventional production when rain is more prominent. As can be seen by the results shown in Table 16 for trials that are designed for evaluation and selection to improve tolerance TBG 54 has moderate tolerance to *Cercospora. While this tolerance is not sufficient to allow TBG 54 production in Florida* for organic production this is considerably improved compared to ADS-8 and relatively similar to its sister TBG 31 which are used in conventional production. The tolerance is sufficient and beneficial for fall production during the wetter hurricane season for early winter harvest as well as the traditionally spring harvest season when rains once again become more prolific in Florida.

Table 16 shows the results from trials that were planted in Belle Glade, Florida for evaluation in 2016, 2019, 2020 and 2021. Specifically, for evaluating, identifying, and developing varieties with improved tolerance to *Cercospora apii* (celery early blight). These trials were transplanted in the late fall in order to be present in the most environmental favorable window for natural infection by *Cercospora*. Infection ratings presented here represent an average score from 1 to 5 where 1 represents most susceptible and 5 represents most tolerant. NA=not available=not in the trial.

TABLE 16

| VARIETY | 2016 | 2019 | 2020 | 2021 | Overall Average |
|---|---|---|---|---|---|
| | | | Year | | |
| Floribelle | 5 | 4.5 | 5 | 3.9 | 4.6 |
| TBG 32 | 5 | 3.4 | 4 | 2.8 | 3.8 |
| ADS-2 | NA | NA | 5 | 1.7 | 3.4 |
| ADS-23 | 5 | 2.5 | 4 | 1.5 | 3.3 |
| TBG 53 | NA | NA | 3 | 2.8 | 2.9 |
| TBG 31 | 2 | 2.5 | 5 | 1.8 | 2.8 |
| TBG 28 | NA | 2.5 | 2.5 | 3.2 | 2.7 |
| TBG 37 | NA | 2 | 4 | 1.4 | 2.5 |
| TBG 54 | 1 | 2 | 5 | 1.7 | 2.4 |
| ADS-1 | NA | 2 | 3 | 1.9 | 2.3 |
| TBG 29 | 4 | 1.5 | 2 | 1.2 | 2.2 |
| ADS-20 | NA | 2 | NA | NA | 2.0 |
| TBG 33 | NA | 2.5 | 2 | 1 | 1.8 |
| ADS-22 | NA | 1.5 | NA | NA | 1.5 |
| TBG 34 | NA | 1.5 | NA | NA | 1.5 |
| TBG 43 | NA | 1.5 | NA | NA | 1.5 |
| TBG 35 | 1 | 1.3 | 1 | 1 | 1.1 |
| ADS-8 | 1 | NA | 1 | 1 | 1.0 |
| GREENBAY | NA | 1.5 | NA | NA | 1.5 |

TABLE 16-continued

| VARIETY | 2016 | 2019 | 2020 | 2021 | Overall Average |
|---|---|---|---|---|---|
| | | | Year | | |
| SABROSO | NA | 1.5 | NA | NA | 1.5 |

As shown in Table 16, under these conditions there is some variation between years and in particular 2020 which had several varieties that appeared to perform better than other years. Much of this can be attributed to variable infectious conditions between years, timing of rating the infection and on occasion for plot variation within a year the presence of more infected plots surrounding particular plots which provided more secondary inoculum. On a rating scale of 1 to 5 with 5 being tolerant Floribelle was consistently the most tolerant variety followed by TBG 32. TBG 53 appears to be more similar to parent TBG 32 in 2021 but potentially slightly less tolerant in 2020 and TBG 28 appears to have moderate tolerance more comparable to TBG 31, however more consistent across the years than TBG 31. TBG 54 appears to be fairly similar to sister TBG 31 for tolerance. ADS-2 and ADS 23 also appear to be more tolerant (moderate), however the results were not as consistent between years. Most other varieties including TBG 35 were fairly susceptible to susceptible.

Tables 17 shows the results of trials designed to provide yield comparisons between TBG 54 and its sister TBG 31 and TBG 35 (2018) and TBG 35 (2019) at different planting populations. Based on yields that were calculated on total cartons harvested per acre equivalence TBG 54 consistently outperformed TBG 31 and frequently outperformed TBG 35. TBG 54 did not perform as well as TBG 35 at especially higher populations that were intended for producing celery hearts. So unlike ADS-8 and TBG 35, varieties with particular advantages for high density planting TBG 54's advantage is prominently in the 44,000 plant population or lower.

Table 17 Shows the results of yield trials based on different plant spacing between TBG 54 with TBG 31 and TBG 35 in 2018 and TBG 54 with TBG 35 in 2020. Each trial was grown in Belle Glade, Florida on 36-inch beds. Yields were based on total cartons harvested on an acre equivalent.

TABLE 17

| Plants per acre | In row spacing (inches) on 36-inch beds | Total Carton per Acre Equivalent* | | | | |
|---|---|---|---|---|---|---|
| | | 2018 | | | 2020 | |
| | | TBG 54 | TBG 31 | TBG 35 | TBG 54 | TBG 35 |
| 31,700 | 10.0 | 957 | NA | 775 | 947 | 895 |
| 35,200 | 9.0 | 919 | 865 | 829 | 937 | 956 |
| 39,100 | 8.1 | 1,153 | 1,088 | 1,124 | 1,092 | 1,056 |
| 44,000 | 7.2 | 1,189 | 1,150 | 1,179 | 1,212 | 1,071 |
| 50,300** | 6.3 | 739 | NA | 850 | 713 | 799 |

*Total Carton per Acre Equivalent is the extrapolation of plot yield in cartons to total cartons per acre equivalent.
**This spacing is intended for the production and harvest of smaller celery hearts only so the yields will be lower based on heart pack standards.

As shown in Table 17, In 2018 TBG 54 consistently outperformed (yield as cartons per acre equivalent) sister TBG 31 and except for the higher plant population of 50,300 which is intended for the production of hearts consistently outperformed TBG 35. In 2020 TBG 54 outperformed TBG 35 except for plant populations 35,200 and 50,300. While both were fairly similar, at the 35,200 plant population, like in 2018, TBG 54 did not perform well at the higher plant population of 50,300. Unlike TBG 35, the plant stature/architecture of TBG 54 does not perform well at the highest plant populations intended for production of smaller celery stalks to be used for the celery heart market.

Table 18 shows the results of numerous trials designed to provide yield comparisons between TBG 54 and its sister TBG 31 and/or TBG 35 between the years of 2017 and 2020 (excluding 2019) in four different harvest seasons/months (January to March) in Florida. Based on yields that were calculated on total cartons harvested per acre equivalence TBG 54 fairly consistently outperformed TBG 35 and its sister TBG 35 in all seasons/months of harvest.

Table 18 shows the results of yield trials based on different seasons (harvest months) between TBG 54 and TBG 31 in 2017, TBG 54, TBG 31, and TBG 35 in 2018, and TBG 54 and TBG 35 in 2020. Each trial was grown in Belle Glade, Florida on 36-inch beds and with a plant population of 39,100 plants per acre.

TABLE 18

| | 2017 | | | | 2018 | | |
| | Maturity Days | | Total Carton per Acre Equivalent* | | Maturity Days | | |
| | TBG 54 | TBG 31 | TBG 54 | TBG 31 | TBG 54 | TBG 31 | TBG 35 |
|---|---|---|---|---|---|---|---|
| January | 86 | 86 | 1131 | 1119 | NA | NA | NA |
| February | 94 | 90 | 1191 | 1055 | 96 | 97 | 95 |
| March | NA | NA | NA | NA | 88 | 92 | 90 |
| April | NA | NA | NA | NA | 91 | 96 | 86 |

| | 2018 | | | 2020 | | | |
| | Total Carton per Acre Equivalent* | | | Maturity Days | | Total Carton per Acre Equivalent* | |
| | TBG 54 | TBG 31 | TBG 35 | TBG 54 | TBG 35 | TBG 54 | TBG 35 |
|---|---|---|---|---|---|---|---|
| January | NA | NA | NA | 95 | 90 | 1,141 | 1,033 |
| February | 1,312 | 1,288 | 1,207 | 92 | 91 | 1,028 | 1,031 |
| March | 996 | 1,030 | 1,089 | 91 | 89 | 1,142 | 1,079 |
| April | 878 | 693 | 826 | 87 | 85 | 1,041 | 993 |

*Total Carton per Acre Equivalent is the extrapolation of plot yield in cartons to total cartons per acre equivalent.

As shown in Table 18, in 2017 and 2018 TBG 54 consistently outperformed (yield as cartons per acre equivalent) sister TBG 31 in every harvest month except for March of 2018 when it did not perform as well. The performance of TBG 54 in March 2018 appeared to have been differentially impacted by cultivation injury. TBG 54 also outperformed TBG 35 in every trial during the 2018 and 2020 harvest seasons except for March 2018 (again due to differential cultivation injury) and February 2020 when there was little difference for yield between the varieties. TBG 54 could generally be allowed 1 to 4 more days to grow larger (Maturity Days) compared to TBG 35 before over maturity would become an issue. However, in 2018 TBG 31 was allowed more time to mature compared to sister TBG 54 and still did not yield as well. In 2017 TBG 54 was either harvested the same day or allowed to mature longer than TBG 31.

The use of the terms "a," "an," and "the," and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. For example, if the range 10-15 is disclosed, then 11, 12, 13, and 14 are also disclosed. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

DEPOSIT INFORMATION

A deposit of the celery cultivar seed of this invention is maintained by A Duda & Sons, Inc., 1200 Duda Trail, Oviedo, Florida 32765, U.S.A. Access to this deposit will be available during the pendency of this application to persons determined by the Commissioner of Patents and Trademarks to be entitled thereto under 37 CFR § 1.14 and 35 USC § 122. Upon allowance of any claims in this application, all restrictions on the availability to the public of the variety will be irrevocably removed by affording access to a deposit of at least 625 seeds of the same variety with the American Type Culture Collection (ATCC), 10801 University Boulevard, Manassas, Va. 20110, Accession No. PTA-127792.

While a number of exemplary aspects and embodiments have been discussed above, those of skill in the art will recognize certain modifications, permutations, additions, and sub-combinations thereof. It is therefore intended that the following appended claims and claims hereafter introduced are interpreted to include all such modifications, permutations, additions, and sub-combinations as are within their true spirit and scope.

What is claimed is:

1. A seed, plant, or a plant part thereof, of celery cultivar designated TBG 54, wherein a representative sample of seed of said cultivar has been deposited under ATCC Accession No. PTA 127792.

2. A celery plant, or a plant part thereof, having all of the physiological and morphological characteristics of the celery plant of claim 1.

3. A tissue or cell culture produced from protoplasts or cells from the plant of claim 1, wherein said cells or protoplasts are produced from a plant part selected from the group consisting of leaf, callus, pollen, ovule, embryo, cotyledon, hypocotyl, meristematic cell, root, root tip, pistil, anther, flower, seed, shoot, stem, stalk, petiole, and sucker.

4. A celery plant regenerated from the tissue culture of claim 3, wherein said regenerated plant comprises all of the morphological and physiological characteristics of celery cultivar TBG 54.

5. A method of producing a celery seed, wherein the method comprises crossing the plant of claim 1 with a different celery plant and harvesting the resultant celery seed.

6. F1 celery seed produced by the method of claim 5.

7. A F1 celery plant, or a plant part thereof, produced by growing said seed of claim 6.

8. A method of producing an herbicide resistant celery plant, wherein said method comprises introducing a gene conferring herbicide resistance into the plant of claim 1.

9. A herbicide resistant celery plant produced by the method of claim 8, wherein the gene confers resistance to a herbicide selected from the group consisting of glyphosate, sulfonylurea, imidazolinone, dicamba, glufosinate, phenoxy proprionic acid, L-phosphinothricin, cyclohexone, cyclo-hexanedione, triazine, benzonitrile protoporphyrinogen oxidase (PPO)-inhibitor herbicides, auxin herbicides, and broxynil, and wherein the herbicide resistant celery plant comprises the gene conferring resistance to the herbicide and otherwise all of the physiological and morphological characteristics of celery cultivar TBG 54.

10. A method of producing a pest or insect resistant celery plant, wherein said method comprises introducing a gene conferring pest or insect resistance into the celery plant of claim 1.

11. A pest or insect resistant celery plant produced by the method of claim 10, wherein the pest or insect resistant celery plant comprises the gene conferring resistance to the pest or insect and otherwise all of the physiological and morphological characteristics of celery cultivar TBG 54.

12. The celery plant of claim 11, wherein the gene encodes a *Bacillus thuringiensis* (Bt) endotoxin.

13. A method of producing a disease resistant celery plant, wherein said method comprises introducing a gene into the celery plant of claim 1.

14. A disease resistant celery plant produced by the method of claim 13, wherein the disease resistant celery plant comprises the gene conferring disease resistance and otherwise all of the physiological and morphological characteristics of celery cultivar TBG 54.

15. A method of producing a celery plant with modified fatty acid metabolism or modified carbohydrate metabolism comprising transforming the celery plant of claim 1 with a transgene encoding a protein selected from the group consisting of fructosyltransferase, levansucrase, α-amylase, invertase and starch branching enzyme or DNA encoding an antisense of stearyl-ACP desaturase.

16. A celery plant having modified fatty acid metabolism or modified carbohydrate metabolism produced by the method of claim 15, wherein the celery plant having modified fatty acid metabolism or modified carbohydrate metabolism comprises the transgene and otherwise all of the physiological and morphological characteristics of celery cultivar TBG 54.

17. A method for producing a male sterile celery plant, wherein said method comprises transforming the celery plant of claim 1 with a nucleic acid molecule that confers male sterility.

18. A male sterile celery plant produced by the method of claim 17, wherein the male sterile celery plant comprises the nucleic acid molecule that confers male sterility and otherwise all of the physiological and morphological characteristics of celery cultivar TBG 54.

19. A method of introducing a desired trait into celery cultivar TBG 54, wherein the method comprises:

(a) crossing a TBG 54 plant, wherein a representative sample of seed was deposited under ATCC Accession No. PTA-127792, with a plant of another celery cultivar that comprises a desired trait to produce progeny plants, wherein the desired trait is selected from the group consisting of improved nutritional quality, industrial usage, male sterility, herbicide resistance, insect resistance, modified seed yield, modified lodging resistance, modified iron-deficiency chlorosis and resistance to bacterial disease, fungal disease or viral disease;

(b) selecting one or more progeny plants that have the desired trait to produce selected progeny plants;

(c) backcrossing the selected progeny plants with the TBG 54 plants to produce backcross progeny plants;

(d) selecting for backcross progeny plants that have the desired trait; and (e) repeating steps (c) and (d) two or more times in succession to produce selected third or higher backcross progeny plants that comprise the desired trait.

20. A celery plant produced by the method of claim 19, wherein the plant has the desired trait and otherwise all of the physiological and morphological characteristics of celery cultivar TBG 54.

21. The celery plant of claim 20, wherein the desired trait is herbicide resistance and the resistance is conferred to a herbicide selected from the group consisting of imidazolinone, dicamba, cyclohexanedione, sulfonylurea, glyphosate, glufosinate, phenoxy proprionic acid, L-phosphinothricin, triazine, benzonitrile protoporphyrinogen oxidase (PPO)-inhibitor herbicides, auxin herbicides, and broxynil.

22. The celery plant of claim 20, wherein the desired trait is insect resistance and the insect resistance is conferred by a gene encoding a *Bacillus thuringiensis* endotoxin.

23. The celery plant of claim 20, wherein the desired trait is male sterility and the trait is conferred by a cytoplasmic nucleic acid molecule.

24. A method of producing a genetically modified celery plant, wherein the method comprises mutation, transformation, gene conversion, genome editing, RNA interference or gene silencing of the plant of claim 1.

25. A genetically modified celery plant produced by the method of claim 24, wherein the plant comprises the genetic modification and otherwise comprises all of the physiological and morphological characteristics of celery cultivar TBG 54.

* * * * *